US012529043B2

(12) United States Patent
Izhar et al.

(10) Patent No.: US 12,529,043 B2
(45) Date of Patent: *Jan. 20, 2026

(54) OMNI-103 CRISPR NUCLEASE

(71) Applicant: EmendoBio Inc., Wilmington, DE (US)

(72) Inventors: Lior Izhar, Tel Aviv (IL); Nadav Marbach Bar, Rehovot (IL); Liat Rockah, Rishon LeZion (IL); Nurit Meron, Ramat Gan (IL); Ophir Adiv Tal, Rehovot (IL); Ariel Gispan, Kfar Adumim (IL); Idit Buch, Hod-Hasharon (IL); Nir Hecht, Tel Aviv (IL)

(73) Assignee: EmendoBio Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/613,508

(22) Filed: Mar. 22, 2024

(65) Prior Publication Data

US 2025/0051741 A1 Feb. 13, 2025

Related U.S. Application Data

(63) Continuation of application No. 18/006,372, filed as application No. PCT/US2022/015504 on Feb. 7, 2022, now Pat. No. 12,091,688.

(60) Provisional application No. 63/286,855, filed on Dec. 7, 2021, provisional application No. 63/214,506, filed on Jun. 24, 2021, provisional application No. 63/147,166, filed on Feb. 8, 2021.

(51) Int. Cl.
*C12N 9/22* (2006.01)
*C12N 15/11* (2006.01)

(52) U.S. Cl.
CPC ................ *C12N 9/22* (2013.01); *C12N 15/11* (2013.01); *C12N 2310/20* (2017.05); *C12N 2310/531* (2013.01); *C12N 2800/80* (2013.01)

(58) Field of Classification Search
CPC ........................................................ C12N 9/22
See application file for complete search history.

(56) References Cited

U.S. PATENT DOCUMENTS

| | | | |
|---|---|---|---|
| 11,666,641 | B2 | 6/2023 | Baram et al. |
| 2019/0264232 | A1 | 8/2019 | Hou et al. |
| 2020/0325495 | A1 | 10/2020 | Doudna et al. |
| 2020/0332288 | A1 | 10/2020 | Kantardzhieva et al. |
| 2022/0154157 | A1 | 5/2022 | Baram et al. |
| 2022/0202913 | A1 | 6/2022 | Baram et al. |
| 2022/0213456 | A1 | 7/2022 | Baram et al. |
| 2023/0122086 | A1 | 4/2023 | Izhar et al. |

FOREIGN PATENT DOCUMENTS

| | | | |
|---|---|---|---|
| JP | 2015523856 | A | 8/2015 |
| JP | 2020513824 | A | 5/2020 |
| WO | 2017184768 | A1 | 10/2017 |
| WO | 2018172556 | A1 | 9/2018 |
| WO | 2019165168 | A1 | 8/2019 |
| WO | 2020069029 | A1 | 4/2020 |
| WO | 2020197934 | A1 | 10/2020 |
| WO | 2020223514 | A2 | 11/2020 |
| WO | 2021243058 | A1 | 12/2021 |
| WO | 2022087135 | A1 | 4/2022 |
| WO | 2022098693 | A1 | 5/2022 |
| WO | 2022170199 | A2 | 8/2022 |
| WO | 2022170216 | A2 | 8/2022 |
| WO | 2022226215 | A1 | 10/2022 |
| WO | 2023019263 | A1 | 2/2023 |
| WO | 2023019269 | A2 | 2/2023 |
| WO | 2023091987 | A2 | 5/2023 |
| WO | 2023102407 | A2 | 6/2023 |
| WO | 2023107946 | A2 | 6/2023 |

OTHER PUBLICATIONS

International Preliminary Report on Patentability for PCT/US2022/081019 mailed Jun. 5, 2024.
International Search Report and Written Opinion for International Application No. PCT/US2022/015504 dated Jul. 15, 2022.
International Search Report and Written Opinion for International Application No. PCT/US2022/081019 dated Jun. 1, 2023.
Hrishikesh S. Kulkarni et al., "Intercellular C3 Protects Human Airway Epithelial Cells from Stress-associated Cell Death" American Journal of Respiratory Cell and Molecular Bioligy, vol. 60, No. 2, Feb. 1, 2019 & Online Data Supplement.
Hu et al., "Comparison of Various Nuclear Localization Signal-Fused Cas9 Proteins and Cas9 mRNA for Genome Editing in Zebrafish" G3 Genes | Genomes| Genetics, vol. 8, Mar. 1, 2018, pp. 823-831.
International Preliminary Report on Patentability for International Application No. PCT/US2022/081019 dated Jun. 5, 2024.
Makarova et al. "Evolutionary classification of CRISPR-Cas systems: a burst of class 2 and derived variants", Nature Reviews Microbiology, vol. 18 No. 2, Dec. 19, 2019, pp. 67-83.
Pavani et al, "Ex vivo editing of human hematopoietic stem cells for erythroid expression of therapeutic proteins", Nature Communications, vol. 11, No. 1, Jul. 20, 2020.
Wei Zhang, et al: "Generation of complement protein C3 deficient pigs by CRISPR/Cas9-mediated gene targeting" Scientific Reports, vol. 7, No. 1, Jul. 10, 2017.
Zhou Zhicheng et al. "Structural and functional insights into the bona fide catalytic state of *Streptococcus pyogenes* Cas9 HNH nuclease domain", Jul. 30, 2019, retrieved from internet: URL: https://pmc.ncbi.nlm.nih.gov/articles/PMC6706240/pdf/elife-46500.pdf.

(Continued)

*Primary Examiner* — Suzanne M Noakes
(74) *Attorney, Agent, or Firm* — Potomac Law Group, PLLC; Jamaica Potts Szeliga

(57) ABSTRACT

The present invention provides a non-naturally occurring composition comprising a CRISPR nuclease comprising a sequence having at least 95% identity to the amino acid sequence of SEQ ID NO: 1 or a nucleic acid molecule comprising a sequence encoding the CRISPR nuclease.

11 Claims, 17 Drawing Sheets

Specification includes a Sequence Listing.

(56) References Cited

OTHER PUBLICATIONS

Peinan Hu et al: "Comparison of Various Nuclear Localization Signal-Fused Cas9 Proteins and Cas9 mRNA for Genome Editing in Zebrafish", G3 GENEs:GENOMEs:GENETICS, vol. 8, Mar. 1, 2018 (Mar. 1, 2018), pp. 823-831.
Office Action for Japanese Application No. 2023-547664, dated Nov. 25, 2025.

sgRNA 12 V2

OMNI-103, sgRNA_12 v1 positions 1-8 v2 positions 1-8

| 1 | 2 | 3 | 4 | 5 | 6 | 7 | 8 | ratio |
|---|---|---|---|---|---|---|---|---|
| | | A | A | C | T | | | 0.06 |
| | | A | G | C | T | | | 0.06 |
| | | | A | C | T | C | | 0.07 |
| | | G | A | C | T | | | 0.08 |
| | | | A | C | T | T | | 0.10 |
| | | C | A | C | T | | | 0.11 |
| | | | A | A | C | T | | 0.11 |
| | | | A | C | T | A | | 0.13 |
| | | | A | C | T | G | | 0.16 |
| | | | G | A | C | T | | 0.17 |
| | | G | A | T | T | | | 0.19 |
| | | A | A | T | T | | | 0.22 |
| | C | A | A | C | | | | 0.28 |
| | G | A | A | C | | | | 0.33 |
| | C | G | A | C | | | | 0.36 |
| | A | A | C | T | | | | 0.39 |
| | | | | A | C | T | T | 0.40 |
| | A | A | A | C | | | | 0.41 |
| | T | A | A | C | | | | 0.43 |
| | | | | A | C | T | C | 0.51 |
| | | | | C | T | T | G | 0.58 |
| | | | | C | T | G | G | 0.59 |
| | | | | C | T | T | C | 0.59 |
| | | | | A | C | T | G | 0.60 |
| C | G | A | A | | | | | 0.67 |
| T | G | G | A | | | | | 0.69 |
| T | C | G | A | | | | | 0.69 |
| T | A | A | A | | | | | 0.71 |
| A | G | A | A | | | | | 0.71 |
| C | G | G | A | | | | | 0.76 |

| 1 | 2 | 3 | 4 | 5 | 6 | 7 | 8 | ratio |
|---|---|---|---|---|---|---|---|---|
| | | T | A | C | T | | | 0.03 |
| | | | A | A | C | T | | 0.03 |
| | | | A | C | T | T | | 0.04 |
| | | | A | C | T | C | | 0.04 |
| | | | G | A | C | T | | 0.04 |
| | | G | G | C | T | | | 0.04 |
| | | A | A | C | T | | | 0.05 |
| | A | A | C | T | | | | 0.05 |
| | | G | A | T | T | | | 0.06 |
| | | G | A | C | T | | | 0.06 |
| | | A | A | C | G | | | 0.06 |
| | | | A | C | T | G | | 0.07 |
| | | | A | C | T | A | | 0.07 |
| | C | A | A | C | | | | 0.08 |
| | G | A | A | C | | | | 0.11 |
| | T | A | A | C | | | | 0.12 |
| | A | A | A | C | | | | 0.14 |
| | C | G | A | C | | | | 0.18 |
| | | | | A | C | T | T | 0.21 |
| | | | | C | T | T | C | 0.34 |
| | | | | A | C | T | A | 0.36 |
| | | | | A | C | T | C | 0.36 |
| | | | | C | T | G | G | 0.39 |
| | | | | C | T | C | G | 0.39 |
| C | G | G | A | | | | | 0.53 |
| C | G | A | A | | | | | 0.61 |
| G | C | G | A | | | | | 0.61 |
| A | G | G | A | | | | | 0.62 |
| C | T | A | A | | | | | 0.63 |
| T | G | G | A | | | | | 0.63 |

OMNI-103,
sgRNA_32 v1 v2 v3

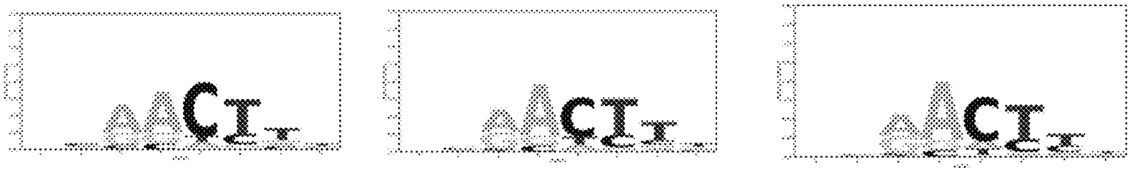

v1

| 1 | 2 | 3 | 4 | 5 | 6 | 7 | 8 | ratio |
|---|---|---|---|---|---|---|---|---|
| | | A | G | C | T | | | 0.01 |
| | C | A | A | C | | | | 0.01 |
| | | C | A | C | T | | | 0.02 |
| | | A | A | C | T | | | 0.02 |
| | | A | A | C | G | | | 0.02 |
| | G | A | A | C | | | | 0.02 |
| | | | A | A | C | T | | 0.03 |
| | | G | A | C | T | | | 0.03 |
| | | G | A | C | C | | | 0.03 |
| | | | A | C | T | G | | 0.03 |
| | | | A | C | T | A | | 0.03 |
| | | | A | C | T | T | | 0.03 |
| | A | A | C | T | | | | 0.04 |
| | | A | C | C | T | | | 0.04 |
| | | G | G | C | T | | | 0.04 |
| | | | A | C | T | C | | 0.04 |
| | | A | A | C | C | | | 0.04 |
| | T | A | A | C | | | | 0.05 |
| | G | A | C | T | | | | 0.05 |
| | | | G | A | C | T | | 0.05 |
| | | G | C | C | T | | | 0.05 |
| | | G | A | T | T | | | 0.05 |
| | | G | A | C | G | | | 0.06 |
| | | A | A | T | T | | | 0.06 |
| | | T | A | C | T | | | 0.06 |
| | A | A | A | C | | | | 0.06 |
| | | A | A | C | A | | | 0.07 |
| | C | G | A | C | | | | 0.07 |
| | G | G | A | C | | | | 0.08 |

v2

| 1 | 2 | 3 | 4 | 5 | 6 | 7 | 8 | ratio |
|---|---|---|---|---|---|---|---|---|
| | | A | A | T | T | | | 0.02 |
| | | G | A | C | T | | | 0.03 |
| | | A | A | C | C | | | 0.03 |
| | C | G | A | C | | | | 0.03 |
| | | G | A | T | T | | | 0.03 |
| | | | A | C | T | T | | 0.03 |
| | | G | G | C | T | | | 0.03 |
| | | G | A | C | C | | | 0.03 |
| | | | A | C | T | C | | 0.04 |
| | | A | C | C | T | | | 0.04 |
| | | | A | A | C | T | | 0.04 |
| | | | G | A | C | T | | 0.04 |
| | | C | A | C | T | | | 0.04 |
| | | A | A | C | G | | | 0.04 |
| | | | A | C | T | A | | 0.04 |
| | | A | A | C | T | | | 0.04 |
| | | A | G | C | T | | | 0.04 |
| | A | A | A | C | | | | 0.04 |
| | C | A | A | C | | | | 0.05 |
| | | | A | C | T | G | | 0.05 |
| | G | A | A | C | | | | 0.05 |
| | | T | A | C | T | | | 0.05 |
| | A | A | C | T | | | | 0.05 |
| | T | A | A | C | | | | 0.06 |
| | | | | A | C | T | T | 0.06 |
| | | G | A | C | G | | | 0.06 |
| | | A | A | C | A | | | 0.06 |
| | | G | C | C | T | | | 0.08 |
| | G | G | A | C | | | | 0.09 |

v3

| 1 | 2 | 3 | 4 | 5 | 6 | 7 | 8 | ratio |
|---|---|---|---|---|---|---|---|---|
| | | | A | C | T | C | | 0.01 |
| | | | A | A | C | T | | 0.02 |
| | | G | A | C | T | | | 0.02 |
| | | | A | C | T | A | | 0.02 |
| | | G | A | C | C | | | 0.03 |
| | T | A | A | C | | | | 0.03 |
| | | A | A | C | C | | | 0.03 |
| | C | A | A | C | | | | 0.03 |
| | C | G | A | C | | | | 0.03 |
| | | C | A | C | T | | | 0.03 |
| | | A | A | T | T | | | 0.03 |
| | | G | C | C | T | | | 0.03 |
| | | A | A | C | T | | | 0.03 |
| | | | G | A | C | T | | 0.03 |
| | | A | A | C | A | | | 0.03 |
| | | G | A | T | T | | | 0.03 |
| | | T | A | C | T | | | 0.03 |
| | G | G | A | C | | | | 0.04 |
| | G | A | A | C | | | | 0.04 |
| | | G | G | C | T | | | 0.04 |
| | | A | G | C | T | | | 0.04 |
| | | G | A | C | G | | | 0.04 |
| | | | A | C | T | T | | 0.04 |
| | | | A | C | T | G | | 0.04 |
| | G | A | C | T | | | | 0.05 |
| | A | A | A | C | | | | 0.05 |
| | A | A | C | T | | | | 0.05 |
| | | A | A | C | G | | | 0.05 |
| | | A | C | C | T | | | 0.06 |

Fig. 4B

Deletion 1: Upper stem

Deletion 2: Terminal hairpin

| | | |
|---|---|---|
| 103.v2 | GTTTGAGAGTAGTGTAAGAAATTACACTACAAGTTCAAATAAAAATTTATTCAAATCCATTTGCTACATTGTGTAGAATTTAAAGATCTGGCAACAGATCTTTTTTT | 107 |
| OMNI-103.1 | GTTTGAGAGTAGTG---GAAA---CACTACAAGTTCAAATAAAAATTTATTCAAATCCATTTGCTACATTGTGTAGAATTTAAAGATCTGGCAACAGATCTTTTTTT | 101 |
| OMNI-103.2 | GTTTGAGAGTAGTGTAAGAAATTACACTACAAGTTCAAATAAAAATTTATTCAAATCCATTTGCTACATTGTGTAGAA----------------------TTTTTTT | 85 |
| OMNI-103.3 | GTTTGAGAGTAGTG---GAAA---CACTACAAGTTCAAATAAAAATTTATTCAAATCCATTTGCTACATTGTGTAGAA----------------------TTTTTTT | 79 |
| OMNI-103.4 | GTTTGAGAGTAGTG---GAAA---CACTACAAGTTCAAATAAAAATTTATTCAAATCCATTTGCTACATTGTGTAGAATTTAAAGAT---GCAA---ATCTTTTTTT | 95 |

Fig. 5A

| Sample Name | % TCR Negative (% editing) | GeoMean |
|---|---|---|
| V2.3 | 90.8 | 2511 |
| V2.2 | 87.6 | 2621 |
| V2 | 77.4 | 3324 |
| Non Treated (Positive control) | 6.28 | 12617 |
| IgG control (Negative control) | 100 | 924 |

| Sample Name | % TCR Negative (% editing) | GeoMean |
|---|---|---|
| V2.3 | 91.6 | 7710 |
| V2.2 | 88 | 5581 |
| V2 | 79.9 | 8029 |
| Non Treated (Positive control) | 1.56 | 7.59E5 |
| IgG control (Negative control) | 99.8 | 257 |

| Sample Name | CD3+ :: Freq. of Parent | Geometric Mean : FL5-A |
|---|---|---|
| 01-4200-86.fcs | 96.9 | 16409 |
| 01-REA-A6.fcs | 1.98 | 1543 |

| Sample Name | CD25+ :: Freq. of Parent | Geometric Mean : FL7-A |
|---|---|---|
| 01-4200-86.fcs | 85.3 | 27069 |
| 01-REA-A6.fcs | 3.96 | 176 |

SEQUENCE LISTING

```
Sequence total quantity: 135
SEQ ID NO: 1            moltype = AA  length = 1348
FEATURE                 Location/Qualifiers
REGION                  1..1348
                        note = OMNI-103
source                  1..1348
                        mol_type = protein
                        organism = unidentified
SEQUENCE: 1
MSIKSDYFLG LDIGTDSIGW AVTDPEYHIL RRKGKALWGI RLFDAANTAA ERRTFRTSRR  60
RIQRRRQRIR LLQELFAEEM VKLDPGFFQR LSDSAFWQED KQEQQIYSLF TCENYTDVDY  120
YREYPTIYHL RSALIQEKKE FDLRLLYLAL HHLMKHRGHF LFNGSINNVT SFHTTFQTFA  180
DCLYDEFDIE LECDSEDRFA EILKDKHARK TGKCSELEII CHIEKSNKQL KELFKLITGM  240
KASLSVVFGD DELAEIEHNK ISFSESSYDE VRLALEDEIQ ERTGILDIFH AVYSWAILAD  300
ILEGGEYEGN SYLSVAKVST YKKHGDDLRL LRTLVREYCP DHYKSFFSVS GKENYCAYAG  360
TLKKNGKKQP IKRCSQEDFY KALKKLLNQM PTEQPEVKDI FIEIENGTFL PLQVSKDNGV  420
IPYQVNKMEL EKILQNAEEY LPFLKNIDEE CGKTVSKKII DLFEFRIPYY VGPLNTAKGE  480
NCWMVRKEAG RIYPWNFDEK VDRDQSAEKF IRRMTNQCTY LIHEDVVPKN SLLYSEFMVL  540
```

-continued

```
NELNNVKIRS EKLPVELKQA IVLDLFKKQK QITGKKLLNY LNANGYDVKK EDLSGFDGNF  600
KSSLSSYLTL KKVFGEELDK YSVQQMAEDI ILWITLYGDD QKMLRRVIRK HYEQQLSEEQ  660
ILSLSKLKFQ GWGRLSRRLL SEMEGVDCET GECMTVMQGL RNTQNNLMQL LSQQFSFMEL  720
IEEENGNYYV DEITYDNLVK DMVISPSVKR AVWQTVQIVE EIKGVMGCQP KKIFVEMARS  780
DEEKKRTVSR KDRLLEAYDA IKDEARQWQE ELQKYSDGDF KAIKLYLYYT QMGQCMYTGR  840
KIDLSQLNDA TVWDRDHIYP QSKTKDDSLD NLVLVDRSVN AKKSDGMLSP EIQQRMRATW  900
KYLKEKKLIS EKKYERLTRV SPLTDEELAG FINRQLVETR QSSKAVATLL KRVYDEAEIV  960
YVKAEAVSNF RRDNLDYIKV RDLNDYHHAK DAYQNIVVGN VFHEKFTSNP LRWLKNNPNT  1020
KYSLNQMFNF DLEKNGVVIW KRGKAGSIKC VEETLKRNDI LFTRYAFCNK GGFFNQMLTA  1080
APEDKTKAKG LVPIKKGMET WKYGGYTSVT PSHFMLVASK DKKGKEIRTI ETVPLYRWKE  1140
FKENPDALLQ YCREFYGLKE PKVLIPCIKK NARLVVNGFP MHLKGSTGKQ LILQGAVQLC  1200
LNNENIKYLK KVTKYLEYNA QRRDKRTLLE VREVTGINKE ENIQLYDVFV DKLSNTIYQY  1260
RPANPKDNLI KGREKFIELG LAEQCVVLGE VLHLFQCKPL TSDLTLIGGS PNTGTIKITK  1320
TISNCNVVKL LSQSIAGVKV REINLLII                                    1348

SEQ ID NO: 2            moltype = DNA  length = 4047
FEATURE                 Location/Qualifiers
misc_feature            1..4047
                        note = OMNI-103
source                  1..4047
                        mol_type = other DNA
                        organism = unidentified
SEQUENCE: 2
atgagcataa aaagtgatta ttttttagga cttgatattg gtacggattc tattggatgg  60
gcggtaaccg acccagaata tcacatattg agacgaaaag gtaaagcatt atggggaata  120
agattatttg atgcggccaa tacagcggca gaacggcgaa catttaggac aagccgaaga  180
aggattcaga gaagacgaca gagaattcgg ttattgcaag aattatttgc agaagaaatg  240
gtaaaattag acccaggatt ttttcagagg ttgtcagaca gcgcattttg gcaggaggat  300
aagcaagagc agcaaattta ttcacttttt acttgtgaaa attatacaga tgttgattat  360
tacagagaat atcctactat ttatcatttg agaagtgcat tgattcagga aaagaaggaa  420
tttgatcttc gtcttctata tcttgctctt caccatttga tgaagcacag gggacatttc  480
ctgtttaatg ggagtattaa taatgtgacg tcatttcata cgacgtttca gacgtttgca  540
gattgtcttt atgatgagtt tgatatagaa ctggaatgtg attccgaaga tagatttgca  600
gaaattttaa aggataaaca tgccagaaaa acaggaaaat gttctgaatt agagataatc  660
tgtcatatag aaaaatcaaa taagcagcta aaagaacttt ttaaattaat tacaggaatg  720
aaagctagtt tgagtgttgt gtttggtgat gatgagttag cggaaataga acataataag  780
attagttttt cagagagtag ttatgatgaa gtacgtcttg cattggagga tgagattcag  840
gagaggactg gtatactgga tatctttcat gcagtttata gttgggcgat tctcgcggat  900
attttagaag gcggagaata tgaggggaat tcttatctaa gcgttgcgaa ggtaagcact  960
tataaaaagc atggtgatga tttgcggttg ctaagaacac tggttcggga atattgtcct  1020
gatcattaca aatctttctt ttccgtatca gggaaggaga attattgtgc atatgcgggt  1080
actttaaaaa agaatggaaa aaaacagccg attaaacgtt gcagccagga agatttttat  1140
aaagcgttaa agaaattgct gaatcagatg ccgacagaac aaccagaagt gaaagacatc  1200
ttcatcgaaa ttgaaaatgg tacttttttg ccgttgcagg taagtaagga taatggagtg  1260
ataccttatc aggtaaataa gatggaatta gaaaaaatcc tgcagaatgc agaggaatat  1320
ttgccatttc taaaaaatat agatgaagaa tgtggaaaaa cggttagtaa gaagattata  1380
gatctctttg agtttagaat accatattat gtagggccgc ttaataccgc taaaggagaa  1440
aactgttgga tggtcagaaa agaagcgggg agaatatatc cgtggaattt tgatgaaaag  1500
gtagacagag atcaatcagc agaaaaattt atccgtagaa tgacgaatca gtgtacatat  1560
ttaatacatg aggatgttgt acctaaaaat tctttgcttt attcggagtt tatggtgctt  1620
aatgaattaa ataatgtaaa gatccggtct gagaagctgc cggtggagtt aaaacaggca  1680
atagtattgg atttgtttaa gaaacaaaag cagataacag gaaaaaaact tcttaattac  1740
ttgaatgcaa atggatatga tgtaaaaaaa gaagatttgt cagggtttga cggaaacttt  1800
aaatcatctc tgtcatcata tcttactttg aaaaaagtat ttggtgaaga attagataaa  1860
tatagtgtgc agcagatggc agaggatatt atcttgtgga tcactctgta tggagatgat  1920
cagaagatgt tgcgcagggt aattcgaaaa cattatgaac agcaattgag tgaagaacag  1980
attctttcct tatcgaaatt gaaattccaa ggctggggaa gattatccag acgacttttg  2040
agtgaaatgg aaggcgttga ttgtgagact ggtgagtgta tgacggtcat gcaaggactt  2100
cgtaatactc agaataatct gatgcagctt ctaagtcagc agttttcatt tatggaattg  2160
attgaggaag aaaatgggaa ttattatgta gatgagatta catacgataa tcttgtgaaa  2220
gatatggtta tatctccgtc agtgaagaga gcagtctggc agacagttca gattgtggag  2280
gagattaagg gggtaatggg ctgtcagcct aagaagatat ttgtcgagat ggcgcgaagc  2340
gatgaagaga aaaagcgtac tgtatctagg aaagacaggt tattagaagc atatgatgcg  2400
atcaaggatg aggctcgtca atggcaggaa gagttgcaaa agtattcaga tggtgatttt  2460
aaggctatta aactttatct gtattatacg cagatggggc aatgtatgta tactggaaga  2520
aagatagatc tgtcacaatt aaatgatgcg acggtatggg acagagatca tatatatcca  2580
cagtccaaaa caaaagatga tagtctggat aatctggtat tggtagaccg gagcgtgaac  2640
gctaagaaaa gtgatgggat gctatcacct gagattcagc agagaatgcg ggctacttgg  2700
aaatacttaa aagagaaaaa gttgatttca gagaagaaat atgagcgttt gactagggtc  2760
tcaccactta cagatgagga attggcaggt tttattaatc gacagttagt tgaaacacgt  2820
cagtcttcga aagcagtagc aacacttttg aaacgagtat atgatgaagc ggagattgtc  2880
tatgtaaaag cggaagctgt ttcaaatttt agaagagata atttggatta tattaaggtg  2940
cgtgatctga atgattatca tcatgctaaa gatgcatatc agaatattgt agtggggaat  3000
gtttttcatg agaaatttac cagcaatccg cttcgttggc tgaaaaacaa tcctaatacg  3060
aaatatagtt taaatcagat gtttaacttt gatttagaga aaaatggggt ggtaatatgg  3120
aaaaggggga aggctggaag tattaaatgt gttgaagaaa cattgaaaag aaatgatatt  3180
ctttttacac gatatgcttt ttgtaataaa ggtggttttt ttaaccagat gttaacggca  3240
gctccagaag ataaaacgaa agcaaaggga cttgtaccaa taaaaaaagg tatggaaaca  3300
tggaaatacg gggatatac atcagtaact ccgtcacatt ttatgttggt tgcttcgaaa  3360
```

```
gataagaaag gaaaggagat aagaacgatt gagacagttc cgttgtatag gtggaaagag  3420
ttcaaagaaa atccagatgc attactccaa tattgtagag agttctatgg tttgaaagag  3480
cccaaggtgt tgataccatg catcaagaag aatgccagat tagtcgttaa tggatttcca  3540
atgcatttga aagggagtac aggaaaacaa ttgattttgc agggagcggt tcaattatgt  3600
ctgaataatg aaaatataaa gtatttgaaa aaagtcacaa aatatttgga atataatgca  3660
cagagaagag ataaaagaac actgctggaa gtaagagagg ttacaggaat taacaaagag  3720
gaaaatatac agttatatga tgtgtttgtt gataaattga gtaacacaat atatcagtat  3780
cgtccggcca atccaaagga caatcttata aaaggaagag agaagtttat agaattaggg  3840
ttggcagaac aatgtgttgt gttaggtgaa gtattgcatt tgttccaatg taaaccactc  3900
acgtctgatt tgactttgat tggaggttca ccgaatacag ggacaataaa aataacaaag  3960
acaattagta attgtaatgt tgtaaagttg ttaagccaat ctattgcagg tgttaaagtg  4020
agagaaatta atttgttaat aatatga                                     4047

SEQ ID NO: 3           moltype = DNA  length = 4047
FEATURE                Location/Qualifiers
misc_feature           1..4047
                       note = OMNI-103 human optimized DNA sequence
source                 1..4047
                       mol_type = other DNA
                       organism = synthetic construct
SEQUENCE: 3
atgtctatca agagcgacta cttcctgggc ctcgacatcg gcacagattc tatcggatgg  60
gccgtgacag accccgagta ccacatcctg agaagaaagg gcaaagccct gtggggcatc  120
agactgttcg atgccgccaa tactgccgcc gagagaagaa ccttccggac cagcagaaga  180
agaatccagc ggcggagaca gcggatcaga ctgctgcaag agctgttcgc cgaggaaatg  240
gttaagctgg accccggctt cttccagaga ctgagcgata gcgccttctg gcaagaggac  300
aagcaagagc agcagatcta cagcctgttt acctgcgaga actacaccga cgtggactac  360
tacagagagt accccaccat ctaccacctg agaagcgccc tgatccaaga gaaaaaagag  420
ttcgacctgc ggctgctgta tctggccctg caccatctga tgaagcaccg gggccacttt  480
ctgttcaacg gcagcatcaa caacgtgacc agcttccaca ccaccttcca gaccttcgcc  540
gactgcctgt acgacgagtt cgacatcgag ctggaatgcg acagcgagga cagattcgcc  600
gagatcctga aggataagca cgccagaaag accggcaagt gctctgagct ggaaatcatc  660
tgccacatcg agaagtccaa caagcagctg aaagaactgt tcaagctgat caccggcatg  720
aaggccagcc tgagcgtggt gtttggagat gatgagctgg ccgagatcga gcacaacaag  780
atcagcttca gcgagagcag ctacgacgaa gtgcggctgg ccctggaaga tgagattcaa  840
gagagaaccg gcatcctgga catcttccac gccgtgtatt cttgggccat cctggccgat  900
attctggaag gcggcgagta cgagggcaac agctatctgt ctgtggccaa ggtgtccacc  960
tacaagaagc acggcgacga cctgagactg ctgagaacac tcgtgcgcga gtactgcccc  1020
gaccactaca agagcttttt cagcgtgtcc ggcaaagaga actactgcgc ctacgccggc  1080
acactgaaga agaacggcaa gaagcagccc atcaagcggt gcagccaaga ggacttctac  1140
aaggccctga agaaactgct gaaccagatg cctaccgagc agcccgaagt gaaggatatc  1200
ttcatcgaga ttgagaacgg caccttcctg cctctgcaag tgtccaagga caacggcgtg  1260
atcccctacc aagtgaacaa gatggaactc gagaagatcc tgcagaacgc cgaagagtac  1320
ctgcctttcc tgaagaacat cgacgaggaa tgcggcaaga ccgtgtccaa gaagatcatc  1380
gacctgttcg agttcagaat cccctactac gtgggccctc tgaataccgc caagggcgag  1440
aattgctgga tggttcgaaa agaggccggc agaatctacc cctggaactt cgatgagaag  1500
gtggacagag atcagagcgc cgagaagttc atcagacgga tgaccaacca gtgcacctac  1560
ctgatccacg aggacgtggt gcctaagaac agcctgctgt actccgagtt catggtgctg  1620
aacgagctga acaatgtgaa gattcggagc gagaagctgc ccgtggaact gaagcaggcc  1680
atcgtgctgg acctgtttaa gaagcagaag cagatcacag ggaagaagct gctcaactac  1740
ctgaacgcca acggctacga cgtgaagaaa gaggacctga gcggcttcga cggcaacttc  1800
aagtccagcc tgtccagcta cctgactctg aagaaggtgt tcggagagga actggacaag  1860
tacagcgtgc agcagatggc cgaggacatc atcctgtgga tcaccctgta tggcgacgat  1920
cagaaaatgc tgcggagagt gatccggaag cactacgagc agcagctgtc tgaggaacag  1980
atcctgagcc tgagcaagct gaagttccaa ggctggggca gactgtctag acggctgctc  2040
tctgaaatgg aaggcgtgga ctgtgaaacc ggcgagtgca tgacagtgat gcagggcctg  2100
agaaacaccc agaacaacct gatgcagctg ctgagccagc agttcagctt catggaactg  2160
atcgaggaag agaacgggaa ctactacgtc gacgagatca cctacgacaa cctggtcaag  2220
gacatggtca tcagccctag cgtgaaaagg gccgtgtggc agacagtgca gatcgtggaa  2280
gaaatcaagg gcgtgatggg atgccagcct aagaaaatct tcgtggaaat ggcccgcagc  2340
gacgaagaga agaaacggac cgtgtctcgg aaggatcggc tgctggaagc ctacgacgcc  2400
atcaaggatg aggcccggca atggcaagaa gaactgcaga aatactccga cggcgatttc  2460
aaggccatca agctgtacct gtactacacc cagatgggcc agtgcatgta caccggcaga  2520
aaaatcgatc tgtcccagct gaacgacgcc accgtgtggg atagagatca catctaccct  2580
cagagcaaga ccaaggacga cagcctggac aatctggtgc tggtggatag atccgtgaat  2640
gccaagaaaa gcgacggcat gctgagcccc gagatccagc agagaatgag agccacctgg  2700
aagtacctga aagaaaagaa gctcatcagc gagaagaagt acgagcggct gaccagagtg  2760
tcccctctga cagatgaaga actggccggc ttcatcaacc ggcagctggt ggaaacaaga  2820
cagagcagca aagccgtggc cacactgctg aagagggtgt acgatgaggc cgagattgtg  2880
tatgtgaagg ccgaggccgt gtctaacttc cggcgggata acctggacta catcaaagtg  2940
cgggacctga acgactacca ccacgccaag gacgcctacc agaacatcgt cgtgggcaac  3000
gtgttccacg agaagtttac cagcaatccc ctgcggtggc tgaaaaacaa ccccaacacc  3060
aagtactccc tcaaccagat gttcaacttc gacctggaaa agaacggcgt ggtcatctgg  3120
aagagaggca aggccggctc cattaagtgt gtggaagaga cactgaagcg gaacgacatc  3180
ctgttcacca gatacgcttt ctgcaacaaa ggcggcttct ttaatcagat gctgaccgcc  3240
gctccagagg ataagacaaa ggccaaaggc ctggtgccta tcaagaaagg catggaaacc  3300
tggaaatacg gcggctacac cagcgtgacc cctagccact ttatgctggt ggccagcaag  3360
gacaagaagg gaaaagagat ccggaccatc gagacagtgc ccctgtaccg gtggaaagag  3420
ttcaaagaga atcccgacgc tctgctccag tactgcagag agttctacgg cctgaaagag  3480
```

```
cccaaggttc tgatcccttg catcaagaag aatgcccggc tggtcgtgaa cggcttccct  3540
atgcacctga agggcagcac cggaaaacag ctgattctgc agggtgccgt gcagctgtgc  3600
ctgaacaacg agaacatcaa gtacctcaag aaagtgacga agtacctcga gtacaacgcc  3660
cagcggagag acaagagaac cctgctcgaa gttcgggaag tgaccggaat caacaaagag  3720
gaaaacatcc agctgtacga tgtgttcgtg gacaagctga gcaacacaat ctaccagtac  3780
agacccgcca atcctaagga caacctcatc aagggccgcg agaaattcat cgagcttggc  3840
ctggctgagc agtgcgtggt gctgggagaa gtgctgcatc tgttccagtg caagcccctg  3900
accagcgatc tgacactgat cggcggaagc cctaacaccg gcaccatcaa gatcaccaag  3960
accatcagca actgcaacgt ggtcaagctg ctgtcccagt ctatcgccgg cgtgaaagtc  4020
cgcgagatca acctgctgat catctga                                      4047

SEQ ID NO: 4           moltype = RNA  length = 17
FEATURE                Location/Qualifiers
misc_feature           1..17
                       note = sgRNA 12 crRNA repeat
source                 1..17
                       mol_type = other RNA
                       organism = synthetic construct
SEQUENCE: 4
gtttgagagt agtgtaa                                                 17

SEQ ID NO: 5           moltype = RNA  length = 15
FEATURE                Location/Qualifiers
misc_feature           1..15
                       note = sgRNA 12 Partial crRNA 1
source                 1..15
                       mol_type = other RNA
                       organism = synthetic construct
SEQUENCE: 5
gtttgagagt agtgt                                                   15

SEQ ID NO: 6           moltype = RNA  length = 12
FEATURE                Location/Qualifiers
misc_feature           1..12
                       note = sgRNA 12 Partial crRNA 2
source                 1..12
                       mol_type = other RNA
                       organism = synthetic construct
SEQUENCE: 6
gtttgagagt ag                                                      12

SEQ ID NO: 7           moltype = RNA  length = 10
FEATURE                Location/Qualifiers
misc_feature           1..10
                       note = sgRNA 12 Partial crRNA 3
source                 1..10
                       mol_type = other RNA
                       organism = synthetic construct
SEQUENCE: 7
gtttgagagt                                                         10

SEQ ID NO: 8           moltype = RNA  length = 19
FEATURE                Location/Qualifiers
misc_feature           1..19
                       note = sgRNA 12 tracrRNA antirepeat
source                 1..19
                       mol_type = other RNA
                       organism = synthetic construct
SEQUENCE: 8
ttacactaca agttcaaat                                               19

SEQ ID NO: 9           moltype = RNA  length = 17
FEATURE                Location/Qualifiers
misc_feature           1..17
                       note = sgRNA 12 partial tracrRNA 1
source                 1..17
                       mol_type = other RNA
                       organism = synthetic construct
SEQUENCE: 9
acactacaag ttcaaat                                                 17

SEQ ID NO: 10          moltype = RNA  length = 14
FEATURE                Location/Qualifiers
misc_feature           1..14
                       note = sgRNA 12 partial tracrRNA 2
source                 1..14
                       mol_type = other RNA
                       organism = synthetic construct
SEQUENCE: 10
```

```
ctacaagttc aaat                                                   14

SEQ ID NO: 11          moltype = RNA  length = 12
FEATURE                Location/Qualifiers
misc_feature           1..12
                       note = sgRNA 12 partial tracrRNA 3
source                 1..12
                       mol_type = other RNA
                       organism = synthetic construct
SEQUENCE: 11
acaagttcaa at                                                     12

SEQ ID NO: 12          moltype = RNA  length = 41
FEATURE                Location/Qualifiers
misc_feature           1..41
                       note = sgRNA 12 tracrRNA portion 1
source                 1..41
                       mol_type = other RNA
                       organism = synthetic construct
SEQUENCE: 12
aaaaatttat tcaaatcctt ttgctacatt gtgtagaatt t                     41

SEQ ID NO: 13          moltype = RNA  length = 26
FEATURE                Location/Qualifiers
misc_feature           1..26
                       note = sgRNA 12 tracrRNA portion 2
source                 1..26
                       mol_type = other RNA
                       organism = synthetic construct
SEQUENCE: 13
aaagatctgg caacagatct tttttt                                      26

SEQ ID NO: 14          moltype = RNA  length = 19
FEATURE                Location/Qualifiers
misc_feature           1..19
                       note = sgRNA 12 tracrRNA portion 2 polyT
source                 1..19
                       mol_type = other RNA
                       organism = synthetic construct
SEQUENCE: 14
aaagatctgg caacagatc                                              19

SEQ ID NO: 15          moltype = RNA  length = 107
FEATURE                Location/Qualifiers
misc_feature           1..107
                       note = sgRNA 12 V1
source                 1..107
                       mol_type = other RNA
                       organism = synthetic construct
SEQUENCE: 15
gtttgagagt agtgtaagaa attacactac aagttcaaat aaaaatttat tcaaatcctt  60
ttgctacatt gtgtagaatt taaagatctg gcaacagatc ttttttt               107

SEQ ID NO: 16          moltype = RNA  length = 107
FEATURE                Location/Qualifiers
misc_feature           1..107
                       note = sgRNA 12 V2
source                 1..107
                       mol_type = other RNA
                       organism = synthetic construct
SEQUENCE: 16
gtttgagagt agtgtaagaa attacactac aagttcaaat aaaaatttat tcaaatccat  60
ttgctacatt gtgtagaatt taaagatctg gcaacagatc ttttttt               107

SEQ ID NO: 17          moltype = RNA  length = 41
FEATURE                Location/Qualifiers
misc_feature           1..41
                       note = sgRNA 12 V2 Modified tracrRNA
source                 1..41
                       mol_type = other RNA
                       organism = synthetic construct
SEQUENCE: 17
aaaaatttat tcaaatccat ttgctacatt gtgtagaatt t                     41

SEQ ID NO: 18          moltype = RNA  length = 17
FEATURE                Location/Qualifiers
misc_feature           1..17
                       note = sgRNA 32 crRNA repeat
source                 1..17
```

```
                        mol_type = other RNA
                        organism = synthetic construct
SEQUENCE: 18
gtttgagagt agtgtaa                                                  17

SEQ ID NO: 19           moltype = RNA  length = 15
FEATURE                 Location/Qualifiers
misc_feature            1..15
                        note = sgRNA 32 Partial crRNA 1
source                  1..15
                        mol_type = other RNA
                        organism = synthetic construct
SEQUENCE: 19
gtttgagagt agtgt                                                    15

SEQ ID NO: 20           moltype = RNA  length = 12
FEATURE                 Location/Qualifiers
misc_feature            1..12
                        note = sgRNA 32 Partial crRNA 2
source                  1..12
                        mol_type = other RNA
                        organism = synthetic construct
SEQUENCE: 20
gtttgagagt ag                                                       12

SEQ ID NO: 21           moltype = RNA  length = 10
FEATURE                 Location/Qualifiers
misc_feature            1..10
                        note = sgRNA 32 Partial crRNA 3
source                  1..10
                        mol_type = other RNA
                        organism = synthetic construct
SEQUENCE: 21
gtttgagagt                                                          10

SEQ ID NO: 22           moltype = RNA  length = 19
FEATURE                 Location/Qualifiers
misc_feature            1..19
                        note = sgRNA 32 tracrRNA antirepeat
source                  1..19
                        mol_type = other RNA
                        organism = synthetic construct
SEQUENCE: 22
ttacactaca agttcaaat                                                19

SEQ ID NO: 23           moltype = RNA  length = 17
FEATURE                 Location/Qualifiers
misc_feature            1..17
                        note = sgRNA 32 Partial tracrRNA 1
source                  1..17
                        mol_type = other RNA
                        organism = synthetic construct
SEQUENCE: 23
acactacaag ttcaaat                                                  17

SEQ ID NO: 24           moltype = RNA  length = 14
FEATURE                 Location/Qualifiers
misc_feature            1..14
                        note = sgRNA 32 Partial tracrRNA 2
source                  1..14
                        mol_type = other RNA
                        organism = synthetic construct
SEQUENCE: 24
ctacaagttc aaat                                                     14

SEQ ID NO: 25           moltype = RNA  length = 12
FEATURE                 Location/Qualifiers
misc_feature            1..12
                        note = sgRNA 32 Partial tracrRNA 3
source                  1..12
                        mol_type = other RNA
                        organism = synthetic construct
SEQUENCE: 25
acaagttcaa at                                                       12

SEQ ID NO: 26           moltype = RNA  length = 41
FEATURE                 Location/Qualifiers
misc_feature            1..41
                        note = sgRNA 32 tracrRNA portion 1
```

```
source                  1..41
                        mol_type = other RNA
                        organism = synthetic construct
SEQUENCE: 26
aaaaatttat tcaaatcctt ttgctacatt gtgtagaatt t                   41

SEQ ID NO: 27           moltype = RNA  length = 32
FEATURE                 Location/Qualifiers
misc_feature            1..32
                        note = sgRNA 32 tracrRNA portion 2
source                  1..32
                        mol_type = other RNA
                        organism = synthetic construct
SEQUENCE: 27
aaagatctgg caacagatct tttttatttt tt                             32

SEQ ID NO: 28           moltype = RNA  length = 26
FEATURE                 Location/Qualifiers
misc_feature            1..26
                        note = sgRNA 32 tracrRNA portion 2 polyT
source                  1..26
                        mol_type = other RNA
                        organism = synthetic construct
SEQUENCE: 28
aaagatctgg caacagatct ttttta                                    26

SEQ ID NO: 29           moltype = RNA  length = 113
FEATURE                 Location/Qualifiers
misc_feature            1..113
                        note = sgRNA 32 V1
source                  1..113
                        mol_type = other RNA
                        organism = synthetic construct
SEQUENCE: 29
gtttgagagt agtgtaagaa attacactac aagttcaaat aaaaatttat tcaaatcctt  60
ttgctacatt gtgtagaatt taaagatctg gcaacagatc ttttttattt ttt         113

SEQ ID NO: 30           moltype = RNA  length = 106
FEATURE                 Location/Qualifiers
misc_feature            1..106
                        note = sgRNA 32 V2
source                  1..106
                        mol_type = other RNA
                        organism = synthetic construct
SEQUENCE: 30
gtttgagagt agtgtaagaa attacactac aagttcaaat aaaaatttat tcaaatcctt  60
ttgctacatt gtgtagaatt taaagatctg gcaacagatc tttttt                106

SEQ ID NO: 31           moltype = RNA  length = 106
FEATURE                 Location/Qualifiers
misc_feature            1..106
                        note = sgRNA 32 V3
source                  1..106
                        mol_type = other RNA
                        organism = synthetic construct
SEQUENCE: 31
gtttgagagt agtgtaagaa attacactac aagttcaaat aaaaatttat tcaaatccat  60
ttgctacatt gtgtagaatt taaagatctg gcaacagatc tttttt                106

SEQ ID NO: 32           moltype = RNA  length = 41
FEATURE                 Location/Qualifiers
misc_feature            1..41
                        note = sgRNA 32 V3 modified tracrRNA
source                  1..41
                        mol_type = other RNA
                        organism = synthetic construct
SEQUENCE: 32
aaaaatttat tcaaatccat ttgctacatt gtgtagaatt t                   41

SEQ ID NO: 33           moltype = RNA  length = 101
FEATURE                 Location/Qualifiers
misc_feature            1..101
                        note = V2.1
source                  1..101
                        mol_type = other RNA
                        organism = synthetic construct
SEQUENCE: 33
gtttgagagt agtggaaaca ctacaagttc aaataaaaat ttattcaaat ccatttgcta  60
cattgtgtag aatttaaaga tctggcaaca gatctttttt t                     101
```

```
SEQ ID NO: 34          moltype = RNA  length = 85
FEATURE                Location/Qualifiers
misc_feature           1..85
                       note = V2.2
source                 1..85
                       mol_type = other RNA
                       organism = synthetic construct
SEQUENCE: 34
gtttgagagt agtgtaagaa attacactac aagttcaaat aaaaatttat tcaaatccat  60
ttgctacatt gtgtagaatt ttttt                                        85

SEQ ID NO: 35          moltype = RNA  length = 79
FEATURE                Location/Qualifiers
misc_feature           1..79
                       note = V2.3
source                 1..79
                       mol_type = other RNA
                       organism = synthetic construct
SEQUENCE: 35
gtttgagagt agtggaaaca ctacaagttc aaataaaaat ttattcaaat ccatttgcta  60
cattgtgtag aatttttt                                                79

SEQ ID NO: 36          moltype = RNA  length = 95
FEATURE                Location/Qualifiers
misc_feature           1..95
                       note = V2.4
source                 1..95
                       mol_type = other RNA
                       organism = synthetic construct
SEQUENCE: 36
gtttgagagt agtggaaaca ctacaagttc aaataaaaat ttattcaaat ccatttgcta  60
cattgtgtag aatttaaaga tgcaaatctt ttttt                             95

SEQ ID NO: 37          moltype = DNA  length = 6373
FEATURE                Location/Qualifiers
misc_feature           1..6373
                       note = pET9a OMNI-103
source                 1..6373
                       mol_type = other DNA
                       organism = synthetic construct
SEQUENCE: 37
taatacgact cactataggg agaccacaac ggtttccctc tagagagaca ataaccctga  60
taatgcttca ataatattga aaaaggaaga gtatgcctaa gaagaagaga aaggtgggta  120
cctctatcaa gagcgactac ttcctgggcc tcgacatcgg cacagattct atcggatggg  180
ccgtgacaga ccccgagtac cacatcctga gaagaaaggg caaagccctg tggggcatca  240
gactgttcga tgccgccaat actgccgccg agagaagaac cttccggacc agcagaagaa  300
gaatccagcg gcggagacag cggatcagac tgctgcaaga gctgttcgcc gaggaaatgg  360
ttaagctgga ccccggcttc ttccagagac tgagcgatag cgccttctgg caagaggaca  420
agcaagagca gcagatctac agcctgttta cctgcgagaa ctacaccgac gtggactact  480
acagagagta ccccaccatc taccacctga gaagcgccct gatccaagag aaaaaagagt  540
tcgacctgcg gctgctgtat ctggccctgc accatctgat gaagcaccgg ggccactttc  600
tgttcaacgg cagcatcaac aacgtgacca gcttccacac caccttccag accttcgccg  660
actgcctgta cgacgagttc gacatcgagc tggaatgcga cagcgaggac agattcgccg  720
agatcctgaa ggataagcac gccagaaaga ccggcaagtg ctctgagctg gaaatcatct  780
gccacatcga gaagtccaac aagcagctga aagaactgtt caagctgatc accggcatga  840
aggccagcct gagcgtggtg tttggagatg atgagctggc cgagatcgag cacaacaaga  900
tcagcttcag cgagagcagc tacgacgaag tgcggctggc cctggaagat gagattcaag  960
agagaaccgg catcctggac atcttccacg ccgtgtattc ttgggccatc ctggccgata  1020
ttctggaagg cggcgagtac gagggcaaca gctatctgtc tgtggccaag gtgtccacct  1080
acaagaagca cggcgacgac ctgagactgc tgagaacact cgtgcgcgag tactgccccg  1140
accactacaa gagctttttc agcgtgtccg gcaaagagaa ctactgcgcc tacgccggca  1200
cactgaagaa gaacggcaag aagcagccca tcaagcggtg cagccaagag gacttctaca  1260
aggccctgaa gaaactgctg aaccagatgc ctaccgagca gcccgaagtg aaggatatct  1320
tcatcgagat tgagaacggc accttcctgc ctctgcaagt gtccaaggac aacggcgtga  1380
tcccctacca agtgaacaag atggaactcg agaagatcct gcagaacgcc gaagagtacc  1440
tgcctttcct gaagaacatc gacgaggaat gcggcaagac cgtgtccaag aagatcatcg  1500
acctgttcga gttcagaatc ccctactacg tgggccctct gaataccgcc aagggcgaga  1560
attgctggat ggttcgaaaa gaggccggca gaatctaccc ctggaacttc gatgagaagg  1620
tggacagaga tcagagcgcc gagaagttca tcagacggat gaccaaccag tgcacctacc  1680
tgatccacga ggacgtggtg cctaagaaca gcctgctgta ctccgagttc atggtgctga  1740
acgagctgaa caatgtgaag attcggagcg agaagctgcc cgtggaactg aagcaggcca  1800
tcgtgctgga cctgtttaag aagcagaagc agatcacagg gaagaagctg ctcaactacc  1860
tgaacgccaa cggctacgac gtgaagaaag aggacctgag cggcttcgac ggcaacttca  1920
agtccagcct gtccagctac ctgactctga agaaggtgtt cggagaggaa ctggacaagt  1980
acagcgtgca gcagatggcc gaggacatca tcctgtggat caccctgtat ggcgacgatc  2040
agaaaatgct gcggagagtg atccggaagc actacgagca gcagctgtct gaggaacaga  2100
tcctgagcct gagcaagctg aagttccaag gctggggcag actgtctaga cggctgctct  2160
ctgaaatgga aggcgtggac tgtgaaaccg gcgagtgcat gacagtgatg cagggcctga  2220
```

```
gaaacaccca gaacaacctg atgcagctgc tgagccagca gttcagcttc atggaactga  2280
tcgaggaaga gaacgggaac tactacgtcg acgagatcac ctacgacaac ctggtcaagg  2340
acatggtcat cagccctagc gtgaaaaggg ccgtgtggca gacagtgcag atcgtggaag  2400
aaatcaaggg cgtgatggga tgccagccta agaaaatctt cgtggaaatg gcccgcagcg  2460
acgaagagaa gaaacggacc gtgtctcgga aggatcggct gctggaagcc tacgacgcca  2520
tcaaggatga ggcccggcaa tggcaagaag aactgcagaa atactccgac ggcgatttca  2580
aggccatcaa gctgtacctg tactacaccc agatgggcca gtgcatgtac accggcagaa  2640
aaatcgatct gtcccagctg aacgacgcca ccgtgtggga tagagatcac atctaccctc  2700
agagcaagac caaggacgac agcctggaca atctggtgct ggtggataga tccgtgaatg  2760
ccaagaaaag cgacggcatg ctgagccccg agatccagca gagaatgaga gccacctgga  2820
agtacctgaa agaaaagaag ctcatcagcg agaagaagta cgagcggctg accagagtgt  2880
cccctctgac agatgaagaa ctggccggct tcatcaaccg gcagctggtg gaaacaagac  2940
agagcagcaa agccgtggcc acactgctga agagggtgta cgatgaggcc gagattgtgt  3000
atgtgaaggc cgaggccgtg tctaacttcc ggcgggataa cctggactac atcaaagtgc  3060
gggacctgaa cgactaccac cacgccaagg acgcctacca gaacatcgtc gtgggcaacg  3120
tgttccacga gaagtttacc agcaatcccc tgcggtggct gaaaaacaac ccccaacacca  3180
agtactccct caaccagatg ttcaacttcg acctggaaaa gaacggcgtg gtcatctgga  3240
agagaggcaa ggccggctcc attaagtgtg tggaagagac actgaagcgg aacgacatcc  3300
tgttcaccag atacgctttc tgcaacaaag gcggcttctt taatcagatg ctgaccgccg  3360
ctccagagga taagacaaag gccaaaggcc tggtgcctat caagaaaggc atggaaacct  3420
ggaaatacgg cggctacacc agcgtgaccc ctagccactt tatgctggtg gccagcaagg  3480
acaagaaggg aaaagagatc cggaccatcg agacagtgcc cctgtaccgg tggaaagagt  3540
tcaaagagaa tcccgacgct ctgctccagt actgcagaga gttctacggc ctgaaagagc  3600
ccaaggttct gatcccttgc atcaagaaga atgcccggct ggtcgtgaac ggcttcccta  3660
tgcacctgaa gggcagcacc ggaaaacagc tgattctgca gggtgccgtg cagctgtgcc  3720
tgaacaacga gaacatcaag tacctcaaga aagtgacgaa gtacctcgag tacaacgccc  3780
agcggagaga caagagaacc ctgctcgaag ttcgggaagt gaccggaatc aacaaagagg  3840
aaaacatcca gctgtacgat gtgttcgtgg acaagctgag caacacaatc taccagtaca  3900
gacccgccaa tcctaaggac aacctcatca agggccgcga gaaattcatc gagcttggcc  3960
tggctgagca gtgcgtggtg ctgggagaag tgctgcatct gttccagtgc aagcccctga  4020
ccagcgatct gacactgatc ggcggaagcc ctaacaccgg caccatcaag atcaccaaga  4080
ccatcagcaa ctgcaacgtg gtcaagctgc tgtcccagtc tatcgccggc gtgaaagtcc  4140
gcgagatcaa cctgctgatc atcggatcct acccatacga tgttccagat tacgcggccg  4200
ctccaaaaaa gaaaagaaaa gttgcggcta gccatcatca ccatcaccat catcattaag  4260
gctgctaaca aagcccgaaa ggaagctgag ttggctgctg ccaccgctga gcaataacta  4320
gcataacccc ttggggcctc taaacgggtc ttgaggggtt ttttgctgaa aggaggaact  4380
atatccggat atccacagga cgggtgtggt cgccatgatc gcgtagtcga tagtggctcc  4440
aagtagcgaa gcgagcagga ctgggcggcg gccaaagcgg tcggacagtg ctccgagaac  4500
gggtgcgcat agaaattgca tcaacgcata tagcgctagc agcacgccat agtgactggc  4560
gatgctgtcg gaatggacga tatcccgcaa gaggcccggc agtaccggca taaccaagcc  4620
tatgcctaca gcatccaggg tgacggtgcc gaggatgacg atgagcgcat tgttagattt  4680
catacacggt gcctgactgc gttagcaatt taactgtgat aaactaccgc attaaagctt  4740
atcgatgata agctgtcaaa catgagaatt cttagaaaaa ctcatcgagc atcaaatgaa  4800
actgcaattt attcatatca ggattatcaa taccatattt ttgaaaaagc cgtttctgta  4860
atgaaggaga aaactcaccg aggcagttcc ataggatggc aagatcctgg tatcggtctg  4920
cgattccgac tcgtccaaca tcaatacaac ctattaattt cccctcgtca aaaataaggt  4980
tatcaagtga gaaatcacca tgagtgacga ctgaatccgg tgagaatggc aaaagcttat  5040
gcatttcttt ccagacttgt tcaacaggcc agccattacg ctcgtcatca aaatcactcg  5100
catcaaccaa accgttattc attcgtgatt gcgcctgagc gagacgaaat acgcgatcgc  5160
tgttaaaagg acaattacaa acaggaatcg aatgcaaccg gcgcaggaac actgccagcg  5220
catcaacaat attttcacct gaatcaggat attcttctaa tacctggaat gctgttttcc  5280
cggggatcgc agtggtgagt aaccatgcat catcaggagt acggataaaa tgcttgatgg  5340
tcggaagagg cataaattcc gtcagccagt ttagtctgac catctcatct gtaacatcat  5400
tggcaacgct acctttgcca tgtttcagaa acaactctgg cgcatcgggc ttcccataca  5460
atcgatagat tgtcgcacct gattgcccga cattatcgcg agcccattta tacccatata  5520
aatcagcatc catgttggaa tttaatcgcg gcctcgagca agacgtttcc cgttgaatat  5580
ggctcataac accccttgta ttactgttta tgtaagcaga cagttttatt gttcatgacc  5640
aaaatccctt aacgtgagtt ttcgttccac tgagcgtcag accccgtaga aaagatcaaa  5700
ggatcttctt gagatccttt ttttctgcgc gtaatctgct gcttgcaaac aaaaaaacca  5760
ccgctaccag cggtggtttg tttgccggat caagagctac caactctttt tccgaaggta  5820
actggcttca gcagagcgca gataccaaat actgtccttc tagtgtagcc gtagttaggc  5880
caccacttca agaactctgt agcaccgcct acatacctcg ctctgctaat cctgttacca  5940
gtggctgctg ccagtggcga taagtcgtgt cttaccgggt tggactcaag acgatagtta  6000
ccggataagg cgcagcggtc gggctgaacg gggggttcgt gcacacagcc cagcttggag  6060
cgaacgacct acaccgaact gagataccta cagcgtgagc tatgagaaag cgccacgctt  6120
cccgaaggga gaaaggcgga caggtatccg gtaagcggca gggtcggaac aggagagcgc  6180
acgagggagc ttccaggggg aaacgcctgg tatctttata gtcctgtcgg gtttcgccac  6240
ctctgacttg agcgtcgatt tttgtgatgc tcgtcagggg ggcggagcct atggaaaaac  6300
gccagcaacg cggccttttt acggttcctg gccttttgct ggccttttgc tcacatgttc  6360
gatcccgcga aat                                                    6373
```

```
SEQ ID NO: 38          moltype = DNA  length = 2783
FEATURE                Location/Qualifiers
misc_feature           1..2783
                       note = pShuttle Guide OMNI-103 V2
source                 1..2783
                       mol_type = other DNA
                       organism = synthetic construct
SEQUENCE: 38
```

```
tacacggtgc ctgactgcgt tagcaattta actgtgataa actaccgcat taaagcttat  60
cgatgataag ctgtcaacac atttccccga aaagtgccac ctgacgtcct cgagtcccgc  120
ataatcgaaa tgagggccta tttcccatga ttccttcata tttgcatata cgatacaagg  180
ctgttagaga gataattaga attaatttga ctgtaaacac aaagatatta gtacaaaata  240
cgtgacgtag aaagtaataa tttcttgggt agtttgcagt tttaaaatta tgttttaaaa  300
tggactatca tatgcttacc gtaacttgaa agtatttcga tttcttggct ttatatatct  360
tgctaatacg actcactata ggaagagcag agccttggtc tcgtttgaga gtagtgtaag  420
aaattacact acaagttcaa ataaaaattt attcaaatcc atttgctaca ttgtgtagaa  480
tttaaagatc tggcaacaga tctttttttg aattctctag cataacccct tggggcctct  540
aaacgggtct tgaggggttt tttgacctag gctaggggat atattccggg taccccgctt  600
cctcgctcac tgactcgcta cgctcggtcg ttcgactgcg gcgagcggaa atggcttacg  660
aacggggcgg agatttcctg gaagatgcca ggaagatact taacagggaa gtgagagggc  720
cgcggcaaag ccgtttttcc ataggctccg ccccccctgac aagcatcacg aaatctgacg  780
ctcaaatcag tggtggcgaa acccgacagg actataaaga taccaggcgt ttccccctgg  840
cggctccctc gtgcgctctc ctgttcctgc ctttcggttt accggtgtca ttccgctgtt  900
atggccgcgt ttgtctcatt ccacgcctga cactcagttc cgggtaggca gttcgctcca  960
agctggactg tatgcacgaa ccccccgttc agtccgaccg ctgcgcctta tccggtaact  1020
atcgtcttga gtccaacccg gaaagacatg caaaagcacc actggcagca gccactggta  1080
attgatttag aggagttagt cttgaagtca tgcgccggtt aaggctaaac tgaaaggaca  1140
agttttggtg actgcgctcc tccaagccag ttacctcggt tcaaagagtt ggtagctcag  1200
agaaccttcg aaaaaccgcc ctgcaaggcg gttttttcgt tttcagagca agagattacg  1260
cgcagaccaa aacgatctca agaagatcat cttattaatc agataaaata tttctagatt  1320
tcagtgcaat ttatctcttc aaatgtagca cctgaagtca gccccatacg atataagttg  1380
ttactagtgc ttggattctc accaataaaa aacgcccggc ggcaaccgag cgttctgaac  1440
aaatccagat ggagttctga ggtcattact ggatctatca acaggagtcc aagcgagaag  1500
ggttggtttg cgcattcaca gttctccgca agaattgatt ggctccaatt cttggagtgg  1560
tgaatccgtt agcgaggtgc cgccggcttc cattcaggtc gaggtggccc ggctccatgc  1620
accgcgacgc aacgcgggga ggcagacaag gtatagggcg gcgcctacaa tccatgccaa  1680
cccgttccat gtgctcgccg aggcggcata aatcgccgtg acgatcagcg gtccaatgat  1740
cgaagttagg ctggtaagag ccgcgagcga tccttgaagc tgtccctgat ggtcgtcatc  1800
tacctgcctg gacagcatgg cctgcaacgc gggcatcccg atgccgccgg aagcgagaag  1860
aatcataatg gggaaggcca tccagcctcg cgtcgcgaac gccagcaaga cgtagcccag  1920
cgcgtcggcc gccatgccgg cgataatggc ctgcttctcg ccgaaacgtt tggtggcggg  1980
accagtgacg aaggcttgag cgagggcgtg caagattccg aataccgcaa gcgacaggcc  2040
gatcatcgtc gcgctccagc gaaagcggtc ctcgccgaaa atgacccaga gcgctgccgg  2100
cacctgtcct acgagttgca tgataaagaa gacagtcata agtgcggcga cgatagtcat  2160
gccccgcgcc caccggaagg agctgactgg gttgaaggct ctcaagggca tcggtcgacg  2220
ctctccctta tgcgactcct gcattaggaa gcagcccagt agtaggttga ggccgttgag  2280
caccgccgcc gcaaggaatg gtgcatgcaa ggagatggcg cccaacagtc ccccggccac  2340
ggggcctgcc accataccca cgccgaaaca agcgctcatg agcccgaagt ggcgagcccg  2400
atcttcccca tcggtgatgt cggcgatata ggcgccagca accgcacctg tggcgccggt  2460
gatgccggcc acgatgcgtc cggcgtagag gatccacagg acgggtgtgg tcgccatgat  2520
cgcgtagtcg atagtggctc caagtagcga agcgagcagg actgggcggc ggccaaagcg  2580
gtcggacagt gctccgagaa cgggtgcgca tagaaattgc atcaacgcat atagcgctag  2640
cagcacgcca tagtgactgg cgatgctgtc ggaatggacg atatcccgca agaggcccgg  2700
cagtaccggc ataaccaagc ctatgcctac agcatccagg gtgacggtgc cgaggatgac  2760
gatgagcgca ttgttagatt tca                                         2783
```

```
SEQ ID NO: 39           moltype = DNA  length = 5009
FEATURE                 Location/Qualifiers
misc_feature            1..5009
                        note = pbPOS T2 library
misc_feature            3040..3047
                        note = n is a, c, g, or t
source                  1..5009
                        mol_type = other DNA
                        organism = synthetic construct
SEQUENCE: 39
tcgagtcttt acactttatg cttccggctc gtatgttgtg tggaattgtg agcggataac  60
aatttcacac atgattacgg attcaacgtc gtgactggta aaacccgggc gttacccaac  120
ttaatcgcct tgcagcacat ccccctttcg ccagcaggcg taataaggaa aggattcatg  180
tactatttga aaaacacaaa cttttggatg ttcggtttat tctttttctt ttactttttt  240
atcatgggag cctacttccc gtttttcccg atttggctac atgatatcaa ccatatcagc  300
aaaagtgata cgggtattat ttttgccgct atttctctgt tctcgctatt attccaaccg  360
ctgtttggtc tgctttctga caaactcggt ctacgcaaat acctgctgtg gattattacc  420
ggcatgttag tgatgtttgc gccgttcttt atttttatct tcgggccact gctgcagtac  480
aacattttag tagggtcgat tgttggtggt atttatctag gctttagttt taacgccggt  540
gcgccagcag tagaggcatt tattgagaaa gtcagccggc gcagtaattt cgaatttggt  600
cgcgcgcgga tgtttggcag tgttggctgg gcgctggttg cctcgattgt cgggatcatg  660
ttcaccatta ataatcagtt tgttttctgg ctgggctctg gcagttgtct catcctcgcc  720
gttttactct ttttcgccaa aacggacgcg ccctcaagtg ccacggttgc caatgcggta  780
ggtgccaacc attcggcatt tagccttaag ctggcactgg aactgttcag acagccaaaa  840
ctgtggtttt tgtcactgta tgttattggc gtttcctcca cctacgatgt ttttgaccaa  900
cagtttgcta atttctttac ttcgttcttt gctaccggtg aacagggtac ccgcgtattt  960
ggctacgtaa cgacaatggg cgaattactt aacgcctcga ttatgttctt tgcgccactg  1020
atcattaatc gcatcggtgg gaagaatgcc ctgctgctgg ctggcactat tatgtctgta  1080
cgtattattg gctcatcgtt cgccacctca gcgctggaag tggttattct gaaaacgctg  1140
catatgtttg aagtaccgtt cctgctggtg ggctccttta aatatattac tagtcagttt  1200
gaagtgcgtt tttcagcgac gatttatctg gtcagtttca gcttctttaa gcaactggcg  1260
```

```
atgattttta tgtctgtact ggcgggcaat atgtatgaaa gcataggttt ccaaggcgct  1320
tatctggtgc tgggtctggt ggcgctgggc ttcaccttaa tttccgtgtt cacgcttagc  1380
ggcccgggcc cgctttccct gctgcgtcgt caggtgaatg aagtcgctta aaggcctcga  1440
tgcagctagc atgctaatct gattcgttac caattatgac aacttgacgg ctacatcatt  1500
cactttttct tcacaaccgg cacggaactc gctcgggctg gccccggtgc atttttttaaa  1560
tacccgcgag aaatagagtt gatcgtcaaa accaacattg cgaccgacgg tggcgatagg  1620
catccgggtg gtgctcaaaa gcagcttcgc ctggctgata cgttggtcct cgcgccagct  1680
taagacgcta atccctaact gctggcggaa aagatgtgac agacgcgacg gcgacaagca  1740
aacatgctgt gcgacgctgg cgatatcaaa attgctgtct gccaggtgat cgctgatgta  1800
ctgacaagcc tcgcgtaccc gattatccat cggtggatgg agcgactcgt taatcgcttc  1860
catgcgccgc agtaacaatt gctcaagcag atttatcgcc agcagctccg aatagcgccc  1920
ttccccttgc ccggcgttaa tgatttgccc aaacaggtcg ctgaaatgcg gctggtgcgc  1980
ttcatccggg cgaaagaacc ccgtattggc aaatattgac ggccagttaa gccattcatg  2040
ccagtaggcg cgcggacgaa agtaaaccca ctggtgatac cattcgcgag cctccggatg  2100
acgaccgtag tgatgaatct ctcctggcgg gaacagcaaa atatcacccg gtcggcaaac  2160
aaattctcgt ccctgatttt tcaccacccc ctgaccgcga atggtgagat tgagaatata  2220
acctttcatt cccagcggtc ggtcgataaa aaaatcgaga taaccgttgg cctcaatcgg  2280
cgttaaaccc gccaccagat gggcattaaa cgagtatccc ggcagcaggg gatcattttg  2340
cgcttcagcc atacttttca tactcccgcc attcagagaa gaaaccaatt gtccatattg  2400
catcagacat tgccgtcact gcgtctttta ctggctcttc tcgctaacca aaccggtaac  2460
cccgcttatt aaaagcattc tgtaacaaag cgggaccaaa gccatgacaa aaacgcgtaa  2520
caaaagtgtc tataatcacg gcagaaaagt ccacattgat tatttgcacg gcgtcacact  2580
ttgctatgcc atagcatttt tatccataag attagcggat cctacctgac gctttttatc  2640
gcaactctct actgtttctc catacccgtt tttttggggt agcgattgaa aacgatgcag  2700
tttaaggttt acacctataa aagagagagc cgttatcgtc tgtttgtgga tgtacagagt  2760
gatattattg acacgcccgg gcgacggatg gtgatccccc tggccagtgc acgtctgctg  2820
tcagataaag tctcccgtga actttacccg gtggtgcata tcggggatga aagctggcgc  2880
atgatgacca ccgatatggc cagtgtgccg gtctccgtta tcggggaaga agtggctgat  2940
ctcagccacc gcgaaaatga catcaaaaac gccattaacc tgatgttttg gggaatataa  3000
tcttctagac atacaatgga agagcagagc cttggtctcn nnnnnnnaag cttgatatcg  3060
aattcctgca gcccggggga tcccatggta cgcgtgctag aggcatcaaa taaaacgaaa  3120
ggctcagtcg aaagactggg cctttcgttt tatctgttgt ttgtcggtga acgctctcct  3180
gagtaggaca aatccgccgc cctagaccta ggcgttcggc tgcggcgagc ggtatcagct  3240
cactcaaagg cggtaatacg gttatccaca gaatcagggg ataacgcagg aaagaacatg  3300
tgagcaaaag gccagcaaaa ggccaggaac cgtaaaaagg ccgcgttgct ggcgtttttc  3360
cataggctcc gcccccctga cgagcatcac aaaaatcgac gctcaagtca gaggtggcga  3420
aacccgacag gactataaag ataccaggcg tttccccctg gaagctccct cgtgcgctct  3480
cctgttccga ccctgccgct taccggatac ctgtccgcct ttctcccttc gggaagcgtg  3540
gcgctttctc aatgctcacg ctgtaggtat ctcagttcgg tgtaggtcgt tcgctccaag  3600
ctgggctgtg tgcacgaacc ccccgttcag cccgaccgct gcgccttatc cggtaactat  3660
cgtcttgagt ccaacccggt aagacacgac ttatcgccac tggcagcagc cactggtaac  3720
aggattagca gagcgaggta tgtaggcggt gctacagagt tcttgaagtg gtggcctaac  3780
tacggctaca ctagaaggac agtatttggt atctgcgctc tgctgaagcc agttaccttc  3840
ggaaaaagag ttggtagctc ttgatccggc aaacaaacca ccgctggtag cggtggtttt  3900
tttgtttgca agcagcagat tacgcgcaga aaaaaaggat ctcaagaaga tcctttgatc  3960
ttttctacgg ggtctgacgc tcagtggaac gaaaactcac gttaagggat tttggtcatg  4020
actagtgctt ggattctcac caataaaaaa cgcccggcgg caaccgagcg ttctgaacaa  4080
atccagatgg agttctgagg tcattactgg atctatcaac aggagtccaa gcgagctcga  4140
tatcaaatta cgccccgccc tgccactcat cgcagtactg ttgtaattca ttaagcattc  4200
tgccgacatg gaagccatca cagacggcat gatgaacctg aatcgccagc ggcatcagca  4260
ccttgtcgcc ttgcgtataa tatttgccca tggtgaaaac gggggcgaag aagttgtcca  4320
tattggccac gtttaaatca aaactggtga aactcaccca gggattggct gagacgaaaa  4380
acatattctc aataaaccct ttagggaaat aggccaggtt ttcaccgtaa cacgccacat  4440
cttgcgaata tatgtgtaga aactgccgga aatcgtcgtg gtattcactc cagagcgatg  4500
aaaacgtttc agtttgctca tggaaaacgg tgtaacaagg gtgaacacta tcccatatca  4560
ccagctcacc gtctttcatt gccatacgga attccggatg agcattcatc aggcgggcaa  4620
gaatgtgaat aaaggccgga taaaacttgt gcttattttt ctttacggtc tttaaaaagg  4680
ccgtaatatc cagctgaacg gtctggttat aggtacattg agcaactgac tgaaatgcct  4740
caaaatgttc tttacgatgc cattgggata tatcaacggt ggtatatcca gtgatttttt  4800
tctccatttt agcttcctta gctcctgaaa atctcgataa ctcaaaaaat acgcccggta  4860
gtgatcttat ttcattatgg tgaaagttgg aacctcttac gtgccgatca acgtctcatt  4920
ttcgccagat atcgacgtct aagaaaccat tattatcatg acattaacct ataaaaatag  4980
gcgtatcacg aggccctttc gtcttcacc                                     5009
```

```
SEQ ID NO: 40          moltype = DNA  length = 10286
FEATURE                Location/Qualifiers
misc_feature           1..10286
                       note = pmOMNI OMNI-103
source                 1..10286
                       mol_type = other DNA
                       organism = synthetic construct
SEQUENCE: 40
gacggatcgg gagatctccc gatcccctat ggtgcactct cagtacaatc tgctctgatg  60
ccgcatagtt aagccagtat ctgctccctg cttgtgtgtt ggaggtcgct gagtagtgcg  120
cgagcaaaat ttaagctaca acaaggcaag gcttgaccga caattgcatg aagaatctgc  180
ttagggttag gcgttttgcg ctgcttcgcg atgtacgggc cagatatacg cgttgacatt  240
gattattgac tagttattaa tagtaatcaa ttacggggtc attagttcat agcccatata  300
tggagttccg cgttacataa cttacggtaa atggcccgcc tggctgaccg cccaacgacc  360
cccgcccatt gacgtcaata atgacgtatg ttcccatagt aacgccaata gggactttcc  420
```

```
attgacgtca atgggtggag tatttacggt aaactgccca cttggcagta catcaagtgt  480
atcatatgcc aagtacgccc cctattgacg tcaatgacgg taaatggccc gcctggcatt  540
atgcccagta catgacctta tgggactttc ctacttggca gtacatctac gtattagtca  600
tcgctattac catggtgatg cggttttggc agtacatcaa tgggcgtgga tagcggtttg  660
actcacgggg atttccaagt ctccacccca ttgacgtcaa tgggagtttg ttttggcacc  720
aaaatcaacg ggactttcca aaatgtcgta acaactccgc cccattgacg caaatgggcg  780
gtaggcgtgt acggtgggag gtctatataa gcagagctct ctggctaact agagaaccca  840
ctgcttactg gcttatcgaa attaatacga ctcactatag ggagacccaa gctggctagc  900
gtttaaactt aagcttgcca ccatgcctaa gaagaagaga aaggtgggta cctctatcaa  960
gagcgactac ttcctgggcc tcgacatcgg cacagattct atcggatggg ccgtgacaga  1020
ccccgagtac cacatcctga gaagaaaggg caaagccctg tggggcatca gactgttcga  1080
tgccgccaat actgccgccg agagaagaac cttccggacc agcagaagaa gaatccagcg  1140
gcggagacag cggatcagac tgctgcaaga gctgttcgcc gaggaaatgg ttaagctgga  1200
ccccggcttc ttccagagac tgagcgatag cgccttctgg caagaggaca agcaagagca  1260
gcagatctac agcctgttta cctgcgagaa ctacaccgac gtggactact acagagagta  1320
ccccaccatc taccacctga gaagcgccct gatccaagag aaaaaagagt tcgacctgcg  1380
gctgctgtat ctggccctgc accatctgat gaagcaccgg ggccactttc tgttcaacgg  1440
cagcatcaac aacgtgacca gcttccacac caccttccag accttcgccg actgcctgta  1500
cgacgagttc gacatcgagc tggaatgcga cagcgaggac agattcgccg agatcctgaa  1560
ggataagcac gccagaaaga ccggcaagtg ctctgagctg gaaatcatct gccacatcga  1620
gaagtccaac aagcagctga aagaactgtt caagctgatc accggcatga aggccagcct  1680
gagcgtggtg tttggagatg atgagctggc cgagatcgag cacaacaaga tcagcttcag  1740
cgagagcagc tacgacgaag tgcggctggc cctggaagat gagattcaag agagaaccgg  1800
catcctggac atcttccacg ccgtgtattc ttgggccatc ctggccgata ttctggaagg  1860
cggcgagtac gagggcaaca gctatctgtc tgtggccaag gtgtccacct acaagaagca  1920
cggcgacgac ctgagactgc tgagaacact cgtgcgcgag tactgccccg accactacaa  1980
gagctttttc agcgtgtccg gcaaagagaa ctactgcgcc tacgccggca cactgaagaa  2040
gaacggcaag aagcagccca tcaagcggtg cagccaagag gacttctaca aggccctgaa  2100
gaaactgctg aaccagatgc ctaccgagca gcccgaagtg aaggatatct tcatcgagat  2160
tgagaacggc accttcctgc ctctgcaagt gtccaaggac aacggcgtga tcccctacca  2220
agtgaacaag atggaactcg agaagatcct gcagaacgcc gaagagtacc tgcctttcct  2280
gaagaacatc gacgaggaat gcggcaagac cgtgtccaag aagatcatcg acctgttcga  2340
gttcagaatc ccctactacg tgggccctct gaataccgcc aagggcgaga attgctggat  2400
ggttcgaaaa gaggccggca gaatctaccc ctggaacttc gatgagaagg tggacagaga  2460
tcagagcgcc gagaagttca tcagacggat gaccaaccag tgcacctacc tgatccacga  2520
ggacgtggtg cctaagaaca gcctgctgta ctccgagttc atggtgctga acgagctgaa  2580
caatgtgaag attcggagcg agaagctgcc cgtggaactg aagcaggcca tcgtgctgga  2640
cctgtttaag aagcagaagc agatcacagg gaagaagctg ctcaactacc tgaacgccaa  2700
cggctacgac gtgaagaaag aggacctgag cggcttcgac ggcaacttca agtccagcct  2760
gtccagctac ctgactctga agaaggtgtt cggagaggaa ctggacaagt acagcgtgca  2820
gcagatggcc gaggacatca tcctgtggat caccctgtat ggcgacgatc agaaaatgct  2880
gcggagagtg atccggaagc actacgagca gcagctgtct gaggaacaga tcctgagcct  2940
gagcaagctg aagttccaag gctggggcag actgtctaga cggctgctct ctgaaatgga  3000
aggcgtggac tgtgaaaccg gcgagtgcat gacagtgatg cagggcctga gaaacaccca  3060
gaacaacctg atgcagctgc tgagccagca gttcagcttc atggaactga tcgaggaaga  3120
gaacgggaac tactacgtcg acgagatcac ctacgacaac ctggtcaagg acatggtcat  3180
cagccctagc gtgaaaaggg ccgtgtggca gacagtgcag atcgtggaag aaatcaaggg  3240
cgtgatggga tgccagccta agaaaatctt cgtggaaatg gcccgcagcg acgaagagaa  3300
gaaacggacc gtgtctcgga aggatcggct gctggaagcc tacgacgcca tcaaggatga  3360
ggcccggcaa tggcaagaag aactgcagaa atactccgac ggcgatttca aggccatcaa  3420
gctgtacctg tactacaccc agatgggcca gtgcatgtac accggcagaa aaatcgatct  3480
gtcccagctg aacgacgcca ccgtgtggga tagagatcac atctaccctc agagcaagac  3540
caaggacgac agcctggaca atctggtgct ggtggataga tccgtgaatg ccaagaaaag  3600
cgacggcatg ctgagccccg agatccagca gagaatgaga gccacctgga agtacctgaa  3660
agaaaagaag ctcatcagcg agaagaagta cgagcggctg accagagtgt cccctctgac  3720
agatgaagaa ctggccggct tcatcaaccg gcagctggtg gaaacaagac agagcagcaa  3780
agccgtggcc acactgctga agagggtgta cgatgaggcc gagattgtgt atgtgaaggc  3840
cgaggccgtg tctaacttcc ggcgggataa cctggactac atcaaagtgc gggacctgaa  3900
cgactaccac cacgccaagg acgcctacca gaacatcgtc gtgggcaacg tgttccacga  3960
gaagtttacc agcaatcccc tgcggtggct gaaaaacaac cccaacacca agtactccct  4020
caaccagatg ttcaacttcg acctggaaaa gaacggcgtg gtcatctgga agagaggcaa  4080
ggccggctcc attaagtgtg tggaagagac actgaagcgg aacgacatcc tgttcaccag  4140
atacgctttc tgcaacaaag gcggcttctt taatcagatg ctgaccgccg ctccagagga  4200
taagacaaag gccaaaggcc tggtgcctat caagaaaggc atggaaacct ggaaatacgg  4260
cggctacacc agcgtgaccc ctagccactt tatgctggtg gccagcaagg acaagaaggg  4320
aaaagagatc cggaccatcg agacagtgcc cctgtaccgg tggaaagagt tcaaagagaa  4380
tcccgacgct ctgctccagt actgcagaga gttctacggc ctgaaagagc ccaaggttct  4440
gatcccttgc atcaagaaga atgcccggct ggtcgtgaac ggcttcccta tgcacctgaa  4500
gggcagcacc ggaaaacagc tgattctgca gggtgccgtg cagctgtgcc tgaacaacga  4560
gaacatcaag tacctcaaga aagtgacgaa gtacctcgag tacaacgccc agcggagaga  4620
caagagaacc ctgctcgaag ttcgggaagt gaccggaatc aacaaagagg aaaacatcca  4680
gctgtacgat gtgttcgtgg acaagctgag caacacaatc taccagtaca gacccgccaa  4740
tcctaaggac aacctcatca agggccgcga gaaattcatc gagcttggcc tggctgagca  4800
gtgcgtggtg ctgggagaag tgctgcatct gttccagtgc aagcccctga ccagcgatct  4860
gacactgatc ggcggaagcc ctaacaccgg caccatcaag atcaccaaga ccatcagcaa  4920
ctgcaacgtg gtcaagctgc tgtcccagtc tatcgccggc gtgaaagtcc gcgagatcaa  4980
cctgctgatc atcggatcct acccatacga tgttccagat tacgcggccg ctccaaaaaa  5040
gaaaagaaaa gttgaattcg gcggcagcgg cgccaccaac ttcagcctgc tgaagcaggc  5100
cggcgacgtg gaggagaacc ccggccccat ggtgagcaag ggcgaggagg ataacatggc  5160
```

```
catcatcaag gagttcatgc gcttcaaggt gcacatggag ggctccgtga acggccacga  5220
gttcgagatc gagggcgagg gcgagggccg cccctacgag ggcacccaga ccgccaagct  5280
gaaggtgacc aagggtggcc ccctgccctt cgcctgggac atcctgtccc ctcagttcat  5340
gtacggctcc aaggcctacg tgaagcaccc cgccgacatc cccgactact tgaagctgtc  5400
cttccccgag ggcttcaagt gggagcgcgt gatgaacttc gaggacggcg gcgtggtgac  5460
cgtgacccag gactcctccc tgcaggacgg cgagttcatc tacaaggtga agctgcgcgg  5520
caccaacttc ccctccgacg gccccgtaat gcagaagaag accatgggct gggaggcctc  5580
ctccgagcgg atgtaccccg aggacggcgc cctgaagggc gagatcaagc agaggctgaa  5640
gctgaaggac ggcggccact acgacgctga ggtcaagacc acctacaagg ccaagaagcc  5700
cgtgcagctg cccggcgcct acaacgtcaa catcaagttg gacatcacct cccacaacga  5760
ggactacacc atcgtggaac agtacgaacg cgccgagggc cgccactcca ccggcggcat  5820
ggacgagctg tacaagtagc tcgagtctag agggcccgtt taaacccgct gatcagcctc  5880
gactgtgcct tctagttgcc agccatctgt tgtttgcccc tcccccgtgc cttccttgac  5940
cctggaaggt gccactccca ctgtcctttc ctaataaaat gaggaaattg catcgcattg  6000
tctgagtagg tgtcattcta ttctgggggg tggggtgggg caggacagca agggggagga  6060
ttgggaagac aatagcaggc atgctgggga tgcggtgggc tctatggctt ctgaggcgga  6120
aagaaccagc tggggctcta gggggtatcc ccacgcgccc tgtagcggcg cattaagcgc  6180
ggcgggtgtg gtggttacgc gcagcgtgac cgctacactt gccagcgccc tagcgcccgc  6240
tcctttcgct ttcttccctt cctttctcgc cacgttcgcc ggctttcccc gtcaagctct  6300
aaatcggggg ctccctttag ggttccgatt tagtgcttta cggcacctcg accccaaaaa  6360
acttgattag ggtgatggtt cacgtagtgg gccatcgccc tgatagacgg tttttcgccc  6420
tttgacgttg gagtccacgt tctttaatag tggactcttg ttccaaactg gaacaacact  6480
caaccctatc tcggtctatt cttttgattt ataagggatt ttgccgattt cggcctattg  6540
gttaaaaaat gagctgattt aacaaaaatt taacgcgaat taattctgtg gaatgtgtgt  6600
cagttagggt gtggaaagtc cccaggctcc ccagcaggca gaagtatgca aagcatgcat  6660
ctcaattagt cagcaaccag gtgtggaaag tccccaggct ccccagcagg cagaagtatg  6720
caaagcatgc atctcaatta gtcagcaacc atagtcccgc ccctaactcc gcccatcccg  6780
cccctaactc cgcccagttc cgcccattct ccgccccatg gctgactaat tttttttatt  6840
tatgcagagg ccgaggccgc ctctgcctct gagctattcc agaagtagtg aggaggcttt  6900
tttggaggcc taggcttttg caaaaagctc ccgggagctt gtatatccat tttcggatct  6960
gatcaagaga caggatgagg atcgtttcgc atgattgaac aagatggatt gcacgcaggt  7020
tctccggccg cttgggtgga gaggctattc ggctatgact gggcacaaca gacaatcggc  7080
tgctctgatg ccgccgtgtt ccggctgtca gcgcaggggc gcccggttct ttttgtcaag  7140
accgacctgt ccggtgccct gaatgaactg caggacgagg cagcgcggct atcgtggctg  7200
gccacgacgg gcgttccttg cgcagctgtg ctcgacgttg tcactgaagc gggaagggac  7260
tggctgctat tgggcgaagt gccggggcag gatctcctgt catctcacct tgctcctgcc  7320
gagaaagtat ccatcatggc tgatgcaatg cggcggctgc atacgcttga tccggctacc  7380
tgcccattcg accaccaagc gaaacatcgc atcgagcgag cacgtactcg gatggaagcc  7440
ggtcttgtcg atcaggatga tctggacgaa gagcatcagg ggctcgcgcc agccgaactg  7500
ttcgccaggc tcaaggcgcg catgcccgac ggcgaggatc tcgtcgtgac ccatggcgat  7560
gcctgcttgc cgaatatcat ggtggaaaat ggccgctttt ctggattcat cgactgtggc  7620
cggctgggtg tggcggaccg ctatcaggac atagcgttgg ctacccgtga tattgctgaa  7680
gagcttggcg gcgaatgggc tgaccgcttc ctcgtgcttt acggtatcgc cgctcccgat  7740
tcgcagcgca tcgccttcta tcgccttctt gacgagttct tctgagcggg actctggggt  7800
tcgaaatgac cgaccaagcg acgcccaacc tgccatcacg agatttcgat tccaccgccg  7860
ccttctatga aaggttgggc ttcggaatcg ttttccggga cgccggctgg atgatcctcc  7920
agcgcgggga tctcatgctg gagttcttcg cccaccccaa cttgtttatt gcagcttata  7980
atggttacaa ataaagcaat agcatcacaa atttcacaaa taaagcattt ttttcactgc  8040
attctagttg tggtttgtcc aaactcatca atgtatctta tcatgtctgt ataccgtcga  8100
cctctagcta gagcttggcg taatcatggt catagctgtt tcctgtgtga aattgttatc  8160
cgctcacaat tccacacaac atacgagccg gaagcataaa gtgtaaagcc tggggtgcct  8220
aatgagtgag ctaactcaca ttaattgcgt tgcgctcact gcccgctttc cagtcgggaa  8280
acctgtcgtg ccagctgcat taatgaatcg gccaacgcgc ggggagaggc ggtttgcgta  8340
ttgggcgctc ttccgcttcc tcgctcactg actcgctgcg ctcggtcgtt cggctgcggc  8400
gagcggtatc agctcactca aaggcggtaa tacggttatc cacagaatca ggggataacg  8460
caggaaagaa catgtgagca aaaggccagc aaaaggccag gaaccgtaaa aaggccgcgt  8520
tgctggcgtt tttccatagg ctccgccccc ctgacgagca tcacaaaaat cgacgctcaa  8580
gtcagaggtg gcgaaacccg acaggactat aaagatacca ggcgtttccc cctggaagct  8640
ccctcgtgcg ctctcctgtt ccgaccctgc cgcttaccgg atacctgtcc gcctttctcc  8700
cttcgggaag cgtggcgctt tctcatagct cacgctgtag gtatctcagt tcggtgtagg  8760
tcgttcgctc caagctgggc tgtgtgcacg aaccccccgt tcagcccgac cgctgcgcct  8820
tatccggtaa ctatcgtctt gagtccaacc cggtaagaca cgacttatcg ccactggcag  8880
cagccactgg taacaggatt agcagagcga ggtatgtagg cggtgctaca gagttcttga  8940
agtggtggcc taactacggc tacactagaa gaacagtatt tggtatctgc gctctgctga  9000
agccagttac cttcggaaaa agagttggta gctcttgatc cggcaaacaa accaccgctg  9060
gtagcggtgg tttttttgtt tgcaagcagc agattacgcg cagaaaaaaa ggatctcaag  9120
aagatccttt gatcttttct acggggtctg acgctcagtg gaacgaaaac tcacgttaag  9180
ggattttggt catgagatta tcaaaaagga tcttcaccta gatcctttta aattaaaaat  9240
gaagttttaa atcaatctaa agtatatatg agtaaacttg gtctgacagt taccaatgct  9300
taatcagtga ggcacctatc tcagcgatct gtctatttcg ttcatccata gttgcctgac  9360
tccccgtcgt gtagataact acgatacggg agggcttacc atctggcccc agtgctgcaa  9420
tgataccgcg agacccacgc tcaccggctc cagatttatc agcaataaac cagccagccg  9480
gaagggccga gcgcagaagt ggtcctgcaa ctttatccgc ctccatccag tctattaatt  9540
gttgccggga agctagagta agtagttcgc cagttaatag tttgcgcaac gttgttgcca  9600
ttgctacagg catcgtggtg tcacgctcgt cgtttggtat ggcttcattc agctccggtt  9660
cccaacgatc aaggcgagtt acatgatccc ccatgttgtg caaaaaagcg gttagctcct  9720
tcggtcctcc gatcgttgtc agaagtaagt tggccgcagt gttatcactc atggttatgg  9780
cagcactgca taattctctt actgtcatgc catccgtaag atgcttttct gtgactggtg  9840
agtactcaac caagtcattc tgagaatagt gtatgcggcg accgagttgc tcttgcccgg  9900
```

```
cgtcaatacg ggataatacc gcgccacata gcagaacttt aaaagtgctc atcattggaa  9960
aacgttcttc ggggcgaaaa ctctcaagga tcttaccgct gttgagatcc agttcgatgt  10020
aacccactcg tgcacccaac tgatcttcag catcttttac tttcaccagc gtttctgggt  10080
gagcaaaaac aggaaggcaa aatgccgcaa aaaagggaat aagggcgaca cggaaatgtt  10140
gaatactcat actcttcctt tttcaatatt attgaagcat ttatcagggt tattgtctca  10200
tgagcggata catatttgaa tgtatttaga aaaataaaca aataggggtt ccgcgcacat  10260
ttccccgaaa agtgccacct gacgtc                                       10286

SEQ ID NO: 41          moltype = AA  length = 9
FEATURE                Location/Qualifiers
REGION                 1..9
                       note = HA Tag amino acid sequence
source                 1..9
                       mol_type = protein
                       organism = synthetic construct
SEQUENCE: 41
YPYDVPDYA                                                          9

SEQ ID NO: 42          moltype = AA  length = 7
FEATURE                Location/Qualifiers
REGION                 1..7
                       note = SV40 NLS amino acid sequence
source                 1..7
                       mol_type = protein
                       organism = synthetic construct
SEQUENCE: 42
PKKKRKV                                                            7

SEQ ID NO: 43          moltype = AA  length = 19
FEATURE                Location/Qualifiers
REGION                 1..19
                       note = P2A amino acid sequence
source                 1..19
                       mol_type = protein
                       organism = synthetic construct
SEQUENCE: 43
ATNFSLLKQA GDVEENPGP                                               19

SEQ ID NO: 44          moltype = AA  length = 236
FEATURE                Location/Qualifiers
REGION                 1..236
                       note = mCherry amino acid sequence
source                 1..236
                       mol_type = protein
                       organism = synthetic construct
SEQUENCE: 44
MVSKGEEDNM AIIKEFMRFK VHMEGSVNGH EFEIEGEGEG RPYEGTQTAK LKVTKGGPLP  60
FAWDILSPQF MYGSKAYVKH PADIPDYLKL SFPEGFKWER VMNFEDGGVV TVTQDSSLQD  120
GEFIYKVKLR GTNFPSDGPV MQKKTMGWEA SSERMYPEDG ALKGEIKQRL KLKDGGHYDA  180
EVKTTYKAKK PVQLPGAYNV NIKLDITSHN EDYTIVEQYE RAEGRHSTGG MDELYK      236

SEQ ID NO: 45          moltype = DNA  length = 27
FEATURE                Location/Qualifiers
misc_feature           1..27
                       note = HA Tag DNA sequence
source                 1..27
                       mol_type = other DNA
                       organism = synthetic construct
SEQUENCE: 45
tacccatacg atgttccaga ttacgct                                      27

SEQ ID NO: 46          moltype = DNA  length = 21
FEATURE                Location/Qualifiers
misc_feature           1..21
                       note = SV40 NLS DNA sequence
source                 1..21
                       mol_type = other DNA
                       organism = synthetic construct
SEQUENCE: 46
ccaaaaaaga aaagaaaagt t                                            21

SEQ ID NO: 47          moltype = DNA  length = 57
FEATURE                Location/Qualifiers
misc_feature           1..57
                       note = P2A DNA sequence
source                 1..57
                       mol_type = other DNA
                       organism = synthetic construct
SEQUENCE: 47
```

```
gccaccaact tcagcctgct gaagcaggcc ggcgacgtgg aggagaaccc cggcccc     57

SEQ ID NO: 48          moltype = DNA  length = 711
FEATURE                Location/Qualifiers
misc_feature           1..711
                       note = mCherry DNA sequence
source                 1..711
                       mol_type = other DNA
                       organism = synthetic construct
SEQUENCE: 48
atggtgagca agggcgagga ggataacatg gccatcatca aggagttcat gcgcttcaag  60
gtgcacatgg agggctccgt gaacggccac gagttcgaga tcgagggcga gggcgagggc  120
cgcccctacg agggcaccca gaccgccaag ctgaaggtga ccaagggtgg ccccctgccc  180
ttcgcctggg acatcctgtc ccctcagttc atgtacggct ccaaggccta cgtgaagcac  240
cccgccgaca tccccgacta cttgaagctg tccttccccg agggcttcaa gtgggagcgc  300
gtgatgaact tcgaggacgg cggcgtggtg accgtgaccc aggactcctc cctgcaggac  360
ggcgagttca tctacaaggt gaagctgcgc ggcaccaact tcccctccga cggccccgta  420
atgcagaaga agaccatggg ctgggaggcc tcctccgagc ggatgtaccc cgaggacggc  480
gccctgaagg gcgagatcaa gcagaggctg aagctgaagg acggcggcca ctacgacgct  540
gaggtcaaga ccacctacaa ggccaagaag cccgtgcagc tgcccggcgc ctacaacgtc  600
aacatcaagt tggacatcac ctcccacaac gaggactaca ccatcgtgga acagtacgaa  660
cgcgccgagg gccgccactc caccggcggc atggacgagc tgtacaagta g           711

SEQ ID NO: 49          moltype = RNA  length = 22
FEATURE                Location/Qualifiers
misc_feature           1..22
                       note = OMNI-103_B2M_s11-ref
source                 1..22
                       mol_type = other RNA
                       organism = synthetic construct
SEQUENCE: 49
ggaccagagc gggagggtag ga                                           22

SEQ ID NO: 50          moltype = RNA  length = 22
FEATURE                Location/Qualifiers
misc_feature           1..22
                       note = OMNI-103_B2M_s12-ref
source                 1..22
                       mol_type = other RNA
                       organism = synthetic construct
SEQUENCE: 50
gtatgcctgc cgtgtgaacc at                                           22

SEQ ID NO: 51          moltype = RNA  length = 22
FEATURE                Location/Qualifiers
misc_feature           1..22
                       note = OMNI-103_B2M_S26 -ref
source                 1..22
                       mol_type = other RNA
                       organism = synthetic construct
SEQUENCE: 51
tctctctcca ttcttcagta ag                                           22

SEQ ID NO: 52          moltype = RNA  length = 22
FEATURE                Location/Qualifiers
misc_feature           1..22
                       note = OMNI-103_B2M_S27 -ref
source                 1..22
                       mol_type = other RNA
                       organism = synthetic construct
SEQUENCE: 52
agaattgaaa aagtggagca tt                                           22

SEQ ID NO: 53          moltype = RNA  length = 22
FEATURE                Location/Qualifiers
misc_feature           1..22
                       note = OMNI-103_B2M_S40 -ref
source                 1..22
                       mol_type = other RNA
                       organism = synthetic construct
SEQUENCE: 53
aagaatgtaa gacttacccc ac                                           22

SEQ ID NO: 54          moltype = RNA  length = 22
FEATURE                Location/Qualifiers
misc_feature           1..22
                       note = OMNI-103_B2M_S41 -ref
source                 1..22
                       mol_type = other RNA
```

```
                         organism = synthetic construct
SEQUENCE: 54
tcagcagctt acaaaagaat gt                                            22

SEQ ID NO: 55            moltype = RNA  length = 22
FEATURE                  Location/Qualifiers
misc_feature             1..22
                         note = OMNI-103_B2M_S48 -ref
source                   1..22
                         mol_type = other RNA
                         organism = synthetic construct
SEQUENCE: 55
cgtcgcgctg gcgggcattc ct                                            22

SEQ ID NO: 56            moltype = RNA  length = 22
FEATURE                  Location/Qualifiers
misc_feature             1..22
                         note = OMNI-103_B2M_S49 -ref
source                   1..22
                         mol_type = other RNA
                         organism = synthetic construct
SEQUENCE: 56
agacatctcg gcccgaatgc tg                                            22

SEQ ID NO: 57            moltype = RNA  length = 22
FEATURE                  Location/Qualifiers
misc_feature             1..22
                         note = OMNI-103_CXCR4_S35-ref
source                   1..22
                         mol_type = other RNA
                         organism = synthetic construct
SEQUENCE: 57
ctggagtgaa aacttgaaga ct                                            22

SEQ ID NO: 58            moltype = RNA  length = 22
FEATURE                  Location/Qualifiers
misc_feature             1..22
                         note = OMNI-103_CXCR4_s93-ref
source                   1..22
                         mol_type = other RNA
                         organism = synthetic construct
SEQUENCE: 58
ggggttcaga caacagtgga ag                                            22

SEQ ID NO: 59            moltype = RNA  length = 22
FEATURE                  Location/Qualifiers
misc_feature             1..22
                         note = OMNI-103_ELANE_g114-ref
source                   1..22
                         mol_type = other RNA
                         organism = synthetic construct
SEQUENCE: 59
ggtgttatgg tcacagcggg tg                                            22

SEQ ID NO: 60            moltype = RNA  length = 22
FEATURE                  Location/Qualifiers
misc_feature             1..22
                         note = OMNI-103_ELANE_g115-alt
source                   1..22
                         mol_type = other RNA
                         organism = synthetic construct
SEQUENCE: 60
tgggaatccc attcccgcag ct                                            22

SEQ ID NO: 61            moltype = RNA  length = 22
FEATURE                  Location/Qualifiers
misc_feature             1..22
                         note = OMNI-103_ELANE_g128-ref
source                   1..22
                         mol_type = other RNA
                         organism = synthetic construct
SEQUENCE: 61
tgctccccac ccgctcccag cc                                            22

SEQ ID NO: 62            moltype = RNA  length = 22
FEATURE                  Location/Qualifiers
misc_feature             1..22
                         note = OMNI-103_PDCD1_S40-ref
source                   1..22
```

```
                        mol_type = other RNA
                        organism = synthetic construct
SEQUENCE: 62
aacacatcgg agagcttcgt gc                                              22

SEQ ID NO: 63           moltype = RNA  length = 22
FEATURE                 Location/Qualifiers
misc_feature            1..22
                        note = OMNI-103_PDCD1_S92-ref
source                  1..22
                        mol_type = other RNA
                        organism = synthetic construct
SEQUENCE: 63
gaggaccgca gccagcccgg cc                                              22

SEQ ID NO: 64           moltype = RNA  length = 22
FEATURE                 Location/Qualifiers
misc_feature            1..22
                        note = OMNI-103_SAMD9_g34-ref
source                  1..22
                        mol_type = other RNA
                        organism = synthetic construct
SEQUENCE: 64
gccaagaccc tttaaacaga cc                                              22

SEQ ID NO: 65           moltype = RNA  length = 22
FEATURE                 Location/Qualifiers
misc_feature            1..22
                        note = OMNI-103_SAMD9_g36-ref
source                  1..22
                        mol_type = other RNA
                        organism = synthetic construct
SEQUENCE: 65
gtaataccag agtgaagatt at                                              22

SEQ ID NO: 66           moltype = RNA  length = 22
FEATURE                 Location/Qualifiers
misc_feature            1..22
                        note = OMNI-103_SAMD9L_g133-alt
source                  1..22
                        mol_type = other RNA
                        organism = synthetic construct
SEQUENCE: 66
aggaacaaag agcctttggt gc                                              22

SEQ ID NO: 67           moltype = RNA  length = 22
FEATURE                 Location/Qualifiers
misc_feature            1..22
                        note = OMNI-103_SAMD9L_g79-alt
source                  1..22
                        mol_type = other RNA
                        organism = synthetic construct
SEQUENCE: 67
tgacttctgt ctacgctaca ga                                              22

SEQ ID NO: 68           moltype = RNA  length = 22
FEATURE                 Location/Qualifiers
misc_feature            1..22
                        note = OMNI-103_SAMD9L_g80-alt
source                  1..22
                        mol_type = other RNA
                        organism = synthetic construct
SEQUENCE: 68
gcattctaga gcctggaatt ta                                              22

SEQ ID NO: 69           moltype = RNA  length = 22
FEATURE                 Location/Qualifiers
misc_feature            1..22
                        note = OMNI-103_SARM1_g42-ref
source                  1..22
                        mol_type = other RNA
                        organism = synthetic construct
SEQUENCE: 69
cgcgcggcct gcacacgcgt ct                                              22

SEQ ID NO: 70           moltype = RNA  length = 22
FEATURE                 Location/Qualifiers
misc_feature            1..22
                        note = OMNI-103_SARM1_g43-ref
```

```
source                  1..22
                        mol_type = other RNA
                        organism = synthetic construct
SEQUENCE: 70
cgccactgcg cgctggcgct gg                                           22

SEQ ID NO: 71           moltype = RNA  length = 22
FEATURE                 Location/Qualifiers
misc_feature            1..22
                        note = OMNI-103_SARM1_g44-ref
source                  1..22
                        mol_type = other RNA
                        organism = synthetic construct
SEQUENCE: 71
gtgtctgagc agcagctgct gg                                           22

SEQ ID NO: 72           moltype = RNA  length = 22
FEATURE                 Location/Qualifiers
misc_feature            1..22
                        note = OMNI-103_SARM1_g45-ref
source                  1..22
                        mol_type = other RNA
                        organism = synthetic construct
SEQUENCE: 72
gatgtcttca tcagctaccg cc                                           22

SEQ ID NO: 73           moltype = RNA  length = 22
FEATURE                 Location/Qualifiers
misc_feature            1..22
                        note = OMNI-103_TRAC_S124 -ref
source                  1..22
                        mol_type = other RNA
                        organism = synthetic construct
SEQUENCE: 73
tctcgaccag cttgacatca ca                                           22

SEQ ID NO: 74           moltype = RNA  length = 22
FEATURE                 Location/Qualifiers
misc_feature            1..22
                        note = OMNI-103_TRAC_S141 -ref
source                  1..22
                        mol_type = other RNA
                        organism = synthetic construct
SEQUENCE: 74
cttggtttta cagatacgaa cc                                           22

SEQ ID NO: 75           moltype = RNA  length = 22
FEATURE                 Location/Qualifiers
misc_feature            1..22
                        note = OMNI-103_TRAC_S142 -ref
source                  1..22
                        mol_type = other RNA
                        organism = synthetic construct
SEQUENCE: 75
cgtcatgagc agattaaacc cg                                           22

SEQ ID NO: 76           moltype = RNA  length = 22
FEATURE                 Location/Qualifiers
misc_feature            1..22
                        note = OMNI-103_TRAC_S24-ref
source                  1..22
                        mol_type = other RNA
                        organism = synthetic construct
SEQUENCE: 76
actgtgctag acatgaggtc ta                                           22

SEQ ID NO: 77           moltype = RNA  length = 22
FEATURE                 Location/Qualifiers
misc_feature            1..22
                        note = OMNI-103_TRAC_S35-ref
source                  1..22
                        mol_type = other RNA
                        organism = synthetic construct
SEQUENCE: 77
gaccctgccg tgtaccagct ga                                           22

SEQ ID NO: 78           moltype = RNA  length = 22
FEATURE                 Location/Qualifiers
misc_feature            1..22
```

```
                        note = OMNI-103_TRAC_S36-ref
source                  1..22
                        mol_type = other RNA
                        organism = synthetic construct
SEQUENCE: 78
tcaaaatcgg tgaataggca ga                                            22

SEQ ID NO: 79           moltype = RNA  length = 22
FEATURE                 Location/Qualifiers
misc_feature            1..22
                        note = OMNI-103_TRAC_S58-ref
source                  1..22
                        mol_type = other RNA
                        organism = synthetic construct
SEQUENCE: 79
agaaccctga ccctgccgtg ta                                            22

SEQ ID NO: 80           moltype = RNA  length = 22
FEATURE                 Location/Qualifiers
misc_feature            1..22
                        note = OMNI-103_TRAC_s90-ref
source                  1..22
                        mol_type = other RNA
                        organism = synthetic construct
SEQUENCE: 80
ttctgatgtg tatatcacag ac                                            22

SEQ ID NO: 81           moltype = RNA  length = 22
FEATURE                 Location/Qualifiers
misc_feature            1..22
                        note = OMNI-103_TRAC_S91-ref
source                  1..22
                        mol_type = other RNA
                        organism = synthetic construct
SEQUENCE: 81
gctgtggcct ggagcaacaa at                                            22

SEQ ID NO: 82           moltype = RNA  length = 22
FEATURE                 Location/Qualifiers
misc_feature            1..22
                        note = OMNI-103_B2M_S12 spacer
source                  1..22
                        mol_type = other RNA
                        organism = synthetic construct
SEQUENCE: 82
gtatgcctgc cgtgtgaacc at                                            22

SEQ ID NO: 83           moltype = RNA  length = 22
FEATURE                 Location/Qualifiers
misc_feature            1..22
                        note = OMNI-103_TRAC_S36 spacer
source                  1..22
                        mol_type = other RNA
                        organism = synthetic construct
SEQUENCE: 83
tcaaaatcgg tgaataggca ga                                            22

SEQ ID NO: 84           moltype = RNA  length = 22
FEATURE                 Location/Qualifiers
misc_feature            1..22
                        note = OMNI-103_TRAC_S35 spacer
source                  1..22
                        mol_type = other RNA
                        organism = synthetic construct
SEQUENCE: 84
gaccctgccg tgtaccagct ga                                            22

SEQ ID NO: 85           moltype = RNA  length = 25
FEATURE                 Location/Qualifiers
misc_feature            1..25
                        note = OMNI-103_PDCD1_S40 25nt spacer
source                  1..25
                        mol_type = other RNA
                        organism = synthetic construct
SEQUENCE: 85
tccaacacat cggagagctt cgtgc                                         25

SEQ ID NO: 86           moltype = RNA  length = 24
FEATURE                 Location/Qualifiers
```

```
misc_feature          1..24
                      note = OMNI-103_PDCD1_S40 24nt spacer
source                1..24
                      mol_type = other RNA
                      organism = synthetic construct
SEQUENCE: 86
ccaacacatc ggagagcttc gtgc                                        24

SEQ ID NO: 87         moltype = RNA  length = 23
FEATURE               Location/Qualifiers
misc_feature          1..23
                      note = OMNI-103_PDCD1_S40 23nt spacer
source                1..23
                      mol_type = other RNA
                      organism = synthetic construct
SEQUENCE: 87
caacacatcg gagagcttcg tgc                                         23

SEQ ID NO: 88         moltype = RNA  length = 22
FEATURE               Location/Qualifiers
misc_feature          1..22
                      note = OMNI-103_PDCD1_S40 22nt spacer
source                1..22
                      mol_type = other RNA
                      organism = synthetic construct
SEQUENCE: 88
aacacatcgg agagcttcgt gc                                          22

SEQ ID NO: 89         moltype = RNA  length = 21
FEATURE               Location/Qualifiers
misc_feature          1..21
                      note = OMNI-103_PDCD1_S40 21nt spacer
source                1..21
                      mol_type = other RNA
                      organism = synthetic construct
SEQUENCE: 89
acacatcgga gagcttcgtg c                                           21

SEQ ID NO: 90         moltype = RNA  length = 20
FEATURE               Location/Qualifiers
misc_feature          1..20
                      note = OMNI-103_PDCD1_S40 20nt spacer
source                1..20
                      mol_type = other RNA
                      organism = synthetic construct
SEQUENCE: 90
cacatcggag agcttcgtgc                                             20

SEQ ID NO: 91         moltype = RNA  length = 107
FEATURE               Location/Qualifiers
misc_feature          1..107
                      note = OMNI-103_B2M_S12 with sgRNA 12 V2 scaffold
source                1..107
                      mol_type = other RNA
                      organism = synthetic construct
SEQUENCE: 91
gtttgagagt agtgtaagaa attacactac aagttcaaat aaaaatttat tcaaatccat  60
ttgctacatt gtgtagaatt taaagatctg gcaacagatc ttttttt                107

SEQ ID NO: 92         moltype = RNA  length = 107
FEATURE               Location/Qualifiers
misc_feature          1..107
                      note = OMNI-103_TRAC_S36 with sgRNA 12 V2 scaffold
source                1..107
                      mol_type = other RNA
                      organism = synthetic construct
SEQUENCE: 92
gtttgagagt agtgtaagaa attacactac aagttcaaat aaaaatttat tcaaatccat  60
ttgctacatt gtgtagaatt taaagatctg gcaacagatc ttttttt                107

SEQ ID NO: 93         moltype = RNA  length = 107
FEATURE               Location/Qualifiers
misc_feature          1..107
                      note = OMNI-103_TRAC_S35 with sgRNA 12 V2 scaffold
source                1..107
                      mol_type = other RNA
                      organism = synthetic construct
SEQUENCE: 93
gtttgagagt agtgtaagaa attacactac aagttcaaat aaaaatttat tcaaatccat  60
```

```
ttgctacatt gtgtagaatt taaagatctg gcaacagatc ttttttt               107

SEQ ID NO: 94          moltype = RNA  length = 107
FEATURE                Location/Qualifiers
misc_feature           1..107
                       note = OMNI-103_PDCD1_S40 25nt with sgRNA 12 V2 scaffold
source                 1..107
                       mol_type = other RNA
                       organism = synthetic construct
SEQUENCE: 94
gtttgagagt agtgtaagaa attacactac aagttcaaat aaaaatttat tcaaatccat  60
ttgctacatt gtgtagaatt taaagatctg gcaacagatc ttttttt               107

SEQ ID NO: 95          moltype = RNA  length = 107
FEATURE                Location/Qualifiers
misc_feature           1..107
                       note = OMNI-103_PDCD1_S40 24nt with sgRNA 12 V2 scaffold
source                 1..107
                       mol_type = other RNA
                       organism = synthetic construct
SEQUENCE: 95
gtttgagagt agtgtaagaa attacactac aagttcaaat aaaaatttat tcaaatccat  60
ttgctacatt gtgtagaatt taaagatctg gcaacagatc ttttttt               107

SEQ ID NO: 96          moltype = RNA  length = 107
FEATURE                Location/Qualifiers
misc_feature           1..107
                       note = OMNI-103_PDCD1_S40 23nt with sgRNA 12 V2 scaffold
source                 1..107
                       mol_type = other RNA
                       organism = synthetic construct
SEQUENCE: 96
gtttgagagt agtgtaagaa attacactac aagttcaaat aaaaatttat tcaaatccat  60
ttgctacatt gtgtagaatt taaagatctg gcaacagatc ttttttt               107

SEQ ID NO: 97          moltype = RNA  length = 107
FEATURE                Location/Qualifiers
misc_feature           1..107
                       note = OMNI-103_PDCD1_S40 22nt with sgRNA 12 V2 scaffold
source                 1..107
                       mol_type = other RNA
                       organism = synthetic construct
SEQUENCE: 97
gtttgagagt agtgtaagaa attacactac aagttcaaat aaaaatttat tcaaatccat  60
ttgctacatt gtgtagaatt taaagatctg gcaacagatc ttttttt               107

SEQ ID NO: 98          moltype = RNA  length = 107
FEATURE                Location/Qualifiers
misc_feature           1..107
                       note = OMNI-103_PDCD1_S40 21nt with sgRNA 12 V2 scaffold
source                 1..107
                       mol_type = other RNA
                       organism = synthetic construct
SEQUENCE: 98
gtttgagagt agtgtaagaa attacactac aagttcaaat aaaaatttat tcaaatccat  60
ttgctacatt gtgtagaatt taaagatctg gcaacagatc ttttttt               107

SEQ ID NO: 99          moltype = RNA  length = 107
FEATURE                Location/Qualifiers
misc_feature           1..107
                       note = OMNI-103_PDCD1_S40 20nt with sgRNA 12 V2 scaffold
source                 1..107
                       mol_type = other RNA
                       organism = synthetic construct
SEQUENCE: 99
gtttgagagt agtgtaagaa attacactac aagttcaaat aaaaatttat tcaaatccat  60
ttgctacatt gtgtagaatt taaagatctg gcaacagatc ttttttt               107

SEQ ID NO: 100         moltype = RNA  length = 129
FEATURE                Location/Qualifiers
misc_feature           1..129
                       note = OMNI-103_B2M_S12 full sgRNA
source                 1..129
                       mol_type = other RNA
                       organism = synthetic construct
SEQUENCE: 100
gtatgcctgc cgtgtgaacc atgtttgaga gtagtgtaag aaattacact acaagttcaa  60
ataaaaattt attcaaatcc atttgctaca ttgtgtagaa tttaaagatc tggcaacaga  120
tcttttttt                                                         129
```

```
SEQ ID NO: 101          moltype = RNA  length = 129
FEATURE                 Location/Qualifiers
misc_feature            1..129
                        note = OMNI-103_TRAC_S36 full sgRNA
source                  1..129
                        mol_type = other RNA
                        organism = synthetic construct
SEQUENCE: 101
tcaaaatcgg tgaataggca gagtttgaga gtagtgtaag aaattacact acaagttcaa  60
ataaaaattt attcaaatcc atttgctaca ttgtgtagaa tttaaagatc tggcaacaga  120
tctttttt                                                           129

SEQ ID NO: 102          moltype = RNA  length = 129
FEATURE                 Location/Qualifiers
misc_feature            1..129
                        note = OMNI-103_TRAC_S35 full sgRNA
source                  1..129
                        mol_type = other RNA
                        organism = synthetic construct
SEQUENCE: 102
gaccctgccg tgtaccagct gagtttgaga gtagtgtaag aaattacact acaagttcaa  60
ataaaaattt attcaaatcc atttgctaca ttgtgtagaa tttaaagatc tggcaacaga  120
tctttttt                                                           129

SEQ ID NO: 103          moltype = RNA  length = 132
FEATURE                 Location/Qualifiers
misc_feature            1..132
                        note = OMNI-103_PDCD1_S40 25nt full sgRNA
source                  1..132
                        mol_type = other RNA
                        organism = synthetic construct
SEQUENCE: 103
tccaacacat cggagagctt cgtgcgtttg agagtagtgt aagaaattac actacaagtt  60
caaataaaaa tttattcaaa tccatttgct acattgtgta gaatttaaag atctggcaac  120
agatcttttt tt                                                      132

SEQ ID NO: 104          moltype = RNA  length = 131
FEATURE                 Location/Qualifiers
misc_feature            1..131
                        note = OMNI-103_PDCD1_S40 24nt full sgRNA
source                  1..131
                        mol_type = other RNA
                        organism = synthetic construct
SEQUENCE: 104
ccaacacatc ggagagcttc gtgcgtttga gagtagtgta agaaattaca ctacaagttc  60
aaataaaaat ttattcaaat ccatttgcta cattgtgtag aatttaaaga tctggcaaca  120
gatcttttt t                                                        131

SEQ ID NO: 105          moltype = RNA  length = 130
FEATURE                 Location/Qualifiers
misc_feature            1..130
                        note = OMNI-103_PDCD1_S40 23nt full sgRNA
source                  1..130
                        mol_type = other RNA
                        organism = synthetic construct
SEQUENCE: 105
caacacatcg gagagcttcg tgcgtttgag agtagtgtaa gaaattacac tacaagttca  60
aataaaaatt tattcaaatc catttgctac attgtgtaga atttaaagat ctggcaacag  120
atcttttttt                                                         130

SEQ ID NO: 106          moltype = RNA  length = 129
FEATURE                 Location/Qualifiers
misc_feature            1..129
                        note = OMNI-103_PDCD1_S40 22nt full sgRNA
source                  1..129
                        mol_type = other RNA
                        organism = synthetic construct
SEQUENCE: 106
aacacatcgg agagcttcgt gcgtttgaga gtagtgtaag aaattacact acaagttcaa  60
ataaaaattt attcaaatcc atttgctaca ttgtgtagaa tttaaagatc tggcaacaga  120
tctttttt                                                           129

SEQ ID NO: 107          moltype = RNA  length = 128
FEATURE                 Location/Qualifiers
misc_feature            1..128
                        note = OMNI-103_PDCD1_S40 21nt full sgRNA
source                  1..128
                        mol_type = other RNA
```

```
                         organism = synthetic construct
SEQUENCE: 107
acacatcgga gagcttcgtg cgtttgagag tagtgtaaga aattacacta caagttcaaa  60
taaaaattta ttcaaatcca tttgctacat tgtgtagaat ttaaagatct ggcaacagat  120
ctttttt                                                             128

SEQ ID NO: 108           moltype = RNA  length = 127
FEATURE                  Location/Qualifiers
misc_feature             1..127
                         note = OMNI-103_PDCD1_S40 20nt full sgRNA
source                   1..127
                         mol_type = other RNA
                         organism = synthetic construct
SEQUENCE: 108
cacatcggag agcttcgtgc gtttgagagt agtgtaagaa attacactac aagttcaaat  60
aaaaatttat tcaaatccat ttgctacatt gtgtagaatt taaagatctg gcaacagatc  120
ttttttt                                                             127

SEQ ID NO: 109           moltype = RNA  length = 101
FEATURE                  Location/Qualifiers
misc_feature             1..101
                         note = V2.1 scaffold
source                   1..101
                         mol_type = other RNA
                         organism = synthetic construct
SEQUENCE: 109
gtttgagagt agtggaaaca ctacaagttc aaataaaaat ttattcaaat ccatttgcta  60
cattgtgtag aatttaaaga tctggcaaca gatctttttt t                       101

SEQ ID NO: 110           moltype = RNA  length = 85
FEATURE                  Location/Qualifiers
misc_feature             1..85
                         note = V2.2 scaffold
source                   1..85
                         mol_type = other RNA
                         organism = synthetic construct
SEQUENCE: 110
gtttgagagt agtgtaagaa attacactac aagttcaaat aaaaatttat tcaaatccat  60
ttgctacatt gtgtagaatt ttttt                                         85

SEQ ID NO: 111           moltype = RNA  length = 79
FEATURE                  Location/Qualifiers
misc_feature             1..79
                         note = V2.3 scaffold
source                   1..79
                         mol_type = other RNA
                         organism = synthetic construct
SEQUENCE: 111
gtttgagagt agtggaaaca ctacaagttc aaataaaaat ttattcaaat ccatttgcta  60
cattgtgtag aattttttt                                                79

SEQ ID NO: 112           moltype = RNA  length = 95
FEATURE                  Location/Qualifiers
misc_feature             1..95
                         note = V2.4 scaffold
source                   1..95
                         mol_type = other RNA
                         organism = synthetic construct
SEQUENCE: 112
gtttgagagt agtggaaaca ctacaagttc aaataaaaat ttattcaaat ccatttgcta  60
cattgtgtag aatttaaaga tgcaaatctt ttttt                              95

SEQ ID NO: 113           moltype = RNA  length = 101
FEATURE                  Location/Qualifiers
misc_feature             1..101
                         note = V2.5 scaffold
source                   1..101
                         mol_type = other RNA
                         organism = synthetic construct
SEQUENCE: 113
gtttgagagt agtgtaagaa attacactac aagttcaaat aaaaatttat tcaaatccat  60
ttgctacatt gtgtagaatt taaagatgca aatctttttt t                       101

SEQ ID NO: 114           moltype = RNA  length = 14
FEATURE                  Location/Qualifiers
misc_feature             1..14
                         note = crRNA Repeat sequence A
source                   1..14
                         mol_type = other RNA
```

```
                        organism = synthetic construct
SEQUENCE: 114
gtttgagagt agtg                                                 14

SEQ ID NO: 115          moltype = RNA  length = 17
FEATURE                 Location/Qualifiers
misc_feature            1..17
                        note = crRNA Repeat sequence B
source                  1..17
                        mol_type = other RNA
                        organism = synthetic construct
SEQUENCE: 115
gtttgagagt agtgtaa                                              17

SEQ ID NO: 116          moltype = RNA  length = 16
FEATURE                 Location/Qualifiers
misc_feature            1..16
                        note = tracrRNA antiepeat sequence A
source                  1..16
                        mol_type = other RNA
                        organism = synthetic construct
SEQUENCE: 116
cactacaagt tcaaat                                               16

SEQ ID NO: 117          moltype = RNA  length = 19
FEATURE                 Location/Qualifiers
misc_feature            1..19
                        note = tracrRNA antiepeat sequence B
source                  1..19
                        mol_type = other RNA
                        organism = synthetic construct
SEQUENCE: 117
ttacactaca agttcaaat                                            19

SEQ ID NO: 118          moltype = RNA  length = 41
FEATURE                 Location/Qualifiers
misc_feature            1..41
                        note = tracrRNA Portion 1 sequence A
source                  1..41
                        mol_type = other RNA
                        organism = synthetic construct
SEQUENCE: 118
aaaaatttat tcaaatccat ttgctacatt gtgtagaatt t                   41

SEQ ID NO: 119          moltype = RNA  length = 45
FEATURE                 Location/Qualifiers
misc_feature            1..45
                        note = tracrRNA Portion 1 sequence B
source                  1..45
                        mol_type = other RNA
                        organism = synthetic construct
SEQUENCE: 119
aaaaatttat tcaaatccat ttgctacatt gtgtagaatt ttttt               45

SEQ ID NO: 120          moltype = RNA  length = 38
FEATURE                 Location/Qualifiers
misc_feature            1..38
                        note = tracrRNA Portion 1 partial sequence
source                  1..38
                        mol_type = other RNA
                        organism = synthetic construct
SEQUENCE: 120
aaaaatttat tcaaatccat ttgctacatt gtgtagaa                       38

SEQ ID NO: 121          moltype = RNA  length = 26
FEATURE                 Location/Qualifiers
misc_feature            1..26
                        note = tracrRNA Portion 2 sequence A
source                  1..26
                        mol_type = other RNA
                        organism = synthetic construct
SEQUENCE: 121
aaagatctgg caacagatct tttttt                                    26

SEQ ID NO: 122          moltype = RNA  length = 20
FEATURE                 Location/Qualifiers
misc_feature            1..20
                        note = tracrRNA Portion 2 sequence B
source                  1..20
```

```
                         mol_type = other RNA
                         organism = synthetic construct
SEQUENCE: 122
aaagatgcaa atcttttttt                                          20

SEQ ID NO: 123           moltype = RNA  length = 17
FEATURE                  Location/Qualifiers
misc_feature             1..17
                         note = tracrRNA Portion 2 - partial sequence A
source                   1..17
                         mol_type = other RNA
                         organism = synthetic construct
SEQUENCE: 123
aaagatctgg caacaga                                             17

SEQ ID NO: 124           moltype = RNA  length = 13
FEATURE                  Location/Qualifiers
misc_feature             1..13
                         note = tracrRNA Portion 2 - partial sequence B
source                   1..13
                         mol_type = other RNA
                         organism = synthetic construct
SEQUENCE: 124
aaagatgcaa atc                                                 13

SEQ ID NO: 125           moltype = RNA  length = 22
FEATURE                  Location/Qualifiers
misc_feature             1..22
                         note = TRAC s91 spacer
source                   1..22
                         mol_type = other RNA
                         organism = synthetic construct
SEQUENCE: 125
gctgtggcct ggagcaacaa at                                       22

SEQ ID NO: 126           moltype = RNA  length = 22
FEATURE                  Location/Qualifiers
misc_feature             1..22
                         note = PDCD1 s40 spacer
source                   1..22
                         mol_type = other RNA
                         organism = synthetic construct
SEQUENCE: 126
aacacatcgg agagcttcgt gc                                       22

SEQ ID NO: 127           moltype = RNA  length = 22
FEATURE                  Location/Qualifiers
misc_feature             1..22
                         note = B2M s12 spacer
source                   1..22
                         mol_type = other RNA
                         organism = synthetic construct
SEQUENCE: 127
gtatgcctgc cgtgtgaacc at                                       22

SEQ ID NO: 128           moltype = RNA  length = 22
FEATURE                  Location/Qualifiers
misc_feature             1..22
                         note = TRAC s35 spacer
source                   1..22
                         mol_type = other RNA
                         organism = synthetic construct
SEQUENCE: 128
gaccctgccg tgtaccagct ga                                       22

SEQ ID NO: 129           moltype = RNA  length = 107
FEATURE                  Location/Qualifiers
misc_feature             1..107
                         note = OMNI-103 v2.2 TRAC S35 sgRNA
source                   1..107
                         mol_type = other RNA
                         organism = synthetic construct
```

```
SEQUENCE: 129
gaccctgccg tgtaccagct gagtttgaga gtagtgtaag aaattacact acaagttcaa  60
ataaaaattt attcaaatcc atttgctaca ttgtgtagaa ttttttt               107

SEQ ID NO: 130          moltype = RNA  length = 101
FEATURE                 Location/Qualifiers
misc_feature            1..101
                        note = OMNI-103 v2.3 TRAC S35 sgRNA
source                  1..101
                        mol_type = other RNA
                        organism = synthetic construct
SEQUENCE: 130
gaccctgccg tgtaccagct gagtttgaga gtagtggaaa cactacaagt tcaaataaaa  60
atttattcaa atccatttgc tacattgtgt agaatttttt t                     101

SEQ ID NO: 131          moltype = RNA  length = 107
FEATURE                 Location/Qualifiers
misc_feature            1..107
                        note = OMNI-103 v2.2 B2M S12 sgRNA
source                  1..107
                        mol_type = other RNA
                        organism = synthetic construct
SEQUENCE: 131
gtatgcctgc cgtgtgaacc atgtttgaga gtagtgtaag aaattacact acaagttcaa  60
ataaaaattt attcaaatcc atttgctaca ttgtgtagaa ttttttt               107

SEQ ID NO: 132          moltype = RNA  length = 101
FEATURE                 Location/Qualifiers
misc_feature            1..101
                        note = OMNI-103 v2.3 B2M S12 sgRNA
source                  1..101
                        mol_type = other RNA
                        organism = synthetic construct
SEQUENCE: 132
gtatgcctgc cgtgtgaacc atgtttgaga gtagtggaaa cactacaagt tcaaataaaa  60
atttattcaa atccatttgc tacattgtgt agaatttttt t                     101

SEQ ID NO: 133          moltype = DNA  length = 28
FEATURE                 Location/Qualifiers
misc_feature            1..28
                        note = PDCD1 S40 site
misc_feature            23..24
                        note = n is a, c, g, or t
source                  1..28
                        mol_type = other DNA
                        organism = synthetic construct
SEQUENCE: 133
gaccctgccg tgtaccagct gannract                                    28

SEQ ID NO: 134          moltype = DNA  length = 28
FEATURE                 Location/Qualifiers
misc_feature            1..28
                        note = TRAC S35 site
misc_feature            23..24
                        note = n is a, c, g, or t
source                  1..28
                        mol_type = other DNA
                        organism = synthetic construct
SEQUENCE: 134
aacacatcgg agagcttcgt gcnnract                                    28

SEQ ID NO: 135          moltype = DNA  length = 22
FEATURE                 Location/Qualifiers
misc_feature            1..22
                        note = T2 sequence
source                  1..22
                        mol_type = other DNA
                        organism = synthetic construct
SEQUENCE: 135
ggaagagcag agccttggtc tc                                          22
```

OMNI-103 CRISPR NUCLEASE

This application is a continuation of U.S. patent application Ser. No. 18/006,362 filed on Jan. 20, 2023, which is a § 371 national stage of PCT International Application No. PCT/US2022/015504, filed Feb. 7, 2022, claiming the benefit of U.S. Provisional Application No. 63/286,855, filed Dec. 9, 2021, U.S. Provisional Application No. 63/214,506, filed Jun. 24, 2021, and U.S. Provisional Application No. 63/147,166, filed Feb. 8, 2021, the contents of each of which are hereby incorporated by reference into the subject application.

Throughout this application, various publications are referenced, including referenced in parenthesis. The disclosures of all publications mentioned in this application in their entireties are hereby incorporated by reference into this application in order to provide additional description of the art to which this invention pertains and of the features in the art which can be employed with this invention.

REFERENCE TO SEQUENCE LISTING

This application incorporates-by-reference amino acid and nucleotide sequences which are present in the file named "5798_0041US03_OMNI_103_CON.xml", which is ~211,733 bytes in size, and created on Oct. 30, 2024, in the IBM-PC machine format, having an operating system compatibility with MS-Windows, which is contained in the .xml-file filed Oct. 31, 2024, as part of this application.

FIELD OF THE INVENTION

The present invention is directed to, inter alia, composition and methods for genome editing.

BACKGROUND OF THE INVENTION

The Clustered Regularly Interspaced Short Palindromic Repeat (CRISPR) systems of bacterial and archaeal adaptive immunity show extreme diversity of protein composition and genomic loci architecture. The CRISPR systems have become important tools for research and genome engineering. Nevertheless, many details of CRISPR systems have not been determined and the applicability of CRISPR nucleases may be limited by sequence specificity requirements, expression, or delivery challenges. Different CRISPR nucleases have diverse characteristics such as: size, PAM site, on target activity, specificity, cleavage pattern (e.g. blunt, staggered ends), and prominent pattern of indel formation following cleavage. Different sets of characteristics may be useful for different applications. For example, some CRISPR nucleases may be able to target particular genomic loci that other CRISPR nucleases cannot due to limitations of the PAM site. In addition, some CRISPR nucleases currently in use exhibit pre-immunity, which may limit in vivo applicability. See Charlesworth et al., Nature Medicine (2019) and Wagner et al., Nature Medicine (2019). Accordingly, discovery, engineering, and improvement of novel CRISPR nucleases is of importance.

SUMMARY OF THE INVENTION

Disclosed herein are compositions and methods that may be utilized for genomic engineering, epigenomic engineering, genome targeting, genome editing of cells, and/or in vitro diagnostics.

The disclosed compositions may be utilized for modifying genomic DNA sequences. As used herein, genomic DNA refers to linear and/or chromosomal DNA and/or plasmid or other extrachromosomal DNA sequences present in the cell or cells of interest. In some embodiments, the cell of interest is a eukaryotic cell. In some embodiments, the cell of interest is a prokaryotic cell. In some embodiments, the methods produce double-stranded breaks (DSBs) at predetermined target sites in a genomic DNA sequence, resulting in mutation, insertion, and/or deletion of a DNA sequence at the target site(s) in a genome.

Accordingly, in some embodiments, the compositions comprise a Clustered Regularly Interspaced Short Palindromic Repeat (CRISPR) nucleases. In some embodiments, the CRISPR nuclease is a CRISPR-associated protein.

OMNI-103 CRISPR Nuclease

Embodiments of the present invention provide for CRISPR nucleases designated as an "OMNI-103" nuclease as provided in Table 1.

This invention provides a method of modifying a nucleotide sequence at a target site in the genome of a mammalian cell comprising introducing into the cell (i) a composition comprising a CRISPR nuclease having at least 95% identity to the amino acid sequence of SEQ ID NO: 1 or a nucleic acid molecule comprising a sequence encoding a CRISPR nuclease which sequence has at least 95% identity to the nucleic acid sequence of SEQ ID NOs: 2-3 and (ii) a DNA-targeting RNA molecule, or a DNA polynucleotide encoding a DNA-targeting RNA molecule, comprising a nucleotide sequence that is complementary to a sequence in the target DNA.

This invention also provides a non-naturally occurring composition comprising a CRISPR associated system comprising:

a) one or more RNA molecules comprising a guide sequence portion linked to a direct repeat sequence, wherein the guide sequence is capable of hybridizing with a target sequence, or one or more nucleotide sequences encoding the one or more RNA molecules; and b) an CRISPR nuclease comprising an amino acid sequence having at least 95% identity to the amino acid sequence of SEQ ID NO: 1 or a nucleic acid molecule comprising a sequence encoding the CRISPR nuclease; and wherein the one or more RNA molecules hybridize to the target sequence, wherein the target sequence is adjacent to a complimentary sequence of a Protospacer Adjacent Motif (PAM), and the one or more RNA molecules form a complex with the RNA-guided nuclease.

This invention also provides a non-naturally occurring composition comprising:

a) a CRISPR nuclease comprising a sequence having at least 95% identity to the amino acid sequence of SEQ ID NO: 1 or a nucleic acid molecule comprising a sequence encoding the CRISPR nuclease; and b) one or more RNA molecules, or one or more DNA polynucleotide encoding the one or more RNA molecules, comprising at least one of:

i) a nuclease-binding RNA nucleotide sequence capable of interacting with/binding to the CRISPR nuclease; and ii) a DNA-targeting RNA nucleotide sequence comprising a sequence complementary to a sequence in a target DNA sequence, wherein the CRISPR nuclease is capable of complexing with the one or more RNA molecules to form a complex capable of hybridizing with the target DNA sequence.

OMNI-103 CRISPR Nuclease-RNA Complexes

The invention also provides a composition comprising a non-naturally occurring RNA molecule, the RNA molecule comprising a crRNA repeat sequence portion and guide sequence portion, wherein the RNA molecule forms a complex with and targets an OMNI-103 nuclease to a DNA target site in the presence of a tracrRNA sequence, wherein the tracrRNA sequence is encoded by a tracrRNA portion of the RNA molecule or a tracrRNA portion of a second RNA molecule.

The invention also provides a composition comprising a non-naturally occurring RNA molecule, the RNA molecule comprising an RNA scaffold portion, the RNA scaffold portion having the structure:

crRNA repeat sequence portion—tracrRNA portion;

wherein the RNA scaffold portion forms a complex with and targets an OMNI-103 CRISPR nuclease to a DNA target site having complementarity to a guide sequence portion of the RNA molecule.

Disclosed herein are compositions and methods that may be utilized for genomic engineering, epigenomic engineering, genome targeting, genome editing of cells, and/or in vitro diagnostics using an OMNI-103 CRISPR nuclease and a non-naturally occurring RNA molecule comprising a scaffold portion capable of specifically binding and activating the OMNI-103 CRISPR nuclease to target a DNA target site based on a guide sequence portion, also referred to as a RNA spacer portion, of the RNA molecule.

The disclosed compositions may be utilized for modifying genomic DNA sequences. As used herein, genomic DNA refers to linear and/or chromosomal DNA and/or plasmid or other extrachromosomal DNA sequences present in the cell or cells of interest. In some embodiments, the cell of interest is a eukaryotic cell. In some embodiments, the cell of interest is a prokaryotic cell. In some embodiments, the methods produce double-strand breaks (DSBs) at pre-determined target sites in a genomic DNA sequence, resulting in mutation, insertion, and/or deletion of a DNA sequence at the target site(s) in a genome.

BRIEF DESCRIPTION OF THE DRAWINGS

FIG. 1A: A representation of a crRNA-tracrRNA duplex for OMNI-103 V1 (FIG. 1A) and V2 (FIG. 1B) with the crRNA and tracrRNA portions of the sgRNA noted (See Table 2).

(FIG. 2A) For in vitro assays, reducing amounts of RNPs (4, 2, 1 and 0.5 pmol) with spacer lengths 20-25 bps (listed in Table 6) were incubated with 40 ng PDCD1 DNA target template. Activity was verified by the ability to cleave the linear template. (FIGS. 2B-C) In vivo assays (FIG. 2B) RNPs with spacer lengths (20-25 nucleotides) of PDCD1 S40 were electroporated into U2OS cell line and editing levels (indels) measured by NGS. (FIG. 2C) Activity assay for OMNI-103 as RNP in U2OS cells: RNPs with PDCD1 S40, TRACS35, TRACS33 and B2M S12 (22 bp spacer length, Table 6) were electroporated into U2OS cell line and editing levels (indels) measured by next generation sequencing (NGS).

(FIG. 3A) Editing levels (indels) and dsODN integration were measured by NGS. (FIG. 3B) Guide seq analysis did not show any off-target at the PDCD1 S40 site (SEQ ID NO: 133) or TRAC S35 site (SEQ ID NO: 134).

FIGS. 4A-4B: In vitro TXTL PAM depletion results for OMNI nucleases. The PAM logo is a schematic representation of the ratio of the depleted site (top panel). Depletion ratio (bottom panel, right) of specific PAM sequences (bottom panel, left) from the PAM plasmid library were calculated following NGS of the TXTL reaction. The calculation for each OMNI is based on a 4N window along the 8 bp sequence of the PAM library. The required PAM of the tested OMNI and the level of nuclease activity under the reaction conditions is inferred from the depletion ratio. In vitro PAM depletion results for: FIG. 4A: OMNI-103 with sgRNA 12. FIG. 4B: OMNI-103 with sgRNA 32.

FIGS. 5A-5C: OMNI-103 sgRNA versions show editing in Hela cells. To shorten the sgRNA for OMNI-103 four different versions of the scaffold were tested. These versions included deletions at the upper stem and/or at the terminal hairpin. FIG. 5A: A multiple sequence alignment of the different sgRNA designed for OMNI-103. Specifically, alignment of OMNI-103 sgRNA v2 scaffold (107 nucleotides, RNA listed as SEQ ID NO: 16) with shorter sgRNA scaffold versions OMNI-103.1 (101 nucleotides, RNA listed as SEQ ID NO: 33), OMNI-103.2 (85 nucleotides, RNA listed as SEQ ID NO: 34), OMNI-103.3 (79 nucleotides, RNA listed as SEQ ID NO: 35), and OMNI-103.4 (95 nucleotides, RNA listed as SEQ ID NO: 36). FIG. 5B: The predicted structure of sgRNA 103.v2, which was used as template creating the shorter versions (deletions used to create the shorter versions are indicated). FIG. 5C: The editing activity of OMNI-103 CRISPR nuclease with the different scaffolds as determined by next-generation sequencing (NGS). Two sites were tested TRAC S91 and PDCD S40. The transfection efficiency was determined by FACS as the plasmid expressed a reporter fluorescent protein (mCherry).

FIG. 6A: Scaffold V2. FIG. 6B: Scaffold V2.1. FIG. 6C: Scaffold V2.2. FIG. 6D: Scaffold V2.3. FIG. 6E: Scaffold V2.4. FIG. 6F: Scaffold V2.5.

DETAILED DESCRIPTION

Figure 1A:
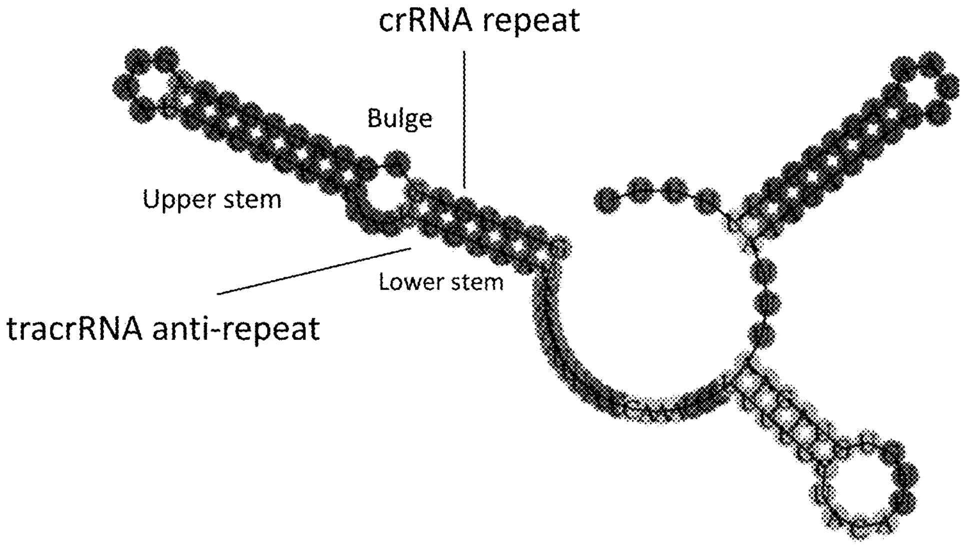
FIGS. 1A-1B: The predicted secondary structure of sgRNA12, a single guide RNA (sgRNA) (crRNA-tracrRNA) compatible with OMNI-103.

According to some aspects of the invention, the disclosed compositions comprise a Clustered Regularly Interspaced Short Palindromic Repeats (CRISPR) nuclease and/or a nucleic acid molecule comprising a sequence encoding the same.

Table 1 lists novel CRISPR nucleases, as well as substitutions at one or more positions within each nuclease which convert the nuclease to a nickase or catalytically dead nuclease.

Table 2 provides crRNA, tracrRNA, and single-guide RNA (sgRNA) sequences, and portions of crRNA, tracrRNA, and sgRNA sequences, that are compatible with each listed CRISPR nuclease. Accordingly, a crRNA molecule capable of binding and targeting an OMNI nuclease listed in Table 2 as part of a crRNA: tracrRNA complex may comprise any crRNA sequence listed in Table 2. Similarly, a tracrRNA molecule capable of binding and targeting an OMNI nuclease listed in Table 2 as part of a crRNA: tracrRNA complex may comprise any tracrRNA sequence listed in Table 2. Also, a single-guide RNA molecule capable of binding and targeting an OMNI nuclease listed in Table 2 may comprise any sequence listed in Table 2.

For example, a crRNA molecule of OMNI-103 nuclease (SEQ ID NO: 1) may comprise a sequence of any one of SEQ ID NOs: 4-7 and 18-21; a tracrRNA molecule of OMNI-103 nuclease may comprise a sequence of any one of SEQ ID NOs: 8-14, 17, 22-28, and 32; and a sgRNA molecule of OMNI-103 nuclease may comprise a sequence of any one of SEQ ID NOs: 4-36. Other crRNA molecules, tracrRNA molecules, or sgRNA molecules for each OMNI nuclease may be derived from the sequences listed in Table 2 in the same manner.

The invention provides a non-naturally occurring composition comprising a CRISPR nuclease comprising a sequence having at least 90% identity to the amino acid sequence of SEQ ID NO: 1, or a nucleic acid molecule comprising a sequence encoding the CRISPR nuclease. The nucleic acid molecule may be, for example, a DNA molecule or an RNA molecule.

In some embodiments, the CRISPR nuclease has full catalytic activity, is a nickase, or is catalytically inactive, and is fused to a DNA-interacting or a modifying protein. For example, the CRISPR nuclease may be fused to deaminase protein for use in base editing methods. In another example, the CRISPR nuclease may be fused to a reverse transcriptase for use in prime editing methods.

In some embodiments, the composition further comprises one or more RNA molecules, or a DNA polynucleotide encoding any one of the one or more RNA molecules, wherein the one or more RNA molecules and the CRISPR nuclease do not naturally occur together and the one or more RNA molecules are configured to form a complex with the CRISPR nuclease and/or target the complex to a target site.

In some embodiments, the CRISPR nuclease comprises a sequence having at least 90% identity to the amino acid sequence set forth in SEQ ID NO: 1 and at least one RNA molecule comprises a sequence selected from the group consisting of SEQ ID NOs: 4-36.

In some embodiments, the CRISPR nuclease comprises a sequence having at least 90% identity to the amino acid sequence set forth in SEQ ID NO: 1 and at least one RNA molecule is a CRISPR RNA (crRNA) molecule comprising a guide sequence portion and a sequence selected from the group consisting of SEQ ID NOs: 4-7 and 18-21.

In some embodiments, the composition further comprises a transactivating CRISPR RNA (tracrRNA) molecule comprising a sequence set forth in the group consisting of SEQ ID NOs: 8-14, 17, 22-28, and 32.

In some embodiments, the CRISPR nuclease comprises a sequence having at least 90% identity to the amino acid sequence set forth in SEQ ID NO: 1 and at least one RNA molecule is a single-guide RNA (sgRNA) molecule comprising a guide sequence portion and a sequence selected from the group consisting of SEQ ID NOs: 4-36.

In some embodiments, the CRISPR nuclease comprises a sequence having at least 90% identity to the amino acid sequence set forth in SEQ ID NO: 1 and at least one RNA molecule is a single-guide RNA (sgRNA) molecule comprising a guide sequence portion and a scaffold portion that is at least 79 nucleotides in length.

In some embodiments, the CRISPR nuclease is a nickase having an inactivated RuvC domain created by an amino acid substitution at a position provided for the CRISPR nuclease in column 5 of Table 1.

In some embodiments, the CRISPR nuclease is a nickase having an inactivated HNH domain created by an amino acid substitution at a position provided for the CRISPR nuclease in column 6 of Table 1.

In some embodiments, the CRISPR nuclease is a catalytically dead nuclease having an inactivated RuvC domain and an inactivated HNH domain created by substitutions at the positions provided for the CRISPR nuclease in column 7 of Table 1.

For example, a nickase may be generated for the OMNI-103 nuclease by inactivating its RuvC domain by substituting an aspartic acid residue (D) in position 12 of the amino acid sequence of OMNI-103 (SEQ ID NO: 1) for another amino acid e.g. alanine (A). Substitution to any other amino acid is permissible for each of the amino acid positions indicated in columns 5-7 of Table 1, except if the amino acid position is followed by an asterisk, which indicates that any substitution other than aspartic acid (D) to glutamic acid (E) or glutamic acid (E) or aspartic acid (D) results in inactivation. For example, a nickase may be generated for the OMNI-103 nuclease by inactivating its HNH domain by substituting an aspartic acid (D) in position 856 of the amino acid sequence of OMNI-103 (SEQ ID NO: 1) for an amino acid other than glutamic acid residue (E), e.g. for alanine (A). Other nickases or catalytically dead nucleases can be generated using the same notation in Table 1.

In some embodiments, the CRISPR nuclease is a nickase created by an amino acid substitution at position D12, E776, H988 or D991.

In some embodiments, the CRISPR nuclease is a nickase created by an amino acid substitution at position D856, H857 or N880, wherein an amino acid substitution at position D856 is a substitution other than aspartic acid (D) to glutamic acid (E).

In some embodiments, the CRISPR nuclease is a catalytically dead nuclease created by an amino acid substitution at any one of positions D12, E776, H988 or D991 and an amino acid substitution at any one of positions D856, H857 or N880, wherein an amino acid substitution at position D856 is a substitution other than aspartic acid (D) to glutamic acid (E).

In some embodiments, the CRISPR nuclease utilizes a protospacer adjacent motif (PAM) sequence provided for the CRISPR nuclease in column 2 or column 3 of Table 3.

The invention also provides a method for modifying a nucleotide sequence at a DNA target site in a cell-free system or the genome of a cell comprising introducing into the cell any one of the compositions described above. In some embodiments, the composition comprises a CRISPR nuclease and a crRNA: tracrRNA complex or a sgRNA molecule.

In some embodiments, the CRISPR nuclease effects a DNA break in a DNA strand adjacent to a protospacer adjacent motif (PAM) sequence provided for the CRISPR nuclease in column 2 or column 3 of Table 3, and effects a DNA break in a DNA strand adjacent to a sequence that is complementary to the PAM sequence. For example, the OMNI-103 nuclease with the appropriate targeting sgRNA or crRNA: tracrRNA complex is capable of forming a DNA break in strand adjacent to a NNRRHY, NNRACT, or NNRVCT sequence and in a DNA strand adjacent to a sequence that is complementary to a NNRRHY, NNRACT, or NNRVCT sequence. In some embodiments, the DNA strand is within a nucleus of a cell.

In some embodiments, the CRISPR nuclease is a nickase having an inactivated RuvC domain created by an amino acid substitution at a position provided for the CRISPR nuclease in column 5 of Table 1, and effects a DNA break in a DNA strand adjacent to a sequence that is complementary to the PAM sequence.

In some embodiments, the CRISPR nuclease is a nickase having an inactivated HNH domain created by an amino acid substitution at a position provided for the CRISPR nuclease in column 6 of Table 1, and effects a DNA break in a DNA strand adjacent to the PAM sequence.

In some embodiments, the CRISPR nuclease is a catalytically dead nuclease having an inactivated RuvC domain and an inactivated HNH domain created by substitutions at the positions provided for the CRISPR nuclease in column 7 of Table 1, and effects a DNA break in a DNA strand adjacent to the PAM sequence.

The invention also provides a method of modifying a nucleotide sequence at a DNA target site in a cell-free system or the genome of a cell comprising introducing into the cell any one of the compositions provided herein.

In some embodiments, the CRISPR nuclease comprises a sequence having at least 90% identity to the amino acid sequence set forth in SEQ ID NO: 1, wherein the CRISPR nuclease effects a DNA strand break adjacent to a NNRRHY, NNRACT, or NNRVCT protospacer adjacent motif (PAM) sequence, and/or effects a DNA strand break adjacent to a sequence that is complementary to the PAM sequence.

In some embodiments, the CRISPR nuclease is a nickase created by an amino acid substitution at position D12, E776, H988 or D991, and effects a DNA strand break adjacent to the PAM sequence.

In some embodiments, the CRISPR nuclease is a nickase created by an amino acid substitution at position D856, H857 or N880, and effects a DNA strand break adjacent to a sequence that is complementary to the PAM sequence, wherein an amino acid substitution at position D856 is a substitution other than aspartic acid (D) to glutamic acid (E).

In some embodiments, the cell is a eukaryotic cell or a prokaryotic cell.

In some embodiments, the cell is a mammalian cell.

In some embodiments, the cell is a human cell.

In some embodiments, the CRISPR nuclease comprises an amino acid sequence having at least 100%, 99%, 98%, 97%, 96%, 95%, 94%, 93%, 92%, 91%, 90%, 89%, 88%, 87%, 86%, 85%, 84%, 83%, or 82% amino acid sequence identity to a CRISPR nuclease as SEQ ID NO: 1. In an embodiment the sequence encoding the CRISPR nuclease has at least 100%, 99%, 98%, 97%, 96%, 95%, 94%, 93%, 92%, 91%, 90%, 89%, 88%, 87%, 86%, 85%, 84%, 83%, or 82% identity to a nucleic acid sequence selected from the group consisting of SEQ ID NOs: 2-3.

The invention also provides a non-naturally occurring composition comprising a CRISPR nuclease, wherein the CRISPR nuclease comprises an amino acid sequence corresponding to the amino acid sequence of at least one of Domain A, Domain B, Domain C, Domain D, Domain E, Domain F, Domain G, Domain H, Domain I, or Domain J of SEQ ID NO: 1.

a) wherein Domain A comprises a sequence having at least 90%, 91%, 92%, 93%, 94%, 95%, 96%, 97%, 98%, 99%, or 100% identity to amino acids 1-45 of SEQ ID NO: 1;
b) wherein Domain B comprises a sequence having at least 90%, 91%, 92%, 93%, 94%, 95%, 96%, 97%, 98%, 99%, or 100% identity to amino acids 46-83 of SEQ ID NO: 1;
c) wherein Domain C comprises a sequence having at least 90%, 91%, 92%, 93%, 94%, 95%, 96%, 97%, 98%, 99%, or 100% identity to amino acids 84-158 of SEQ ID NO: 1;
d) wherein Domain D comprises a sequence having at least 90%, 91%, 92%, 93%, 94%, 95%, 96%, 97%, 98%, 99%, or 100% identity to amino acids 159-302 of SEQ ID NO: 1;
e) wherein Domain E comprises a sequence having at least 90%, 91%, 92%, 93%, 94%, 95%, 96%, 97%, 98%, 99%, or 100% identity to amino acids 303-515 of SEQ ID NO: 1;
f) wherein Domain F comprises a sequence having at least 90%, 91%, 92%, 93%, 94%, 95%, 96%, 97%, 98%, 99%, or 100% identity to amino acids 516-727 of SEQ ID NO: 1;
g) wherein Domain G comprises a sequence having at least 90%, 91%, 92%, 93%, 94%, 95%, 96%, 97%, 98%, 99%, or 100% identity to amino acids 728-778 of SEQ ID NO: 1;
h) wherein Domain H comprises a sequence having at least 90%, 91%, 92%, 93%, 94%, 95%, 96%, 97%, 98%, 99%, or 100% identity to amino acids 779-923 of SEQ ID NO: 1;
i) wherein Domain I comprises a sequence having at least 90%, 91%, 92%, 93%, 94%, 95%, 96%, 97%, 98%, 99%, or 100% identity to amino acids 924-1068 of SEQ ID NO: 1; and
j) wherein Domain J comprises a sequence having at least 90%, 91%, 92%, 93%, 94%, 95%, 96%, 97%, 98%, 99%, or 100% identity to amino acids 1069-1348 of SEQ ID NO: 1.

According to some aspects of the invention, the disclosed compositions comprise DNA constructs or a vector system comprising nucleotide sequences that encode the CRISPR nuclease or variant CRISPR nuclease. In some embodiments, the nucleotide sequence that encode the CRISPR nuclease or variant CRISPR nuclease is operably linked to a promoter that is operable in the cells of interest. In some embodiments, the cell of interest is a eukaryotic cell. In some embodiments the cell of interest is a mammalian cell. In some embodiments, the nucleic acid sequence encoding the engineered CRISPR nuclease is codon optimized for use in cells from a particular organism. In some embodiments, the nucleic acid sequence encoding the nuclease is codon optimized for *E. coli*. In some embodiments, the nucleic acid sequence encoding the nuclease is codon optimized for eukaryotic cells. In some embodiments, the nucleic acid sequence encoding the nuclease is codon optimized for mammalian cells.

In some embodiments, the composition comprises a recombinant nucleic acid, comprising a heterologous promoter operably linked to a polynucleotide encoding a CRISPR enzyme having at least 100%, 99%, 98%, 97%, 96%, 95%, 94%, 93%, 92%, 91%, 90% identity to SEQ ID NO: 1. Each possibility represents a separate embodiment.

In an embodiment of the composition, the CRISPR nuclease has at least 75%, 80%, 85, 90%, 95%, or 97% identity to the amino acid sequence as set forth in SEQ ID NO: 1 or the sequence encoding the CRISPR nuclease has at least a 75%, 80%, 85, 90%, 95%, or 97% sequence identity to a nucleotide sequence selected from the group consisting of SEQ ID NOs: 2 and 3.

According to some embodiments, there is provided an engineered or non-naturally occurring composition comprising a CRISPR nuclease comprising a sequence having at least 100%, 99%, 98%, 97%, 96%, 95%, 94%, 93%, 92%, 91%, 90%, 85%, 80% identity to the amino acid sequence of SEQ ID NO: 1 or a nucleic acid molecule comprising a sequence encoding the CRISPR nuclease. Each possibility represents a separate embodiment.

In an embodiment, the CRISPR nuclease is engineered or non-naturally occurring. The CRISPR nuclease may also be recombinant. Such CRISPR nucleases are produced using laboratory methods (e.g. molecular cloning) to bring together genetic material from multiple sources, creating sequences that would not otherwise be found in biological organisms.

In an embodiment, the CRISPR nuclease further comprises an RNA-binding portion capable of interacting with a DNA-targeting RNA molecule (gRNA) and an activity portion that exhibits site-directed enzymatic activity.

In an embodiment, the composition further comprises a DNA-targeting RNA molecule or a DNA polynucleotide encoding a DNA-targeting RNA molecule, wherein the DNA-targeting RNA molecule comprises a guide sequence portion, i.e. a nucleotide sequence that is complementary to a sequence in a target region, wherein the DNA-targeting RNA molecule and the CRISPR nuclease do not naturally occur together.

In an embodiment, the DNA-targeting RNA molecule further comprises a nucleotide sequence that can form a complex with a CRISPR nuclease.

This invention also provides a non-naturally occurring composition comprising a CRISPR associated system comprising:

a) one or more RNA molecules comprising a guide sequence portion linked to a direct repeat sequence, wherein the guide sequence is capable of hybridizing with a target sequence, or one or more nucleotide sequences encoding the one or more RNA molecules; and b) a CRISPR nuclease comprising an amino acid sequence having at least 95% identity to the amino acid sequence of SEQ ID NO: 1 or a nucleic acid molecule comprising a sequence encoding the CRISPR nuclease;

wherein the one or more RNA molecules hybridize to the target sequence, wherein the target sequence is adjacent to a Protospacer Adjacent Motif (PAM), and the one or more RNA molecules form a complex with the RNA-guided nuclease.

In an embodiment, the composition further comprises an RNA molecule comprising a nucleotide sequence that can form a complex with a CRISPR nuclease (e.g. a tracrRNA molecule) or a DNA polynucleotide comprising a sequence encoding an RNA molecule that can form a complex with the CRISPR nuclease.

In an embodiment, the composition further comprises a donor template for homology directed repair (HDR).

In an embodiment, the composition is capable of editing the target region in the genome of a cell.

According to some embodiments, there is provided a non-naturally occurring composition comprising:

(a) a CRISPR nuclease, or a polynucleotide encoding the CRISPR nuclease, comprising: an RNA-binding portion; and an activity portion that exhibits site-directed enzymatic activity, wherein the CRISPR nuclease has at least 100%, 99%, 98%, 97%, 96%, 95%, 94%, 93%, 92%, 91%, 90%, 85%, 80% identity to SEQ ID NO: 1; and (b) one or more RNA molecules or a DNA polynucleotide encoding the one or more RNA molecules comprising:

i) a DNA-targeting RNA sequence, comprising a nucleotide sequence that is complementary to a sequence in a target DNA sequence; and ii) a protein-binding RNA sequence, capable of interacting with the RNA-binding portion of the CRISPR nuclease, wherein the DNA targeting RNA sequence and the CRISPR nuclease do not naturally occur together. Each possibility represents a separate embodiment.

In some embodiments, there is provided a single RNA molecule comprising the DNA-targeting RNA sequence and the protein-binding RNA sequence, wherein the RNA molecule can form a complex with the CRISPR nuclease and serve as the DNA targeting module. In some embodiments, the RNA molecule has a length of up to 1000 bases, 900 bases, 800 bases, 700 bases, 600 bases, 500 bases, 400 bases, 300 bases, 200 bases, 100 bases, 50 bases. Each possibility represents a separate embodiment. In some embodiments, a first RNA molecule comprising the DNA-targeting RNA sequence and a second RNA molecule comprising the protein-binding RNA sequence interact by base pairing or alternatively fused together to form one or more RNA molecules that complex with the CRISPR nuclease and serve as the DNA targeting module.

This invention also provides a non-naturally occurring composition comprising:

a) a CRISPR nuclease comprising a sequence having at least 95% identity to the amino acid sequence of SEQ ID NOs: 1 or a nucleic acid molecule comprising a sequence encoding the CRISPR nuclease; and b) one or more RNA molecules, or one or more DNA polynucleotide encoding the one or more RNA molecules, comprising at least one of:

i) a nuclease-binding RNA nucleotide sequence capable of interacting with/binding to the CRISPR nuclease; and ii) a DNA-targeting RNA nucleotide sequence comprising a sequence complementary to a sequence in a target DNA sequence, wherein the CRISPR nuclease is capable of complexing with the one or more RNA molecules to form a complex capable of hybridizing with the target DNA sequence.

In an embodiment, the CRISPR nuclease and the one or more RNA molecules form a CRISPR complex that is capable of binding to the target DNA sequence to effect cleavage of the target DNA sequence.

In an embodiment, the CRISPR nuclease and at least one of the one or more RNA molecules do not naturally occur together.

In an embodiment:

a) the CRISPR nuclease comprises an RNA-binding portion and an activity portion that exhibits site-directed enzymatic activity;

b) the DNA-targeting RNA nucleotide sequence comprises a nucleotide sequence that is complementary to a sequence in a target DNA sequence; and c) the nuclease-binding RNA nucleotide sequence comprises a sequence that interacts with the RNA-binding portion of the CRISPR nuclease.

In an embodiment, the nuclease-binding RNA nucleotide sequence and the DNA-targeting RNA nucleotide sequence are on a single guide RNA molecule (sgRNA), wherein the sgRNA molecule can form a complex with the CRISPR nuclease and serve as the DNA targeting module.

In an embodiment, the nuclease-binding RNA nucleotide sequence is on a first RNA molecule and the DNA-targeting RNA nucleotide sequence is on a second RNA molecule, and wherein the first and second RNA molecules interact by base-pairing or are fused together to form a RNA complex or sgRNA that forms a complex with the CRISPR nuclease and serves as a DNA targeting module.

In an embodiment, the sgRNA has a length of up to 1000 bases, 900 bases, 800 bases, 700 bases, 600 bases, 500 bases, 400 bases, 300 bases, 200 bases, 100 bases, 50 bases.

In an embodiment, the composition further comprises a donor template for homology directed repair (HDR).

In an embodiment, the CRISPR nuclease is non-naturally occurring.

In an embodiment, the CRISPR nuclease is engineered and comprises unnatural or synthetic amino acids.

In an embodiment, the CRISPR nuclease is engineered and comprises one or more of a nuclear localization sequences (NLS), cell penetrating peptide sequences, and/or affinity tags.

In an embodiment, the CRISPR nuclease comprises one or more nuclear localization sequences of sufficient strength to drive accumulation of a CRISPR complex comprising the CRISPR nuclease in a detectable amount in the nucleus of a eukaryotic cell.

This invention also provides a method of modifying a nucleotide sequence at a target site in a cell-free system or the genome of a cell comprising introducing into the cell any of the compositions of the invention.

In an embodiment, the cell is a eukaryotic cell.

In another embodiment, the cell is a prokaryotic cell.

In some embodiments, the one or more RNA molecules further comprises an RNA sequence comprising a nucleotide molecule that can form a complex with the RNA nuclease (tracrRNA) or a DNA polynucleotide encoding an RNA molecule comprising a nucleotide sequence that can form a complex with the CRISPR nuclease.

In an embodiment, the CRISPR nuclease comprises 1, 2, 3, 4, 5, 6, 7, 8, 9, 10, or more NLSs at or near the amino-terminus, 1, 2, 3, 4, 5, 6, 7, 8, 9, 10, or more NLSs at or near carboxy-terminus, or a combination of 1, 2, 3, 4, 5, 6, 7, 8, 9, 10, or more NLSs at or near the amino-terminus and 1, 2, 3, 4, 5, 6, 7, 8, 9, 10, or more NLSs at or near carboxy-terminus. In an embodiment 1-4 NLSs are fused with the CRISPR nuclease. In an embodiment, an NLS is located within the open-reading frame (ORF) of the CRISPR nuclease.

Methods of fusing an NLS at or near the amino-terminus, at or near carboxy-terminus, or within the ORF of an expressed protein are well known in the art. As an example, to fuse an NLS to the amino-terminus of a CRISPR nuclease, the nucleic acid sequence of the NLS is placed immediately after the start codon of the CRISPR nuclease on the nucleic acid encoding the NLS-fused CRISPR nuclease. Conversely, to fuse an NLS to the carboxy-terminus of a CRISPR nuclease the nucleic acid sequence of the NLS is placed after the codon encoding the last amino acid of the CRISPR nuclease and before the stop codon.

Any combination of NLSs, cell penetrating peptide sequences, and/or affinity tags at any position along the ORF of the CRISPR nuclease is contemplated in this invention.

The amino acid sequences and nucleic acid sequences of the CRISPR nucleases provided herein may include NLS and/or TAGs inserted so as to interrupt the contiguous amino acid or nucleic acid sequences of the CRISPR nucleases.

In an embodiment, the one or more NLSs are in tandem repeats.

In an embodiment, the one or more NLSs are considered in proximity to the N- or C-terminus when the nearest amino acid of the NLS is within about 1, 2, 3, 4, 5, 10, 15, 20, 25, 30, 40, 50, or more amino acids along the polypeptide chain from the N- or C-terminus.

As discussed, the CRISPR nuclease may be engineered to comprise one or more of a nuclear localization sequences (NLS), cell penetrating peptide sequences, and/or affinity tags.

In an embodiment, the composition further comprises a recombinant nucleic acid molecule comprising a heterologous promoter operably linked to the nucleotide acid molecule comprising the sequence encoding the CRISPR nuclease.

In an embodiment, the CRISPR nuclease or nucleic acid molecule comprising a sequence encoding the CRISPR nuclease is non-naturally occurring or engineered.

This invention also provides a non-naturally occurring or engineered composition comprising a vector system comprising the nucleic acid molecule comprising a sequence encoding any of the CRISPR nucleases of the invention.

This invention also provides use of any of the compositions of the invention for the treatment of a subject afflicted with a disease associated with a genomic mutation comprising modifying a nucleotide sequence at a target site in the genome of the subject.

This invention provides a method of modifying a nucleotide sequence at a target site in the genome of a mammalian cell comprising introducing into the cell (i) a composition comprising a CRISPR nuclease having at least 95% identity to an amino acid sequence of SEQ ID NO: 1 or a nucleic acid molecule comprising a sequence encoding a CRISPR nuclease which sequence has at least 95% identity to a nucleic acid sequence of SEQ ID NOs: 2-3 and (ii) a DNA-targeting RNA molecule, or a DNA polynucleotide encoding a DNA-targeting RNA molecule, comprising a nucleotide sequence that is complementary to a sequence in the target DNA.

In some embodiments, the method is performed ex vivo. In some embodiments, the method is performed in vivo. In some embodiments, some steps of the method are performed ex vivo and some steps are performed in vivo. In some embodiments the mammalian cell is a human cell.

In an embodiment, the method further comprises introducing into the cell: (iii) an RNA molecule comprising a tracrRNA sequence or a DNA polynucleotide encoding an RNA molecule comprising a tracrRNA sequence.

In an embodiment, the DNA-targeting RNA molecule comprises a crRNA repeat sequence.

In an embodiment, the RNA molecule comprising a tracrRNA sequence is able to bind the DNA-targeting RNA molecule.

In an embodiment, the DNA-targeting RNA molecule and the RNA molecule comprising a tracrRNA sequence interact to form an RNA complex, and the RNA complex is capable of forming an active complex with the CRISPR nuclease.

In an embodiment, the DNA-targeting RNA molecule and the RNA molecule comprising a nuclease-binding RNA sequence are fused in the form of a single guide RNA molecule that is suitable to form an active complex with the CRISPR nuclease.

In an embodiment, the guide sequence portion comprises a sequence complementary to a protospacer sequence.

In an embodiment, the CRISPR nuclease forms a complex with the DNA-targeting RNA molecule and effects a double strand break in a region that is 3' or 5' of a Protospacer Adjacent Motif (PAM).

In an embodiment of any of the methods described herein, the method is for treating a subject afflicted with a disease associated with a genomic mutation comprising modifying a nucleotide sequence at a target site in the genome of the subject.

In an embodiment, the method comprises first selecting a subject afflicted with a disease associated with a genomic mutation and obtaining the cell from the subject.

This invention also provides a modified cell or cells obtained by any of the methods described herein. In an embodiment these modified cell or cells are capable of giving rise to progeny cells. In an embodiment these modified cell or cells are capable of giving rise to progeny cells after engraftment.

This invention also provides a composition comprising these modified cells and a pharmaceutically acceptable carrier. Also provided is an in vitro or ex vivo method of preparing this, comprising mixing the cells with the pharmaceutically acceptable carrier.

The invention also provides a composition comprising a non-naturally occurring RNA molecule, the RNA molecule comprising a crRNA repeat sequence portion and a guide sequence portion, wherein the RNA molecule forms a complex with and targets an OMNI-103 nuclease to a DNA target site in the presence of a tracrRNA sequence, wherein the tracrRNA sequence is encoded by a tracrRNA portion of the RNA molecule or a tracrRNA portion of a second RNA molecule.

In some embodiments, the crRNA repeat sequence portion is up to 17 nucleotides in length, preferably 14-17 nucleotides in length.

In some embodiments, the crRNA repeat sequence portion has at least 60-70%, 71-80%, 81-90%, 91-95%, or 96-99% sequence identity to SEQ ID NOs: 114 or 115.

In some embodiments, the crRNA repeat sequence portion has at least 95% sequence identity to any one of SEQ ID NOs: 114 or 115.

In some embodiments, the crRNA repeat sequence is other than SEQ ID NO: 115.

In some embodiments, the RNA molecule comprising the crRNA repeat sequence portion and the guide sequence portion further comprises the tracrRNA portion.

In some embodiments, the crRNA repeat sequence portion is covalently linked to the tracrRNA portion by a polynucleotide linker portion.

In some embodiments, the composition comprises a second RNA molecule comprising the tracrRNA portion.

In some embodiments, the OMNI-103 nuclease has at least 95% sequence identity to the amino acid sequence of SEQ ID NO: 1.

In some embodiments, the guide sequence portion is 17-30 nucleotides in length, preferably 22 nucleotides in length.

The invention also provides a composition comprising a non-naturally occurring RNA molecule, the RNA molecule comprising a tracrRNA portion, wherein the RNA molecule forms a complex with and targets an OMNI-103 nuclease to a DNA target site in the presence of a crRNA repeat sequence portion and a guide sequence portion, wherein the crRNA repeat sequence portion and the guide sequence portion are encoded by the RNA molecule or a second RNA molecule.

In some embodiments, the tracrRNA portion is less than 85 nucleotides in length, preferably 84-80, 79-75, 74-70, 69-65, or 64-60 nucleotides in length.

In some embodiments, the tracrRNA portion has at least 30-40%, 41-50%, 51-60%, 61-70%, 71-80%, 81-90%, 91-95%, or 96-99% sequence identity to the tracrRNA portion of any one of SEQ ID NOs: 109-113.

In some embodiments, the tracrRNA portion has at least 95% sequence identity to the tracrRNA portions of any one of SEQ ID NOs: 109-113.

In some embodiments, the tracrRNA portion is other than the tracr portion of SEQ ID NO: 15 or 16.

In some embodiments, the tracrRNA portion comprises a tracrRNA anti-repeat sequence portion that is up to 19 nucleotides in length, preferably 16-19 nucleotides in length.

In some embodiments, the tracrRNA portion comprises a tracrRNA anti-repeat sequence portion that has at least 60-70%, 71-80%, 81-90%, 91-95%, or 96-99% sequence identity to any one of SEQ ID NOs: 116 or 117.

In some embodiments, the tracrRNA portion comprises a tracrRNA anti-repeat sequence portion that has at least 95% sequence identity to any one of SEQ ID NOs: 116 or 117.

In some embodiments, the tracrRNA portion comprises a tracrRNA anti-repeat sequence portion having a sequence other than SEQ ID NO: 117.

In some embodiments, the RNA molecule comprises a tracrRNA portion and further comprises a crRNA repeat sequence portion and a guide sequence portion.

In some embodiments, the tracrRNA portion is covalently linked to the crRNA repeat sequence by a polynucleotide linker portion.

In some embodiments, the polynucleotide linker portion is 4-10 nucleotides in length.

In some embodiments, the polynucleotide linker has a sequence of GAAA.

In some embodiments, the composition further comprises a second RNA molecule comprising a crRNA repeat sequence portion and a guide sequence portion.

In some embodiments, the OMNI-103 nuclease is at least 95% sequence identity to the amino acid sequence of SEQ ID NO: 1.

In some embodiments, the guide sequence portion is 17-30 nucleotides in length, preferably 22 nucleotides in length.

The invention also provides a composition comprising a non-naturally occurring RNA molecule, the RNA molecule comprising an RNA scaffold portion, the RNA scaffold portion having the structure:

crRNA repeat sequence portion—tracrRNA portion;

wherein the RNA scaffold portion forms a complex with and targets an OMNI-103 CRISPR nuclease to a DNA target site having complimentarity to a guide sequence portion of the RNA molecule.

In some embodiments, the OMNI-103 nuclease has at least 95% sequence identity to the amino acid sequence of SEQ ID NO: 1.

In some embodiments, the RNA scaffold portion is 110-105, 104-100, 99-95, 94-90, 89-85, 84-80, 79-75, or 74-70 nucleotides in length.

In some embodiments, the RNA scaffold portion is 107, 101, 95, 85, or 79 nucleotides in length.

In some embodiments, the RNA scaffold portion has at least 30%, at least 40%, at least 50%, at least 60%, at least 70%, at least 80%, at least 85%, at least 90%, or at least 95% sequence identity to any one of SEQ ID NOs: 109-113.

In some embodiments, the crRNA repeat sequence portion is up to 17 nucleotides in length, preferably 14-17 nucleotides in length.

In some embodiments, the crRNA repeat sequence portion has at least 60-70%, 71-80%, 81-90%, 91-95%, or 96-99% sequence identity to SEQ ID NOs: 114 or 115.

In some embodiments, the crRNA repeat sequence portion has at least 95% sequence identity to any one of SEQ ID NOs: 114 or 115.

In some embodiments, the crRNA repeat sequence is other than SEQ ID NO: 23.

In some embodiments, the tracrRNA portion is less than 85 nucleotides in length, preferably 84-80, 79-75, 74-70, 69-65, or 64-60 nucleotides in length.

In some embodiments, the tracrRNA portion has at least 30-40%, 41-50%, 51-60%, 61-70%, 71-80%, 81-90%, 91-95%, or 96-99% sequence identity to the tracrRNA portion of any one of SEQ ID NOs: 109-113.

In some embodiments, the tracrRNA portion has at least 95% sequence identity to the tracrRNA portions of any one of SEQ ID NOs: 109-113.

In some embodiments, the tracrRNA portion is other than the tracrRNA portion of SEQ ID NO: 15 or 16.

In some embodiments, the RNA scaffold portion further comprises a linker portion between the crRNA repeat sequence portion and the tracrRNA portion such that the RNA scaffold has the structure:

crRNA repeat sequence portion—linker portion—tracrRNA portion.

In some embodiments, the tracrRNA portion comprises a tracrRNA anti-repeat sequence portion, wherein the crRNA repeat sequence and the tracrRNA anti-repeat sequence portion are covalently linked by the linker portion.

In some embodiments, the linker portion is a polynucleotide linker that is 4-10 nucleotides in length.

In some embodiments, the polynucleotide linker has a sequence of GAAA.

In some embodiments, the tracrRNA portion comprises a tracrRNA anti-repeat sequence portion that is up to 19 nucleotides in length, preferably 16-19 nucleotides in length.

In some embodiments, the tracrRNA portion comprises a tracrRNA anti-repeat sequence portion that has at least 60-70%, 71-80%, 81-90%, 91-95%, or 96-99% sequence identity to any one of SEQ ID NOs: 116 or 117.

In some embodiments, the tracrRNA portion comprises a tracrRNA anti-repeat sequence portion that has at least 95% sequence identity to any one of SEQ ID NOs: 116 or 117.

In some embodiments, the tracrRNA anti-repeat sequence is other than SEQ ID NO: 117.

In some embodiments, the tracrRNA portion comprises a first section of nucleotides linked to the tracrRNA anti-repeat portion, and the first section of nucleotides has at least 95% sequence identity to any one of SEQ ID NOs: 118-120.

In some embodiments, the tracrRNA portion comprises a second section of nucleotides linked to a first section of nucleotides, and the second section of nucleotides has at least 95% sequence identity to any one of SEQ ID NOs: 121-124.

In some embodiments, the RNA scaffold portion has at least 95% identity to the nucleotide sequence of any one of SEQ ID NOs: 109-113.

In some embodiments, the RNA scaffold portion has a predicted structure of any one of the V2, V2.1, V2.2, V2.3, V2.4, or V2.5 RNA scaffolds.

In some embodiments, the RNA scaffold portion has a sequence other than SEQ ID NO: 15 or 16.

In some embodiments, a guide sequence portion is covalently linked to the crRNA repeat sequence portion of the RNA molecule, forming a single-guide RNA molecule having a structure:

guide sequence portion—crRNA repeat sequence portion—tracrRNA portion.

In some embodiments, the guide sequence portion is 17-30 nucleotides, more preferably 20-23 nucleotides, more preferably 22 nucleotides in length.

In some embodiments, the composition further comprises an OMNI-103 CRISPR nuclease, wherein the OMNI-103 CRISPR nuclease has at least 95% identity to the amino acid sequence of SEQ ID NO: 1.

In some embodiments, the RNA molecule is formed by in vitro transcription (IVT) or solid-phase artificial oligonucleotide synthesis.

In some embodiments, the RNA molecule comprises modified nucleotides.

The invention also provides a polynucleotide molecule encoding the RNA molecule of any one of the above embodiments.

The invention also provides a method of modifying a nucleotide sequence at a DNA target site in a cell-free system or a genome of a cell comprising introducing into the system or cell any one of the RNA molecules presented herein and a CRISPR nuclease having at least 95% sequence identity to the amino acid sequence of SEQ ID NO: 1.

In some embodiments, the cell is a eukaryotic cell or a prokaryotic cell.

In some embodiments, the eukaryotic cell is a human cell or a plant cell.

The invention also provides a kit for modifying a nucleotide sequence at a DNA target site in a cell-free system or a genome of a cell comprising introducing into the system or cell the composition of any one of the above embodiments, a CRISPR nuclease having at least 95% sequence identity to the amino acid sequence of SEQ ID NO: 1, and instructions for delivering the RNA molecule and the CRISPR nuclease to the cell.

In embodiments of the present invention, the non-naturally occurring RNA molecule comprises a "spacer" or "guide sequence" portion. The "spacer portion" or "guide sequence portion" of an RNA molecule refers to a nucleotide sequence that is capable of hybridizing to a specific target DNA sequence, e.g., the guide sequence portion has a nucleotide sequence which is fully complementary to the DNA sequence being targeted along the length of the guide sequence portion. In some embodiments, the guide sequence portion is 17, 18, 19, 20, 21, 22, 23, 24, 25, 26, 27, 28, 29, or 30 nucleotides in length, or approximately 17-30, 17-29, 17-28, 17-27, 17-26, 17-25, 17-24, 18-22, 19-22, 18-20, 17-20, or 21-22 nucleotides in length. Preferably, the entire length of the guide sequence portion is fully complementary to the DNA sequence being targeted along the length of the guide sequence portion. The guide sequence portion may be part of an RNA molecule having a "scaffold portion" that can form a complex with and activate a CRISPR nuclease, with the guide sequence portion of the RNA molecule serving as the DNA targeting portion of the CRISPR complex. When the RNA molecule having a scaffold portion and a guide sequence portion is present contemporaneously with the CRISPR molecule, the RNA molecule is capable of targeting the CRISPR nuclease to the specific target DNA sequence. Each possibility represents a separate embodiment. The RNA molecule spacer portion can be custom designed to target any desired sequence.

In an embodiment, the nuclease-binding RNA nucleotide sequence and the DNA-targeting RNA nucleotide sequence (e.g. spacer or guide sequence portion) are on a single-guide RNA molecule (sgRNA), wherein the sgRNA molecule can form a complex with the OMNI-103 CRISPR nuclease and serve as the DNA targeting module.

In an embodiment, the nuclease-binding RNA nucleotide sequence is on a first RNA molecule and the DNA-targeting RNA nucleotide sequence is on a second RNA molecule, and the first and second RNA molecules interact by base-pairing and complex with the CRISPR nuclease to serve as the targeting module.

According to some aspects of the invention, the disclosed methods comprise a method of modifying a nucleotide sequence at a target site in a cell-free system or the genome of a cell comprising introducing into the cell the composition of any one of the embodiments described herein.

This invention also provides use of any of the compositions or methods of the invention for modifying a nucleotide sequence at a DNA target site in a cell.

This invention provides a method of modifying a nucleotide sequence at a target site in the genome of a eukaryotic cell.

This invention provides a method of modifying a nucleotide sequence at a target site in the genome of a mammalian cell. In some embodiments, the mammalian cell is a human cell.

This invention provides a method of modifying a nucleotide sequence at a target site in the genome of a plant cell.

In some embodiments, the method is performed ex vivo. In some embodiments, the method is performed in vivo. In some embodiments, some steps of the method are performed ex vivo and some steps are performed in vivo. In some embodiments the mammalian cell is a human cell.

This invention also provides a modified cell or cells obtained by any of the methods described herein. In an embodiment these modified cell or cells are capable of giving rise to progeny cells. In an embodiment these modified cell or cells are capable of giving rise to progeny cells after engraftment.

This invention also provides a composition comprising these modified cells and a pharmaceutically acceptable carrier. Also provided is an in vitro or ex vivo method of preparing this, comprising mixing the cells with the pharmaceutically acceptable carrier.

This invention also provides a kit for modifying a nucleotide sequence at a DNA target site in a cell-free system or a genome of a cell comprising introducing into the system or cell a CRISPR nuclease having at least 95% sequence identity to the amino acid sequence of SEQ ID NO: 1, one or more RNA molecules configured to form a complex with the CRISPR nuclease and/or target the complex to a target site, and instructions for delivering the RNA molecule and the CRISPR nuclease to the cell. For example, the kit may be used as a diagnostic kit to detect the presence of a target site (e.g. a DNA sequence) in a nucleotide molecule in a cell or in a test tube.

DNA-Targeting RNA Molecules

The "guide sequence portion" of an RNA molecule refers to a nucleotide sequence that is capable of hybridizing to a specific target DNA sequence, e.g., the guide sequence portion has a nucleotide sequence which is partially or fully complementary to the DNA sequence being targeted along the length of the guide sequence portion. In some embodiments, the guide sequence portion is 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleotides in length, or approximately 17-50, 17-49, 17-48, 17-47, 17-46, 17-45, 17-44, 17-43, 17-42, 17-41, 17-40, 17-39, 17-38, 17-37, 17-36, 17-35, 17-34, 17-33, 17-31, 17-30, 17-29, 17-28, 17-27, 17-26, 17-25, 17-24, 17-22, 17-21, 18-25, 18-24, 18-23, 18-22, 18-21, 19-25, 19-24, 19-23, 19-22, 19-21, 19-20, 20-22, 18-20, 20-21, 21-22, or 17-20 nucleotides in length. The entire length of the guide sequence portion is fully complementary to the DNA sequence being targeted along the length of the guide sequence portion. The guide sequence portion may be part of an RNA molecule that can form a complex with a CRISPR nuclease with the guide sequence portion serving as the DNA targeting portion of the CRISPR complex. When the DNA molecule having the guide sequence portion is present contemporaneously with the CRISPR molecule the RNA molecule is capable of targeting the CRISPR nuclease to the specific target DNA sequence. Each possibility represents a separate embodiment. An RNA molecule can be custom designed to target any desired sequence. Accordingly, a molecule comprising a "guide sequence portion" is a type of targeting molecule. Throughout this application, the terms "guide molecule," "RNA guide molecule," "guide RNA molecule," and "gRNA molecule" are synonymous with a molecule comprising a guide sequence portion, and the term "spacer" is synonymous with a "guide sequence portion.

In embodiments of the present invention, the CRISPR nuclease has its greatest cleavage activity when used with an RNA molecule comprising a guide sequence portion having 17, 18, 19 20, 21, 22, 23, 24, 25, 26, 27, 28, 29, or 30 nucleotides.

A single-guide RNA (sgRNA) molecule may be used to direct a CRISPR nuclease to a desired target site. The single-guide RNA comprises a guide sequence portion as well as a scaffold portion. The scaffold portion interacts with a CRISPR nuclease and, together with a guide sequence portion, activates and targets the CRISPR nuclease to a desired target site. A scaffold portion may be further engineered, for example, to have a reduced size. For example, OMNI-103 CRISPR nuclease demonstrates on-target nuclease activity with a sgRNA molecule having an engineered scaffold portion that is only 79 nucleotides in length.

According to some aspects of the invention, the disclosed methods comprise a method of modifying a nucleotide sequence at a target site in a cell-free system or the genome of a cell comprising introducing into the cell the composition of any one of the embodiments described herein.

In some embodiments, the cell is a eukaryotic cell, preferably a mammalian cell or a plant cell.

According to some aspects of the invention, the disclosed methods comprise a use of any one of the compositions described herein for the treatment of a subject afflicted with a disease associated with a genomic mutation comprising modifying a nucleotide sequence at a target site in the genome of the subject.

According to some aspects of the invention, the disclosed methods comprise a method of treating subject having a mutation disorder comprising targeting any one of the compositions described herein to an allele associated with the mutation disorder.

In some embodiments, the mutation disorder is related to a disease or disorder selected from any of a neoplasia, age-related macular degeneration, schizophrenia, neurological, neurodegenerative, or movement disorder, Fragile X Syndrome, secretase-related disorders, prion-related disorders, ALS, addiction, autism, Alzheimer's Disease, neutropenia, inflammation-related disorders, Parkinson's Disease, blood and coagulation diseases and disorders, beta thalassemia, sickle cell anemia, cell dysregulation and oncology diseases and disorders, inflammation and immune-related diseases and disorders, metabolic, liver, kidney and protein diseases and disorders, muscular and skeletal diseases and disorders, dermatological diseases and disorders, neurological and neuronal diseases and disorders, and ocular diseases and disorders.

OMNI CRISPR Nuclease Domains

The characteristic targeted nuclease activity of a CRISPR nuclease is imparted by the various functions of its specific domains. In this application the OMNI-103 CRISPR nuclease domains are defined as Domain A, Domain B, Domain C, Domain D, Domain E, Domain F, Domain G, Domain H, Domain I, and Domain J.

The activity of each OMNI-103 CRISPR nuclease domain is described herein, with each domain activity providing aspects of the advantageous features of the nuclease.

Specifically, Domain A, Domain G, and Domain I form a structural unit of the OMNI CRISPR nuclease, which contains a nuclease active site that participates in DNA strand cleavage. The structural unit formed by Domain A, Domain G, and Domain I cleaves a DNA strand that is displaced by a guide RNA molecule binding at a double-stranded DNA target site.

Domain B is involved in initiating DNA cleavage activity upon the binding of the OMNI CRISPR nuclease to a target a DNA site.

Domain C, Domain D, Domain E, and Domain F bind a guide RNA molecule and participate in providing specificity for target site recognition.

Domain H contains a nuclease active site that participates in DNA strand cleavage. Domain H cleaves a DNA strand which a guide RNA molecule binds at a DNA target site.

Domain J is involved in providing PAM site specificity to the OMNI CRISPR nuclease, including aspects of PAM site interrogation and recognition. Domain J also performs topoisomerase activity.

Further description of other CRISPR nuclease domains and their general functions can be found in, inter alia, Mir et al., ACS Chem. Biol. (2019), Palermo et al., Quarterly Reviews of Biophysics (2018), Jiang and Doudna, Annual Review of Biophysics (2017), Nishimasu et al., Cell (2014) and Nishimasu et al., Cell (2015), incorporated herein by reference.

In one aspect of the invention, an amino acid sequence having similarity to an OMNI CRISPR nuclease domain may be utilized in the design and manufacture of a non-naturally occurring peptide, e.g. a CRISPR nuclease, such that the peptide displays the advantageous features of the OMNI CRISPR nuclease domain activity.

In an embodiment, such a peptide, e.g. a CRISPR nuclease, comprises an amino acid sequence that has at least 100%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% identity to the amino acid sequence of at least one of Domain A, Domain B, Domain C, Domain D, Domain E, Domain F, Domain G, Domain H, Domain I, or Domain J of the OMNI-103 CRISPR nuclease. In some embodiments, the peptide comprises at least one, at least two, at least three, at least four, at least five, at least six, at least seven, at least eight, at least nine, at least ten, or at least eleven amino acid sequences selected from the amino acid sequences having at least 100%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% identity to the amino acid sequences of Domain A, Domain B, Domain C, Domain D, Domain E, Domain F, Domain G, Domain H, Domain I, and Domain J of the OMNI-103 CRISPR nuclease. Each possibility represents a separate embodiment. In an embodiment, the peptide exhibits extensive amino acid variability relative to the full length OMNI-103 CRISPR nuclease amino acid sequence outside of an amino acid sequence having at least 100%, 99.5%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% identity to the amino acid sequence of at least one of Domain A, Domain B, Domain C, Domain D, Domain E, Domain F, Domain G, Domain H, Domain I, or Domain J of the OMNI-103 CRISPR nuclease. In an embodiment, the peptide comprises an intervening amino acid sequence between two domain sequences. In an embodiment, the intervening amino acid sequence is 1-10, 10-20, 20-40, 40-50, 50-60, 80-100, 100-150, 150-200, 200-250, up to 100, up to 200 or up to 300 amino acids in length. Each possibility represents a separate embodiment. In an embodiment, the intervening sequence is a linker sequence. In an embodiment, a CRISPR nuclease comprises multiple domains from an OMNI CRISPR nuclease, and the domains are preferably organized in alphabetical order from the N-terminus to the C-terminus of the CRISPR nuclease. For example, a CRISPR nuclease comprising Domain A, Domain E, and Domain I of OMNI-103, the order of those domains in the CRISPR nuclease sequence would be Domain A, Domain E, and finally Domain I, with the possibility of intervening sequences on either end or both ends of each domain.

In one aspect of the invention, an amino acid sequence encoding any one of the domains of an OMNI CRISPR nuclease described herein may comprise one or more amino acid substitutions relative to the original OMNI CRISPR nuclease domain sequence. The amino acid substitution may be a conservative substitution, i.e. substitution for an amino acid having similar chemical properties as the original amino acid. For example, a positively charged amino acid may be substituted for an alternate positively charged amino acid, e.g. an arginine residue may be substituted for a lysine residue, or a polar amino acid may be substituted for a different polar amino acid. Conservative substitutions are more tolerable, and the amino acid sequence encoding any one of the domains of the OMNI CRISPR nuclease may contain as many as 10% of such substitutions. The amino acid substitution may be a radical substitution, i.e. substitution for an amino acid having different chemical properties as the original amino acid. For example, a positively charged amino acid may be substituted for a negatively charged amino acid, e.g. an arginine residue may be substituted for a glutamic acid residue, or a polar amino acid may be substituted for a non-polar amino acid. The amino acid substitution may be a semi-conservative substitution, or the amino acid substitution may be to any other amino acid. The substitution may alter the activity relative to the original OMNI CRISPR nuclease domain function e.g. reduce catalytic nuclease activity.

According to some aspects of the invention, the disclosed compositions comprise a non-naturally occurring composition comprising a CRISPR nuclease, wherein the CRISPR nuclease comprises an amino acid sequence corresponding to the amino acid sequence of at least one of Domain A, Domain B, Domain C, Domain D, Domain E, Domain F, Domain G, Domain H, Domain I, or Domain J of the OMNI-103 CRISPR nuclease. The amino acid range of each domain within its respective OMNI CRISPR nuclease amino acid sequence is provided in Supplemental Table 1. In some embodiments of the invention, the CRISPR nuclease comprises at least one, at least two, at least three, at least four, or at least five amino acid sequences, wherein each amino acid sequence corresponds to any one of the amino acid sequences Domain A, Domain B, Domain C, Domain D, Domain E, Domain F, Domain G, Domain H, Domain I, or Domain J of the OMNI-103 CRISPR nuclease. Accordingly, the CRISPR nuclease may include any combination of amino acid sequences that corresponds to any of Domain A, Domain B, Domain C, Domain D, Domain E, Domain F, Domain G, Domain H, Domain I, or Domain J of the OMNI CRISPR nuclease. In some embodiments, the amino acid sequence is at least 100-250, 250-500, 500-1000, 1000-1500, 1000-1700, or 1000-2000 amino acids in length.

Diseases and Therapies

Certain embodiments of the invention target a nuclease to a specific genetic locus associated with a disease or disorder as a form of gene editing, method of treatment, or therapy. For example, to induce editing or knockout of a gene, a novel nuclease disclosed herein may be specifically targeted to a pathogenic mutant allele of the gene using a custom designed guide RNA molecule. The guide RNA molecule is preferably designed by first considering the PAM requirement of the nuclease, which as shown herein is also dependent on the system in which the gene editing is being performed. For example, a guide RNA molecule designed to target an OMNI-103 nuclease to a target site is designed to contain a spacer region complementary to a DNA strand of a DNA double-stranded region that neighbors a OMNI-103 PAM sequence, e.g. "NNRRHY" or "NNRACT" or "NNRVCT." The guide RNA molecule is further preferably designed to contain a spacer region (i.e. the region of the guide RNA molecule having complementarity to the target allele) of sufficient and preferably optimal length in order to increase specific activity of the nuclease and reduce off-target effects.

As a non-limiting example, the guide RNA molecule may be designed to target the nuclease to a specific region of a mutant allele, e.g. near the start codon, such that upon DNA damage caused by the nuclease a non-homologous end joining (NHEJ) pathway is induced and leads to silencing of the mutant allele by introduction of frameshift mutations. This approach to guide RNA molecule design is particularly useful for altering the effects of dominant negative mutations and thereby treating a subject. As a separate non-limiting example, the guide RNA molecule may be designed to target a specific pathogenic mutation of a mutated allele, such that upon DNA damage caused by the nuclease a homology directed repair (HDR) pathway is induced and leads to template mediated correction of the mutant allele. This approach to guide RNA molecule design is particularly useful for altering haploinsufficiency effects of a mutated allele and thereby treating a subject.

Non-limiting examples of specific genes which may be targeted for alteration to treat a disease or disorder are presented herein below. Specific disease-associated genes and mutations that induce a mutation disorder are described in the literature. Such mutations can be used to design a DNA-targeting RNA molecule to target a CRISPR composition to an allele of the disease associated gene, where the CRISPR composition causes DNA damage and induces a DNA repair pathway to alter the allele and thereby treat the mutation disorder.

Mutations in the ELANE gene are associated with neutropenia. Accordingly, without limitation, embodiments of the invention that target ELANE may be used in methods of treating subjects afflicted with neutropenia.

CXCR4 is a co-receptor for the human immunodeficiency virus type 1 (HIV-1) infection. Accordingly, without limitation, embodiments of the invention that target CXCR4 may be used in methods of treating subjects afflicted with HIV-1 or conferring resistance to HIV-1 infection in a subject.

Programmed cell death protein 1 (PD-1) disruption enhances CAR-T cell mediated killing of tumor cells and PD-1 may be a target in other cancer therapies. Accordingly, without limitation, embodiments of the invention that target PD-1 may be used in methods of treating subjects afflicted with cancer. In an embodiment, the treatment is CAR-T cell therapy with T cells that have been modified according to the invention to be PD-1 deficient.

In addition, BCL11A is a gene that plays a role in the suppression of hemoglobin production. Globin production may be increased to treat diseases such as thalassemia or sickle cell anemia by inhibiting BCL11A. See for example, PCT International Publication No. WO 2017/077394A2; U.S. Publication No. US2011/0182867A1; Humbert et al. Sci. Transl. Med. (2019); and Canver et al. Nature (2015). Accordingly, without limitation, embodiments of the invention that target an enhancer of BCL11A may be used in methods of treating subjects afflicted with beta thalassemia or sickle cell anemia.

Embodiments of the invention may also be used for targeting any disease-associated gene, for studying, altering, or treating any of the diseases or disorders listed in Table A or Table B below. Indeed, any disease-associated with a genetic locus may be studied, altered, or treated by using the nucleases disclosed herein to target the appropriate disease-associated gene, for example, those listed in U.S. Publication No. 2018/0282762A1 and European Patent No. EP3079726B1.

TABLE A

| Diseases, Disorders and their associated genes | |
|---|---|
| DISEASE/DISORDERS | GENE(S) |
| Neoplasia | PTEN; ATM; ATR; EGFR; ERBB2; ERBB3; ERBB4; Notch1; Notch2; Notch3; Notch4; AKT; AKT2; AKT3; HIF; HIF1a; HIF3a; Met; HRG; Bcl2; PPAR alpha; PPAR gamma; WT1 (Wilms Tumor); FGF Receptor Family members (5 members: 1, 2, 3, 4, 5); CDKN2a; APC; RB (retinoblastoma); MEN1; VHL; BRCA1; BRCA2; AR (Androgen Receptor); TSG101; IGF; IGF Receptor; Igf1 (4 variants); gf2 (3 variants); Igf 1 Receptor; Igf 2 Receptor; Bax; Bcl2; caspases family (9 members: 1, 2, 3, 4, 6, 7, 8, 9, 12); Kras; Apc |
| Age-related Macular Degeneration | Abcr; Ccl2; Cc2; cp (ceruloplasmin); Timp3; cathepsinD; Vldlr; Ccr2 |
| Schizophrenia | Neuregulin1 (Nrg1); Erb4 (receptor for Neuregulin); Complexin1 (Cplx1); Tph1 Tryptophan hydroxylase; Tph2 Tryptophan hydroxylase 2; Neurexin 1; GSK3; GSK3a; GSK3b |
| Neurological, Neuro degenerative, and Movement Disorders | 5-HTT (Slc6a4); COMT; DRD (Drd1a); SLC6A3; DAOA; DTNBP1; Dao (Dao1) |
| Trinucleotide Repeat Disorders | HTT (Huntington's Dx); SBMA/SMAX1/AR (Kennedy's Dx); FXN/X25 (Friedrich's Ataxia); ATX3 (Machado-Joseph's Dx); ATXN1 and ATXN2 (spinocerebellar ataxias); DMPK (myotonic dystrophy); Atrophin-1 and Atn1 (DRPLA Dx); CBP (Creb-BP-global instability); VLDLR (Alzheimer's); Atxn7; Atxn10 |
| Fragile X Syndrome | FMR2; FXR1; FXR2; mGLUR5 |
| Secretase Related Disorders | APH-1 (alpha and beta); Presenilin (Psen1); nicastrin (Ncstn); PEN-2 |
| Others | Nos1; Parp1; Nat1; Nat2 |
| Prion related disorders | Prp |
| ALS | SOD1; ALS2; STEX; FUS; TARDBP; VEGF (VEGF-a; VEGF-b; VEGF-c) |
| Addiction | Prkce (alcohol); Drd2; Drd4; ABAT (alcohol); GRIA2; Grm5; Grin1; Htr1b; Grin2a; Drd3; Pdyn; Gria1 (alcohol) |
| Autism | Mecp2; BZRAP1; MDGA2; Sema5A; Neurexin 1; Fragile X (FMR2 (AFF2); FXR1; FXR2; Mglur5) |
| Alzheimer's Disease | E1; CHIP; UCH; UBB; Tau; LRP; PICALM; Clusterin; PS1; SORL1; CR1; Vldlr; Uba1; Uba3; CHIP28 (Aqp1, Aquaporin1); Uchl1; Uchl3; APP |
| Inflammation | IL-10; IL-1 (IL-1a; IL-1b); IL-13; IL-17 (IL-17a (CTLA8); IL-17b; IL-17c; IL-17d; IL-17f); II-23; Cx3cr1; ptpn22; TNFa; NOD2/CARD15 for IBD; IL-6; IL-12 (IL-12a; IL-12b); CTLA4; Cx3cl1 |
| Parkinson's Disease | x-Synuclein; DJ-1; LRRK2; Parkin; PINK1 |

TABLE B

| Diseases, Disorders and their associated genes | |
|---|---|
| DISEASE CATEGORY | DISEASE AND ASSOCIATED GENES |
| Blood and coagulation diseases and disorders | Anemia (CDAN1, CDA1, RPS19, DBA, PKLR, PK1, NT5C3, UMPH1, PSN1, RHAG, RH50A, NRAMP2, SPTB, ALAS2, ANH1, ASB, ABCB7, ABC7, ASAT); Bare lymphocyte syndrome (TAPBP, TPSN, TAP2, ABCB3, PSF2, RING11, MHC2TA, C2TA, RFX5, RFXAP, RFX5), Bleeding disorders (TBXA2R, P2RX1, P2X1); Factor H and factor H-like 1 (HF1, CFH, HUS); Factor V and factor VIII (MCFD2); Factor VII deficiency (F7); Factor X deficiency (F10); Factor XI deficiency (F11); Factor XII deficiency (F12, HAF); Factor XIIIA deficiency (F13A1, F13A); Factor XIIIB deficiency (F13B); Fanconi anemia (FANCA, FACA, FA1, FA, FAA, FAAP95, FAAP90, FLJ34064, FANCB, FANCC, FACC, BRCA2, FANCD1, FANCD2, FANCD, FACD, FAD, FANCE, FACE, FANCF, XRCC9, FANCG, BRIP1, BACH1, FANCJ, PHF9, FANCL, FANCM, KIAA1596); Hemophagocytic lymphohistiocytosis disorders (PRF1, HPLH2, UNC13D, MUNC13-4, HPLH3, HLH3, FHL3); Hemophilia A (F8, F8C, HEMA); Hemophilia B (F9, HEMB), Hemorrhagic disorders (PI, ATT, F5); Leukocyde deficiencies and disorders (ITGB2, CD18, LCAMB, LAD, EIF2B1, EIF2BA, EIF2B2, EIF2B3, EIF2B5, LVWM, CACH, CLE, EIF2B4); Sickle cell anemia (HBB); Thalassemia (HBA2, HBB, HBD, LCRB, HBA1) |

TABLE B-continued

| Diseases, Disorders and their associated genes | |
|---|---|
| DISEASE CATEGORY | DISEASE AND ASSOCIATED GENES |
| Cell dysregulation and oncology diseases and disorders | B-cell non-Hodgkin lymphoma (BCL7A, BCL7); Leukemia (TAL1, TCL5, SCL, TAL2, FLT3, NBS1, NBS, ZNFN1A1, IK1, LYF1, HOXD4, HOX4B, BCR, CML, PHL, ALL, ARNT, KRAS2, RASK2, GMPS, AF10, ARHGEF12, LARG, KIAA0382, CALM, CLTH, CEBPA, CEBP, CHIC2, BTL, FLT3, KIT, PBT, LPP, NPM1, NUP214, D9S46E, CAN, CAIN, RUNX1, CBFA2, AML1, WHSC1L1, NSD3, FLT3, AF1Q, NPM1, NUMA1, ZNF145, PLZF, PML, MYL, STAT5B, AF10, CALM, CLTH, ARL11, ARLTS1, P2RX7, P2X7, BCR, CML, PHL, ALL, GRAF, NF1, VRNF, WSS, NFNS, PTPN11, PTP2C, SHP2, NS1, BCL2, CCND1, PRAD1, BCL1, TCRA, GATA1, GF1, ERYF1, NFE1, ABL1, NQO1, DIA4, NMOR1, NUP214, D9S46E, CAN, CAIN) |
| Inflammation and immune related diseases and disorders | AIDS (KIR3DL1, NKAT3, NKB1, AMB11, KIR3DS1, IFNG, CXCL12, SDF1); Autoimmune lymphoproliferative syndrome (TNFRSF6, APT1, FAS, CD95, ALPS1A); Combined immunodeficiency, (IL2RG, SCIDX1, SCIDX, IMD4); HIV-1 (CCL5, SCYA5, D17S136E, TCP228), HIV susceptibility or infection (IL10, CSIF, CMKBR2, CCR2, CMKBR5, CCCKR5 (CCR5)); Immunodeficiencies (CD3E, CD3G, AICDA, AID, HIGM2, TNFRSF5, CD40, UNG, DGU, HIGM4, TNFSF5, CD40LG, HIGM1, IGM, FOXP3, IPEX, AIID, XPID, PIDX, TNFRSF14B, TACI); Inflammation (IL-10, IL-1 (IL-1a, IL-1b), IL-13, IL-17 (IL-17a (CTLA8), IL-17b, IL-17c, IL-17d, IL-17f), Il-23, Cx3cr1, ptpn22, TNFa, NOD2/CARD15 for IBD, IL-6, IL-12 (IL-12a, IL-12b), CTLA4, Cx3cl1); Severe combined immunodeficiencies (SCIDs)(JAK3, JAKL, DCLRE1C, ARTEMIS, SCIDA, RAG1, RAG2, ADA, PTPRC, CD45, LCA, IL7R, CD3D, T3D, IL2RG, SCIDX1, SCIDX, IMD4) |
| Metabolic, liver, kidney and protein diseases and disorders | Amyloid neuropathy (TTR, PALB); Amyloidosis (APOA1, APP, AAA, CVAP, AD1, GSN, FGA, LYZ, TTR, PALB); Cirrhosis (KRT18, KRT8, CIRH1A, NAIC, TEX292, KIAA1988); Cystic fibrosis (CFTR, ABCC7, CF, MRP7); Glycogen storage diseases (SLC2A2, GLUT2, G6PC, G6PT, G6PT1, GAA, LAMP2, LAMPB, AGL, GDE, GBE1, GYS2, PYGL, PFKM); Hepatic adenoma, 142330 (TCF1, HNF1A, MODY3), Hepatic failure, early onset, and neurologic disorder (SCOD1, SCO1), Hepatic lipase deficiency (LIPC), Hepatoblastoma, cancer and carcinomas (CTNNB1, PDGFRL, PDGRL, PRLTS, AXIN1, AXIN, CTNNB1, TP53, P53, LFS1, IGF2R, MPRI, MET, CASP8, MCH5; Medullary cystic kidney disease (UMOD, HNFJ, FJHN, MCKD2, ADMCKD2); Phenylketonuria (PAH, PKU1, QDPR, DHPR, PTS); Polycystic kidney and hepatic disease (FCYT, PKHD1, ARPKD, PKD1, PKD2, PKD4, PKDTS, PRKCSH, G19P1, PCLD, SEC63) |
| Muscular/Skeletal diseases and disorders | Becker muscular dystrophy (DMD, BMD, MYF6), Duchenne Muscular Dystrophy (DMD, BMD); Emery-Dreifuss muscular dystrophy (LMNA, LMN1, EMD2, FPLD, CMD1A, HGPS, LGMD1B, LMNA, LMN1, EMD2, FPLD, CMD1A); Facioscapulohumeral muscular dystrophy (FSHMD1A, FSHD1A); Muscular dystrophy (FKRP, MDC1C, LGMD2I, LAMA2, LAMM, LARGE, KIAA0609, MDC1D, FCMD, TTID, MYOT, CAPN3, CANP3, DYSF, LGMD2B, SGCG, LGMD2C, DMDA1, SCG3, SGCA, ADL, DAG2, LGMD2D, DMDA2, SGCB, LGMD2E, SGCD, SGD, LGMD2F, CMD1L, TCAP, LGMD2G, CMD1N, TRIM32, HT2A, LGMD2H, FKRP, MDC1C, LGMD2I, TTN, CMD1G, TMD, LGMD2J, POMT1, CAV3, LGMD1C, SEPN1, SELN, RSMD1, PLEC1, PLTN, EBS1); Osteopetrosis (LRP5, BMND1, LRP7, LR3, OPPG, VBCH2, CLCN7, CLC7, OPTA2, OSTM1, GL, TCIRG1, TIRC7, OC116, OPTB1); Muscular atrophy (VAPB, VAPC, ALS8, SMN1, SMA1, SMA2, SMA3, SMA4, BSCL2, SPG17, GARS, SMAD1, CMT2D, HEXB, IGHMBP2, SMUBP2, CATF1, SMARD1) |
| Dermatological diseases and disorders | Albinisim (TYR, OCA2, TYRP1, SLC45A2, LYST), Ectodermal dysplasias (EDAR, EDARADD, WNT10A), Ehlers-Danlos syndrome (COL5A1, COL5A2, COL1A1, COL1A2, COL3A1, TNXB, ADAMTS2, PLOD1, FKBP14), Ichthyosis-associated disorders (FLG, STS, TGM1, ALOXE3/ALOX12B, KRT1, KRT10, ABCA12, KRT2, GJB2, TGM1, ABCA12, CYP4F22, ALOXE3, CERS3, NSHDL, EBP, MBTPS2, GJB2, SPINK5, AGHD5, PHYH, PEX7, ALDH3A2, ERCC2, ERCC3, GFT2H5, GBA), Incontinentia pigmenti (IKBKG, NEMO), Tuberous sclerosis (TSC1, TSC2), Premature aging syndromes (POLR3A, PYCR1, LMNA, POLD1, WRN, DMPK) |

TABLE B-continued

| Diseases, Disorders and their associated genes | |
|---|---|
| DISEASE CATEGORY | DISEASE AND ASSOCIATED GENES |
| Neurological and Neuronal diseases and disorders | ALS (SOD1, ALS2, STEX, FUS, TARDBP, VEGF (VEGF-a, VEGF-b, VEGF-c); Alzheimer disease (APP, AAA, CVAP, AD1, APOE, AD2, PSEN2, AD4, STM2, APBB2, FE65L1, NOS3, PLAU, URK, ACE, DCP1, ACE1, MPO, PACIP1, PAXIP1L, PTIP, A2M, BLMH, BMH, PSEN1, AD3); Autism (Mecp2, BZRAP1, MDGA2, Sema5A, Neurexin 1, GLO1, MECP2, RTT, PPMX, MRX16, MRX79, NLGN3, NLGN4, KIAA1260, AUTSX2); Fragile X Syndrome (FMR2, FXR1, FXR2, mGLUR5); Huntington's disease and disease like disorders (HD, IT15, PRNP, PRIP, JPH3, JP3, HDL2, TBP, SCA17); Parkinson disease (NR4A2, NURR1, NOT, TINUR, SNCAIP, TBP, SCA17, SNCA, NACP, PARK1, PARK4, DJ1, PARK7, LRRK2, PARK8, PINK1, PARK6, UCHL1, PARK5, SNCA, NACP, PARK1, PARK4, PRKN, PARK2, PDJ, DBH, NDUFV2); Rett syndrome (MECP2, RTT, PPMX, MRX16, MRX79, CDKL5, STK9, MECP2, RTT, PPMX, MRX16, MRX79, x-Synuclein, DJ-1); Schizophrenia (Neuregulin1 (Nrg1), Erb4 (receptor for Neuregulin), Complexin1 (Cplx1), Tph1 Tryptophan hydroxylase, Tph2, Tryptophan hydroxylase 2, Neurexin 1, GSK3, GSK3a, GSK3b, 5-HTT (Slc6a4), COMT, DRD (Drd1a), SLC6A3, DAOA, DTNBP1, Dao (Dao1)); Secretase Related Disorders (APH-1 (alpha and beta), Presenilin (Psen1), nicastrin, (Ncstn), PEN-2, Nos1, Parp1, Natl, Nat2); Trinucleotide Repeat Disorders (HTT (Huntington's Dx), SBMA/SMAX1/AR (Kennedy's Dx), FXN/X25 (Friedrich's Ataxia), ATX3 (Machado-Joseph's Dx), ATXN1 and ATXN2 (spinocerebellar ataxias), DMPK (myotonic dystrophy), Atrophin-1 and Atn1 (DRPLA Dx), CBP (Creb-BP-global instability), VLDLR (Alzheimer's), Atxn7, Atxn10) |
| Ocular diseases and disorders | Age-related macular degeneration (Abcr, Ccl2, Cc2, cp (ceruloplasmin), Timp3, cathepsinD, Vldlr, Ccr2); Cataract (CRYAA, CRYA1, CRYBB2, CRYB2, PITX3, BFSP2, CP49, CP47, CRYAA, CRYA1, PAX6, AN2, MGDA, CRYBA1, CRYB1, CRYGC, CRYG3, CCL, LIM2, MP19, CRYGD, CRYG4, BFSP2, CP49, CP47, HSF4, CTM, HSF4, CTM, MIP, AQP0, CRYAB, CRYA2, CTPP2, CRYBB1, CRYGD, CRYG4, CRYBB2, CRYB2, CRYGC, CRYG3, CCL, CRYAA, CRYA1, GJA8, CX50, CAE1, GJA3, CX46, CZP3, CAE3, CCM1, CAM, KRIT1); Corneal clouding and dystrophy (APOA1, TGFBI, CSD2, CDGG1, CSD, BIGH3, CDG2, TACSTD2, TROP2, M1S1, VSX1, RINX, PPCD, PPD, KTCN, COL8A2, FECD, PPCD2, PIP5K3, CFD); Cornea plana congenital (KERA, CNA2); Glaucoma (MYOC, TIGR, GLC1A, JOAG, GPOA, OPTN, GLC1E, FIP2, HYPL, NRP, CYP1B1, GLC3A, OPA1, NTG, NPG, CYP1B1, GLC3A); Leber congenital amaurosis (CRB1, RP12, CRX, CORD2, CRD, RPGRIP1, LCA6, CORD9, RPE65, RP20, AIPL1, LCA4, GUCY2D, GUC2D, LCA1, CORD6, RDH12, LCA3); Macular dystrophy (ELOVL4, ADMD, STGD2, STGD3, RDS, RP7, PRPH2, PRPH, AVMD, AOFMD, VMD2) |

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of and any combination of items it conjoins.

It should be understood that the terms "a" and "an" as used above and elsewhere herein refer to "one or more" of the enumerated components. It will be clear to one of ordinary skill in the art that the use of the singular includes the plural unless specifically stated otherwise. Therefore, the terms "a," "an" and "at least one" are used interchangeably in this application.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

It is understood that where a numerical range is recited herein, the present invention contemplates each integer between, and including, the upper and lower limits, unless otherwise stated.

In the description and claims of the present application, each of the verbs, "comprise," "include" and "have" and conjugates thereof, are used to indicate that the object or objects of the verb are not necessarily a complete listing of components, elements or parts of the subject or subjects of the verb. Other terms as used herein are meant to be defined by their well-known meanings in the art.

The terms "polynucleotide", "nucleotide", "nucleotide sequence", "nucleic acid" and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: coding or non-coding regions of a gene or gene fragment, loci (locus) defined from linkage analysis, exons, in Irons, messenger RNA (mRNA), transfer RNA, ribosomal RNA, short interfering RNA (siRNA), short-hairpin RNA (shRNA), micro-RNA (miRNA), ribozymes, cDNA, recombinant polynucleotides, branched polynucleotides, plasmids, vectors, isolated DNA of any sequence, isolated RNA of any sequence, nucleic acid probes, and primers, A polynucleotide may comprise one or more modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component.

The term "nucleotide analog" or "modified nucleotide" refers to a nucleotide that contains one or more chemical modifications (e.g., substitutions), in or on the nitrogenous base of the nucleoside (e.g., cytosine (C), thymine (T) or uracil (U), adenine (A) or guanine (G)), in or on the sugar moiety of the nucleoside (e.g., ribose, deoxyribose, modified ribose, modified deoxyribose, six-membered sugar analog, or open-chain sugar analog), or the phosphate. Each of the RNA sequences described herein may comprise one or more nucleotide analogs.

As used herein, the following nucleotide identifiers are used to represent a referenced nucleotide base(s):

| Nucleotide reference | Base(s) represented | | | |
|---|---|---|---|---|
| A | A | | | |
| C | | C | | |
| G | | | G | |
| T | | | | T |
| W | A | | | T |
| S | | C | G | |
| M | A | C | | |
| K | | | G | T |
| R | A | | G | |
| Y | | C | | T |
| B | | C | G | T |

-continued

| Nucleotide reference | Base(s) represented | | | |
|---|---|---|---|---|
| D | A | | G | T |
| H | A | C | | T |
| V | A | C | G | |
| N | A | C | G | T |

As used herein, the term "targeting sequence" or "targeting molecule" refers a nucleotide sequence or molecule comprising a nucleotide sequence that is capable of hybridizing to a specific target sequence, e.g., the targeting sequence has a nucleotide sequence which is at least partially complementary to the sequence being targeted along the length of the targeting sequence. The targeting sequence or targeting molecule may be part of a targeting RNA molecule that can form a complex with a CRISPR nuclease with the targeting sequence serving as the targeting portion of the CRISPR complex. When the molecule having the targeting sequence is present contemporaneously with the CRISPR molecule, the RNA molecule is capable of targeting the CRISPR nuclease to the specific target sequence. Each possibility represents a separate embodiment. A targeting RNA molecule can be custom designed to target any desired sequence.

The term "targets" as used herein, refers to preferential hybridization of a targeting sequence or a targeting molecule to a nucleic acid having a targeted nucleotide sequence. It is understood that the term "targets" encompasses variable hybridization efficiencies, such that there is preferential targeting of the nucleic acid having the targeted nucleotide sequence, but unintentional off-target hybridization in addition to on-target hybridization might also occur. It is understood that where an RNA molecule targets a sequence, a complex of the RNA molecule and a CRISPR nuclease molecule targets the sequence for nuclease activity.

In the context of targeting a DNA sequence that is present in a plurality of cells, it is understood that the targeting encompasses hybridization of the guide sequence portion of the RNA molecule with the sequence in one or more of the cells, and also encompasses hybridization of the RNA molecule with the target sequence in fewer than all of the cells in the plurality of cells. Accordingly, it is understood that where an RNA molecule targets a sequence in a plurality of cells, a complex of the RNA molecule and a CRISPR nuclease is understood to hybridize with the target sequence in one or more of the cells, and also may hybridize with the target sequence in fewer than all of the cells. Accordingly, it is understood that the complex of the RNA molecule and the CRISPR nuclease introduces a double strand break in relation to hybridization with the target sequence in one or more cells and may also introduce a double strand break in relation to hybridization with the target sequence in fewer than all of the cells. As used herein, the term "modified cells" refers to cells in which a double strand break is affected by a complex of an RNA molecule and the CRISPR nuclease as a result of hybridization with the target sequence, i.e. on-target hybridization.

As used herein the term "wild type" is a term of the art understood by skilled persons and means the typical form of an organism, strain, gene or characteristic as it occurs in nature as distinguished from mutant or variant forms. Accordingly, as used herein, where a sequence of amino acids or nucleotides refers to a wild type sequence, a variant refers to variant of that sequence, e.g., comprising substitutions, deletions, insertions. In embodiments of the present invention, an engineered CRISPR nuclease is a variant CRISPR nuclease comprising at least one amino acid modification (e.g., substitution, deletion, and/or insertion) compared to the CRISPR nuclease of any of the CRISPR nucleases indicated in Table 1.

The terms "non-naturally occurring" or "engineered" are used interchangeably and indicate human manipulation. The terms, when referring to nucleic acid molecules or polypeptides may mean that the nucleic acid molecule or the polypeptide is at least substantially free from at least one other component with which they are naturally associated in nature and as found in nature.

As used herein the term "amino acid" includes natural and/or unnatural or synthetic amino acids, including glycine and both the D or I, optical isomers, and amino acid analogs and peptidomimetics.

As used herein, "genomic DNA" refers to linear and/or chromosomal DNA and/or to plasmid or other extrachromosomal DNA sequences present in the cell or cells of interest. In some embodiments, the cell of interest is a eukaryotic cell. In some embodiments, the cell of interest is a prokaryotic cell. In some embodiments, the methods produce double-stranded breaks (DSBs) at pre-determined target sites in a genomic DNA sequence, resulting in mutation, insertion, and/or deletion of DNA sequences at the target site(s) in a genome.

"Eukaryotic" cells include, but are not limited to, fungal cells (such as yeast), plant cells, animal cells, mammalian cells and human cells.

The term "nuclease" as used herein refers to an enzyme capable of cleaving the phosphodiester bonds between the nucleotide subunits of nucleic acid. A nuclease may be isolated or derived from a natural source. The natural source may be any living organism. Alternatively, a nuclease may be a modified or a synthetic protein which retains the phosphodiester bond cleaving activity.

The term "PAM" as used herein refers to a nucleotide sequence of a target DNA located in proximity to the targeted DNA sequence and recognized by the CRISPR nuclease. The PAM sequence may differ depending on the nuclease identity.

The term "mutation disorder" or "mutation disease" as used herein refers to any disorder or disease that is related to dysfunction of a gene caused by a mutation. A dysfunctional gene manifesting as a mutation disorder contains a mutation in at least one of its alleles and is referred to as a "disease-associated gene." The mutation may be in any portion of the disease-associated gene, for example, in a regulatory, coding, or non-coding portion. The mutation may be any class of mutation, such as a substitution, insertion, or deletion. The mutation of the disease-associated gene may manifest as a disorder or disease according to the mechanism of any type of mutation, such as a recessive, dominant negative, gain-of-function, loss-of-function, or a mutation leading to haploinsufficiency of a gene product.

A skilled artisan will appreciate that embodiments of the present invention disclose RNA molecules capable of complexing with a nuclease, e.g. a CRISPR nuclease, such as to associate with a target genomic DNA sequence of interest next to a protospacer adjacent motif (PAM). The nuclease then mediates cleavage of target DNA to create a double-stranded break within the protospacer.

In embodiments of the present invention, a CRISPR nuclease and a targeting molecule form a CRISPR complex that binds to a target DNA sequence to effect cleavage of the target DNA sequence. A CRISPR nuclease may form a CRISPR complex comprising the CRISPR nuclease and RNA molecule without a further, separate tracrRNA molecule. Alternatively, CRISPR nucleases may form a CRISPR complex between the CRISPR nuclease, an RNA molecule, and a tracrRNA molecule.

The term "protein binding sequence" or "nuclease binding sequence" refers to a sequence capable of binding with a CRISPR nuclease to form a CRISPR complex. A skilled artisan will understand that a tracrRNA capable of binding with a CRISPR nuclease to form a CRISPR complex comprises a protein or nuclease binding sequence.

An "RNA binding portion" of a CRISPR nuclease refers to a portion of the CRISPR nuclease which may bind to an RNA molecule to form a CRISPR complex, e.g. the nuclease binding sequence of a tracrRNA molecule. An "activity portion" or "active portion" of a CRISPR nuclease refers to a portion of the CRISPR nuclease which effects a double strand break in a DNA molecule, for example when in complex with a DNA-targeting RNA molecule.

An RNA molecule may comprise a sequence sufficiently complementary to a tracrRNA molecule so as to hybridize to the tracrRNA via basepairing and promote the formation of a CRISPR complex. (See U.S. Pat. No. 8,906,616). In embodiments of the present invention, the RNA molecule may further comprise a portion having a tracr mate sequence.

In embodiments of the present invention, the targeting molecule may further comprise the sequence of a tracrRNA molecule. Such embodiments may be designed as a synthetic fusion of the guide portion of the RNA molecule (gRNA or crRNA) and the trans-activating crRNA (tracrRNA), together forming a single guide RNA (sgRNA). (See Jinek et al., Science (2012)). Embodiments of the present invention may also form CRISPR complexes utilizing a separate tracrRNA molecule and a separate RNA molecule comprising a guide sequence portion. In such embodiments the tracrRNA molecule may hybridize with the RNA molecule via base pairing and may be advantageous in certain applications of the invention described herein.

In embodiments of the present invention an RNA molecule may comprise a "nexus" region and/or "hairpin" regions which may further define the structure of the RNA molecule. (See Briner et al., Molecular Cell (2014)).

As used herein, the term "direct repeat sequence" refers to two or more repeats of a specific amino acid sequence of nucleotide sequence.

As used herein, an RNA sequence or molecule capable of "interacting with" or "binding" with a CRISPR nuclease refers to the RNA sequence or molecules ability to form a CRISPR complex with the CRISPR nuclease.

As used herein, the term "operably linked" refers to a relationship (i.e. fusion, hybridization) between two sequences or molecules permitting them to function in their intended manner. In embodiments of the present invention, when an RNA molecule is operably linked to a promoter, both the RNA molecule and the promotor are permitted to function in their intended manner.

As used herein, the term "heterologous promoter" refers to a promoter that does not naturally occur together with the molecule or pathway being promoted.

As used herein, a sequence or molecule has an X % "sequence identity" to another sequence or molecule if X % of bases or amino acids between the sequences of molecules are the same and in the same relative position. For example, a first nucleotide sequence having at least a 95% sequence identity with a second nucleotide sequence will have at least 95% of bases, in the same relative position, identical with the other sequence.

Nuclear Localization Sequences

The terms "nuclear localization sequence" and "NLS" are used interchangeably to indicate an amino acid sequence/peptide that directs the transport of a protein with which it is associated from the cytoplasm of a cell across the nuclear envelope barrier. The term "NLS" is intended to encompass not only the nuclear localization sequence of a particular peptide, but also derivatives thereof that are capable of directing translocation of a cytoplasmic polypeptide across the nuclear envelope barrier. NLSs are capable of directing nuclear translocation of a polypeptide when attached to the N-terminus, the C-terminus, or both the N- and C-termini of the polypeptide. In addition, a polypeptide having an NLS coupled by its N- or C-terminus to amino acid side chains located randomly along the amino acid sequence of the polypeptide will be translocated. Typically, an NLS consists of one or more short sequences of positively charged lysines or arginines exposed on the protein surface, but other types of NLS are known. Non-limiting examples of NLSs include an NLS sequence derived from: the SV40 virus large T-antigen, nucleoplasmin, c-myc, the hRNPAI M9 NLS, the IBB domain from importin-alpha, myoma T protein, human p53, mouse c-abl IV, influenza vims NS1, Hepatitis virus delta antigen, mouse Mx1 protein, human poly(ADP-ribose) polymerase, and the steroid hormone receptors (human) glucocorticoid.

Delivery

The CRISPR nuclease or CRISPR compositions described herein may be delivered as a protein, DNA molecules, RNA molecules, Ribonucleoproteins (RNP), nucleic acid vectors, or any combination thereof. In some embodiments, the RNA molecule comprises a chemical modification. Non-limiting examples of suitable chemical modifications include 2'-0-methyl (M), 2'-0-methyl, 3'phosphorothioate (MS) or 2'-0-methyl, 3'thioPACE (MSP), pseudouridine, and 1-methyl pseudo-uridine. Each possibility represents a separate embodiment of the present invention.

The CRISPR nucleases and/or polynucleotides encoding same described herein, and optionally additional proteins (e.g., ZFPs, TALENs, transcription factors, restriction enzymes) and/or nucleotide molecules such as guide RNA may be delivered to a target cell by any suitable means. The target cell may be any type of cell e.g., eukaryotic or prokaryotic, in any environment e.g., isolated or not, maintained in culture, in vitro, ex vivo, in vivo or in planta.

In some embodiments, the composition to be delivered includes mRNA of the nuclease and RNA of the guide. In some embodiments, the composition to be delivered includes mRNA of the nuclease, RNA of the guide and a donor template. In some embodiments, the composition to be delivered includes the CRISPR nuclease and guide RNA. In some embodiments, the composition to be delivered includes the CRISPR nuclease, guide RNA and a donor template for gene editing via, for example, homology directed repair. In some embodiments, the composition to be delivered includes mRNA of the nuclease, DNA-targeting RNA and the tracrRNA. In some embodiments, the composition to be delivered includes mRNA of the nuclease, DNA-targeting RNA and the tracrRNA and a donor template. In some embodiments, the composition to be delivered includes the CRISPR nuclease DNA-targeting RNA and the tracrRNA. In some embodiments, the composition to be delivered includes the CRISPR nuclease, DNA-targeting RNA and the tracrRNA and a donor template for gene editing via, for example, homology directed repair.

Any suitable viral vector system may be used to deliver RNA compositions. Conventional viral and non-viral based gene transfer methods can be used to introduce nucleic acids and/or CRISPR nuclease in cells (e.g., mammalian cells, plant cells, etc.) and target tissues. Such methods can also be used to administer nucleic acids encoding and/or CRISPR nuclease protein to cells in vitro. In certain embodiments, nucleic acids and/or CRISPR nuclease are administered for in vivo or ex vivo gene therapy uses. Non-viral vector delivery systems include naked nucleic acid, and nucleic acid complexed with a delivery vehicle such as a liposome or poloxamer. For a review of gene therapy procedures, see Anderson, Science (1992); Nabel and Felgner, TIBTECH (1993); Mitani and Caskey, TIBTECH (1993); Dillon, TIBTECH (1993); Miller, Nature (1992); Van Brunt, Biotechnology (1988); Vigne et al., Restorative Neurology and Neuroscience 8:35-36 (1995); Kremer and Perricaudet, British Medical Bulletin (1995); Haddada et al., Current Topics in Microbiology and Immunology (1995); and Yu et al., Gene Therapy 1:13-26 (1994).

Methods of non-viral delivery of nucleic acids and/or proteins include electroporation, lipofection, microinjection, biolistics, particle gun acceleration, virosomes, liposomes, immunoliposomes, lipid nanoparticles (LNPs), polycation or lipid: nucleic acid conjugates, artificial virions, and agent-enhanced uptake of nucleic acids or can be delivered to plant cells by bacteria or viruses (e.g., *Agrobacterium, Rhizobium* sp. NGR234, *Sinorhizoboiummeliloti, Mesorhizobium loti*, tobacco mosaic virus, potato virus X, cauliflower mosaic virus and cassava vein mosaic virus. See, e.g., Chung et al. Trends Plant Sci. (2006). Sonoporation using, e.g., the Sonitron 2000 system (Rich-Mar) can also be used for delivery of nucleic acids. Cationic-lipid mediated delivery of proteins and/or nucleic acids is also contemplated as an in vivo, ex vivo, or in vitro delivery method. See Zuris et al., Nat. Biotechnol. (2015), Coelho et al., N. Engl. J. Med. (2013); Judge et al., Mol. Ther. (2006); and Basha et al., Mol. Ther. (2011).

Non-viral vectors, such as transposon-based systems e.g. recombinant Sleeping Beauty transposon systems or recombinant PiggyBac transposon systems, may also be delivered to a target cell and utilized for transposition of a polynucleotide sequence of a molecule of the composition or a polynucleotide sequence encoding a molecule of the composition in the target cell.

Additional exemplary nucleic acid delivery systems include those provided by Amaxa® Biosystems (Cologne, Germany), Maxcyte, Inc. (Rockville, Md.), BTX Molecular Delivery Systems (Holliston, Mass.) and Copernicus Therapeutics Inc., (see for example U.S. Pat. No. 6,008,336). Lipofection is described in e.g., U.S. Pat. Nos. 5,049,386, 4,946,787; and 4,897,355) and lipofection reagents are sold commercially (e.g., Transfectam™, Lipofectin™ and Lipofectamine™ RNAiMAX). Cationic and neutral lipids that are suitable for efficient receptor-recognition lipofection of polynucleotides include those disclosed in PCT International Publication Nos. WO/1991/017424 and WO/1991/016024. Delivery can be to cells (ex vivo administration) or target tissues (in vivo administration).

The preparation of lipid: nucleic acid complexes, including targeted liposomes such as immunolipid complexes, is well known to one of skill in the art (see, e.g., Crystal, Science (1995); Blaese et al., Cancer Gene Ther. (1995); Behr et al., Bioconjugate Chem. (1994); Remy et al., Bioconjugate Chem. (1994); Gao and Huang, Gene Therapy (1995); Ahmad and Allen, Cancer Res., (1992); U.S. Pat. Nos. 4,186,183; 4,217,344; 4,235,871; 4,261,975; 4,485,054; 4,501,728; 4,774,085; 4,837,028; and 4,946,787).

Additional methods of delivery include the use of packaging the nucleic acids to be delivered into EnGeneIC delivery vehicles (EDVs). These EDVs are specifically delivered to target tissues using bispecific antibodies where one arm of the antibody has specificity for the target tissue and the other has specificity for the EDV. The antibody brings the EDVs to the target cell surface and then the EDV is brought into the cell by endocytosis. Once in the cell, the contents are released (see MacDiamid et al., Nature Biotechnology (2009)).

Delivery vehicles include, but are not limited to, bacteria, preferably non-pathogenic, vehicles, nanoparticles, exosomes, microvesicles, gene gun delivery, for example, by attachment of a composition to a gold particle which is fired into a cell using via a "gene-gun", viral vehicles, including but not limited to lentiviruses, AAV, and retroviruses), virus-like particles (VLPs). large VLPs (LVLPs), lentivirus-like particles, transposons, viral vectors, naked vectors, DNA, or RNA, among other delivery vehicles known in the art.

The delivery of a CRISPR nuclease and/or a polynucleotide encoding the CRISPR nuclease, and optionally additional nucleotide molecules and/or additional proteins or peptides, may be performed by utilizing a single delivery vehicle or method or a combination of different delivery vehicles or methods. For example, a CRISPR nuclease may be delivered to a cell utilizing an LNP, and a crRNA molecule and tracrRNA molecule may be delivered to the cell utilizing AAV. Alternatively, a CRISPR nuclease may be delivered to a cell utilizing an AAV particle, and a crRNA molecule and tracrRNA molecule may be delivered to the cell utilizing a separate AAV particle, which may be advantageous due to size limitations.

The use of RNA or DNA viral based systems for the delivery of nucleic acids take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of nucleic acids include, but are not limited to, recombinant retroviral, lentivirus, adenoviral, adeno-associated, vaccinia and herpes simplex virus vectors for gene transfer. However, an RNA virus is preferred for delivery of the RNA compositions described herein. Additionally, high transduction efficiencies have been observed in many different cell types and target tissues. Nucleic acid of the invention may be delivered by non-integrating lentivirus. Optionally, RNA delivery with Lentivirus is utilized. Optionally the lentivirus includes mRNA of the nuclease, RNA of the guide. Optionally the lentivirus includes mRNA of the nuclease, RNA of the guide and a donor template. Optionally, the lentivirus includes the nuclease protein, guide RNA. Optionally, the lentivirus includes the nuclease protein, guide RNA and/or a donor template for gene editing via, for example, homology directed repair. Optionally the lentivirus includes mRNA of the nuclease, DNA-targeting RNA, and the tracrRNA. Optionally the lentivirus includes mRNA of the nuclease, DNA-targeting RNA, and the tracrRNA, and a donor template. Optionally, the lentivirus includes the nuclease protein, DNA-targeting RNA, and the tracrRNA. Optionally, the lentivirus includes the nuclease protein, DNA-targeting RNA, and the tracrRNA, and a donor template for gene editing via, for example, homology directed repair.

As mentioned above, the compositions described herein may be delivered to a target cell using a non-integrating lentiviral particle method, e.g. a LentiFlash® system. Such a method may be used to deliver mRNA or other types of RNAs into the target cell, such that delivery of the RNAs to the target cell results in assembly of the compositions described herein inside of the target cell. See also PCT International Publication Nos. WO2013/014537, WO2014/016690, WO2016185125, WO2017194902, and WO2017194903.

The tropism of a retrovirus can be altered by incorporating foreign envelope proteins, expanding the potential target population of target cells. Lentiviral vectors are retroviral vectors capable of transducing or infecting non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher Panganiban, J. Virol. (1992); Johann et al., J. Virol. (1992); Sommerfelt et al., Virol. (1990); Wilson et al., J. Virol. (1989); Miller et al., J. Virol. (1991); PCT International Publication No. WO/1994/026877A1).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., Blood (1995); Kohn et al., Nat. Med. (1995); Malech et al., PNAS (1997)). PA317/pLASN was the first therapeutic vector used in a gene therapy trial. (Blaese et al., Science (1995)). Transduction efficiencies of 50% or greater have been observed for MFG-S packaged vectors. (Ellem et al., Immunol Immunother. (1997); Dranoff et al., Hum. Gene Ther. (1997).

Packaging cells are used to form virus particles that are capable of infecting a host cell. Such cells include 293 cells, which package adenovirus, AAV, and psi.2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additionally, AAV can be produced at clinical scale using baculovirus systems (see U.S. Pat. No. 7,479,554).

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., Proc. Natl. Acad. Sci. USA (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to non-viral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector. In some embodiments, delivery of mRNA in vivo and ex vivo, and RNPs delivery may be utilized.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with an RNA composition, and re-infused back into the subject organism (e.g., patient). Various cell types suitable for ex vivo transfection are well known to those of skill in the art (see, e.g., Freshney, "Culture of Animal Cells, A Manual of Basic Technique and Specialized Applications (6th edition, 2010)) and the references cited therein for a discussion of how to isolate and culture cells from patients).

Suitable cells include but not limited to eukaryotic and prokaryotic cells and/or cell lines. Non-limiting examples of such cells or cell lines generated from such cells include COS, CHO (e.g., CHO-S, CHO-K1, CHO-DG44, CHO-DUXB11, CHO-DUKX, CHOKISV), VERO, MDCK, WI38, V79, B14AF28-G3, BHK, HaK, NSO, SP2/0-Ag14, HeLa, HEK293 (e.g., HEK293-F, HEK293-H, HEK293-T), and perC6 cells, any plant cell (differentiated or undifferentiated) as well as insect cells such as Spodopterafugiperda (Sf), or fungal cells such as *Saccharomyces, Pichia* and *Schizosaccharomyces*. In certain embodiments, the cell line is a CHO-K1, MDCK or HEK293 cell line. Additionally, primary cells may be isolated and used ex vivo for reintroduction into the subject to be treated following treatment with the nucleases (e.g. ZFNs or TALENs) or nuclease systems (e.g. CRISPR). Suitable primary cells include peripheral blood mononuclear cells (PBMC), and other blood cell subsets such as, but not limited to, CD4+ T cells or CD8+ T cells. Suitable cells also include stem cells such as, by way of example, embryonic stem cells, induced pluripotent stem cells, hematopoietic stem cells (CD34+), neuronal stem cells and mesenchymal stem cells.

In one embodiment, stem cells are used in ex vivo procedures for cell transfection and gene therapy. The advantage to using stem cells is that they can be differentiated into other cell types in-vitro or can be introduced into a mammal (such as the donor of the cells) where they will engraft in the bone marrow. Methods for differentiating CD34+ cells in vitro into clinically important immune cell types using cytokines such a GM-CSF, IFN-gamma. and TNF-alpha are known (as a non-limiting example see, Inaba et al., J. Exp. Med. (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and lad (differentiated antigen presenting cells) (as a non-limiting example see Inaba et al., J. Exp. Med. (1992)). Stem cells that have been modified may also be used in some embodiments.

Notably, any one of the CRISPR nucleases described herein may be suitable for genome editing in post-mitotic cells or any cell which is not actively dividing, e.g., arrested cells. Examples of post-mitotic cells which may be edited using a CRISPR nuclease of the present invention include, but are not limited to, myocyte, a cardiomyocyte, a hepatocyte, an osteocyte and a neuron.

Vectors (e.g., retroviruses, liposomes, etc.) containing therapeutic RNA compositions can also be administered directly to an organism for transduction of cells in vivo. Alternatively, naked RNA or mRNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Vectors suitable for introduction of transgenes into immune cells (e.g., T-cells) include non-integrating lentivirus vectors. See, for example, U.S. Patent Publication No. 2009/0117617.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., Remington's Pharmaceutical Sciences, 17th ed., 1989).

DNA Repair by Homologous Recombination

The term "homology-directed repair" or "HDR" refers to a mechanism for repairing DNA damage in cells, for example, during repair of double-stranded and single-stranded breaks in DNA. HDR requires nucleotide sequence homology and uses a "nucleic acid template" (nucleic acid template or donor template used interchangeably herein) to repair the sequence where the double-stranded or single break occurred (e.g., DNA target sequence). This results in the transfer of genetic information from, for example, the nucleic acid template to the DNA target sequence. HDR may result in alteration of the DNA target sequence (e.g., insertion, deletion, mutation) if the nucleic acid template sequence differs from the DNA target sequence and part or all of the nucleic acid template polynucleotide or oligonucleotide is incorporated into the DNA target sequence. In some embodiments, an entire nucleic acid template polynucleotide, a portion of the nucleic acid template polynucleotide, or a copy of the nucleic acid template is integrated at the site of the DNA target sequence.

The terms "nucleic acid template" and "donor", refer to a nucleotide sequence that is inserted or copied into a genome. The nucleic acid template comprises a nucleotide sequence, e.g., of one or more nucleotides, that will be added to or will template a change in the target nucleic acid or may be used to modify the target sequence. A nucleic acid template sequence may be of any length, for example between 2 and 10,000 nucleotides in length (or any integer value there between or there above), preferably between about 100 and 1,000 nucleotides in length (or any integer there between), more preferably between about 200 and 500 nucleotides in length. A nucleic acid template may be a single stranded nucleic acid, a double stranded nucleic acid. In some embodiment, the nucleic acid template comprises a nucleotide sequence, e.g., of one or more nucleotides, that corresponds to wild type sequence of the target nucleic acid, e.g., of the target position. In some embodiment, the nucleic acid template comprises a ribonucleotide sequence, e.g., of one or more ribonucleotides, that corresponds to wild type sequence of the target nucleic acid, e.g., of the target position. In some embodiment, the nucleic acid template comprises modified ribonucleotides.

Insertion of an exogenous sequence (also called a "donor sequence," donor template" or "donor"), for example, for correction of a mutant gene or for increased expression of a wild type gene can also be carried out. It will be readily apparent that the donor sequence is typically not identical to the genomic sequence where it is placed. A donor sequence can contain a non-homologous sequence flanked by two regions of homology to allow for efficient HDR at the location of interest. Additionally, donor sequences can comprise a vector molecule containing sequences that are not homologous to the region of interest in cellular chromatin. A donor molecule can contain several, discontinuous regions of homology to cellular chromatin. For example, for targeted insertion of sequences not normally present in a region of interest, said sequences can be present in a donor nucleic acid molecule and flanked by regions of homology to sequence in the region of interest.

The donor polynucleotide can be DNA or RNA, single-stranded and/or double-stranded and can be introduced into a cell in linear or circular form. See, e.g., U.S. Patent Publication Nos. 2010/0047805; 2011/0281361; 2011/0207221; and 2019/0330620. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang and Wilson, Proc. Natl. Acad. Sci. USA (1987); Nehls et al., Science (1996). Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

Accordingly, embodiments of the present invention using a donor template for repair may use a DNA or RNA, single-stranded and/or double-stranded donor template that can be introduced into a cell in linear or circular form. In embodiments of the present invention a gene-editing composition comprises: (1) an RNA molecule comprising a guide sequence to affect a double strand break in a gene prior to repair and (2) a donor RNA template for repair, the RNA molecule comprising the guide sequence is a first RNA molecule and the donor RNA template is a second RNA molecule. In some embodiments, the guide RNA molecule and template RNA molecule are connected as part of a single molecule.

A donor sequence may also be an oligonucleotide and be used for gene correction or targeted alteration of an endogenous sequence. The oligonucleotide may be introduced to the cell on a vector, may be electroporated into the cell, or may be introduced via other methods known in the art. The oligonucleotide can be used to 'correct' a mutated sequence in an endogenous gene (e.g., the sickle mutation in beta globin), or may be used to insert sequences with a desired purpose into an endogenous locus.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by recombinant viruses (e.g., adenovirus, AAV, herpesvirus, retrovirus, lentivirus and integrase defective lentivirus (IDLV)).

The donor is generally inserted so that its expression is driven by the endogenous promoter at the integration site, namely the promoter that drives expression of the endogenous gene into which the donor is inserted. However, it will be apparent that the donor may comprise a promoter and/or enhancer, for example a constitutive promoter or an inducible or tissue specific promoter.

The donor molecule may be inserted into an endogenous gene such that all, some or none of the endogenous gene is expressed. For example, a transgene as described herein may be inserted into an endogenous locus such that some (N-terminal and/or C-terminal to the transgene) or none of the endogenous sequences are expressed, for example as a fusion with the transgene. In other embodiments, the transgene (e.g., with or without additional coding sequences such as for the endogenous gene) is integrated into any endogenous locus, for example a safe-harbor locus, for example a CCR5 gene, a CXCR4 gene, a PPPIR12c (also known as AAVS1) gene, an albumin gene or a Rosa gene. See, e.g., U.S. Pat. Nos. 7,951,925 and 8,110,379; U.S. Publication Nos. 2008/0159996; 20100/0218264; 2010/0291048; 2012/0017290; 2011/0265198; 2013/0137104; 2013/0122591; 2013/0177983 and 2013/0177960 and U.S. Provisional Application No. 61/823,689).

When endogenous sequences (endogenous or part of the transgene) are expressed with the transgene, the endogenous sequences may be full-length sequences (wild type or mutant) or partial sequences. Preferably the endogenous sequences are functional. Non-limiting examples of the function of these full length or partial sequences include increasing the serum half-life of the polypeptide expressed by the transgene (e.g., therapeutic gene) and/or acting as a carrier.

Furthermore, although not required for expression, exogenous sequences may also include transcriptional or translational regulatory sequences, for example, promoters, enhancers, insulators, internal ribosome entry sites, sequences encoding 2A peptides and/or polyadenylation signals.

In certain embodiments, the donor molecule comprises a sequence selected from the group consisting of a gene encoding a protein (e.g., a coding sequence encoding a protein that is lacking in the cell or in the individual or an alternate version of a gene encoding a protein), a regulatory sequence and/or a sequence that encodes a structural nucleic acid such as a microRNA or siRNA.

For the foregoing embodiments, each embodiment disclosed herein is contemplated as being applicable to each of the other disclosed embodiment. For example, it is understood that any of the RNA molecules or compositions of the present invention may be utilized in any of the methods of the present invention.

As used herein, all headings are simply for organization and are not intended to limit the disclosure in any manner. The content of any individual section may be equally applicable to all sections.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Generally, the nomenclature used herein, and the laboratory procedures utilized in the present invention include molecular, biochemical, microbiological and recombinant DNA techniques. Such techniques are thoroughly explained in the literature. See, for example, Sambrook et al., "Molecular Cloning: A laboratory Manual" (1989); Ausubel, R. M. (Ed.), "Current Protocols in Molecular Biology" Volumes I-III (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (Eds.), "Genome Analysis: A Laboratory Manual Series", Vols. 1-4, Cold Spring Harbor Laboratory Press, New York (1998); Methodologies as set forth in U.S. Pat. Nos. 4,666,828; 4,683,202; 4,801,531; 5,192,659 and 5,272,057; Cellis, J. E. (Ed.), "Cell Biology: A Laboratory Handbook", Volumes I-III (1994); Freshney, "Culture of Animal Cells-A Manual of Basic Technique" Third Edition, Wiley-Liss, N.Y. (1994); Coligan J. E. (Ed.), "Current Protocols in Immunology" Volumes I-III (1994); Stites et al. (Eds.), "Basic and Clinical Immunology" (8th Edition), Appleton & Lange, Norwalk, CT (1994); Mishell and Shiigi (Eds.), "Strategies for Protein Purification and Characterization-A Laboratory Course Manual" CSHL Press (1996); Clokie and Kropinski (Eds.), "Bacteriophage Methods and Protocols", Volume 1: Isolation, Characterization, and Interactions (2009), all of which are incorporated by reference. Other general references are provided throughout this document.

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

EXPERIMENTAL DETAILS

Examples are provided below to facilitate a more complete understanding of the invention. The following examples illustrate the exemplary modes of making and practicing the invention. However, the scope of the invention is not limited to specific embodiments disclosed in these Examples, which are for purposes of illustration only.

Example 1: OMNI-103 CRISPR Nuclease

CRISPR repeat (crRNA), trans-activating RNA (tracrRNA), nuclease polypeptide (OMNI), and protospacer adjacent motif (PAM) sequences were predicted from different metagenomic databases of sequences of environmental samples.

Construction of OMNI Nuclease Polypeptides

For construction of novel nuclease polypeptides (OMNIs), the open reading frame of several identified OMNIs were codon optimized for human cell line expression. The ORF was cloned into the bacterial expression plasmid pET9a and into the mammalian expression plasmid pmOMNI (Table 4).

Prediction and Construction of sgRNA

For each OMNI the single guide RNA (sgRNA) was predicted by detection of the CRISPR repeat array sequence and a tracrRNA in the respective bacterial genome. The native pre-mature crRNA and tracrRNA sequences were connected in silico with a tetra-loop 'gaaa' sequence and the secondary structure elements of the duplex were predicted using an RNA secondary structure prediction tool.

Figure 1B:

The predicted secondary structures of the full duplex RNA elements (crRNA-tracrRNA chimera) was used for identification of possible tracrRNA sequences for the design of a sgRNA. Several possible sgRNA scaffolds versions were constructed by shortening the duplex at the upper stem at different locations (OMNI-103 sgRNA designs are listed in Table 2). Additionally, to overcome potential transcriptional and structural constraints and to assess the plasticity of the sgRNA scaffold in the human cellular environmental context, small changes in the nucleotide sequence of the possible sgRNA were made in some cases (FIG. 1, Table 2). Finally, up to three versions of possible designed scaffolds were synthesized for each OMNI and connected downstream to a 22-nucleotide universal unique spacer sequence (T2, SEQ ID NO: 135) and cloned into a bacterial expressing plasmid under an inducible T7 promoter combined with a U6 promoter for mammalian expression (pShuttleGuide, Table 4).

```
                                    (SEQ ID NO: 135)
          T2 - GGAAGAGCAGAGCCTTGGTCTC
```

In-Vitro Depletion Assay by TXTL

Figure 4A:
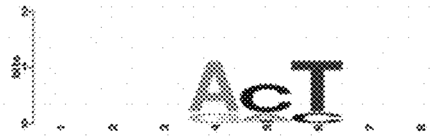
Figure 4A:
Figure 5B:
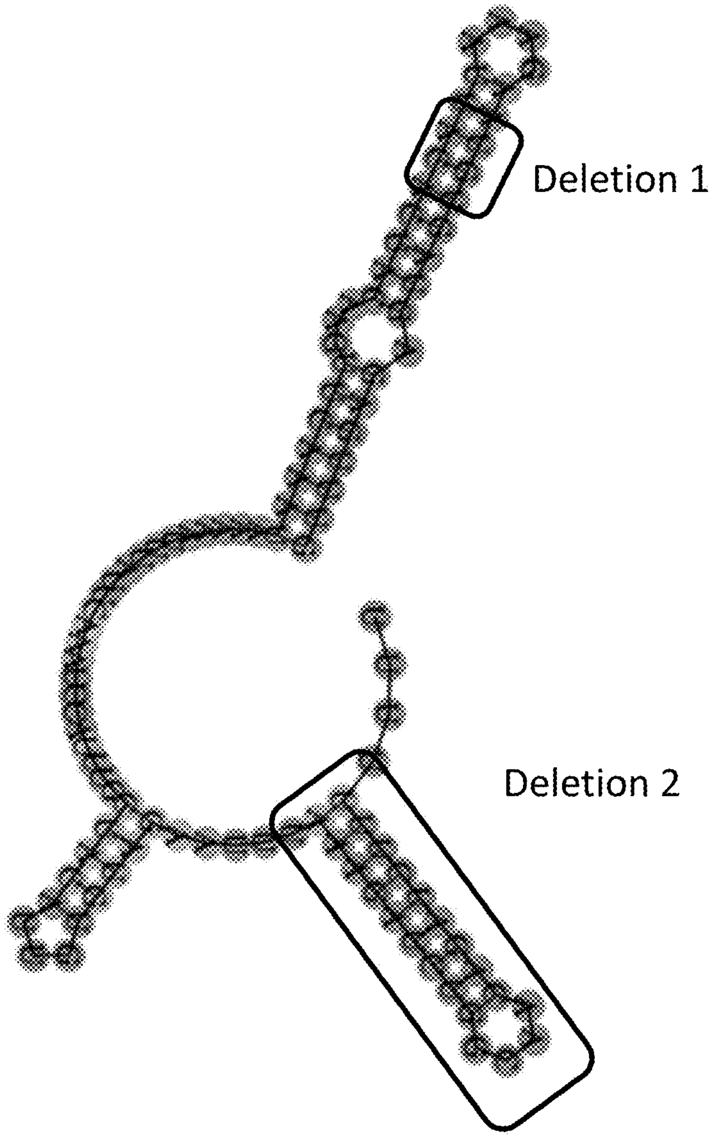
Figure 5C:
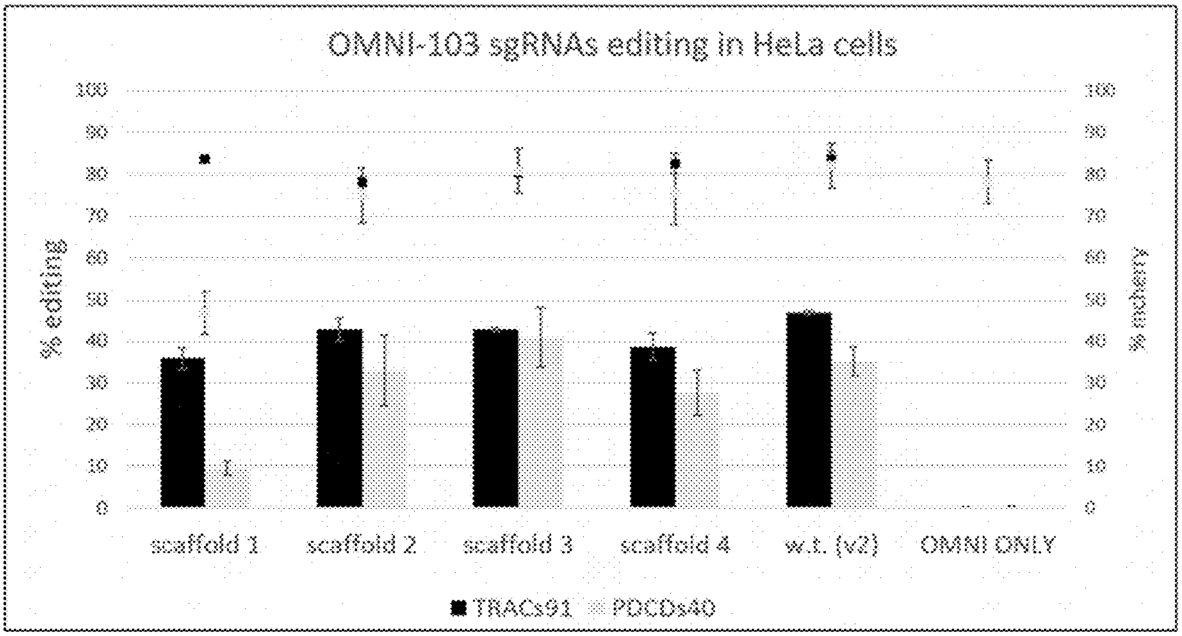
Figure 6A:
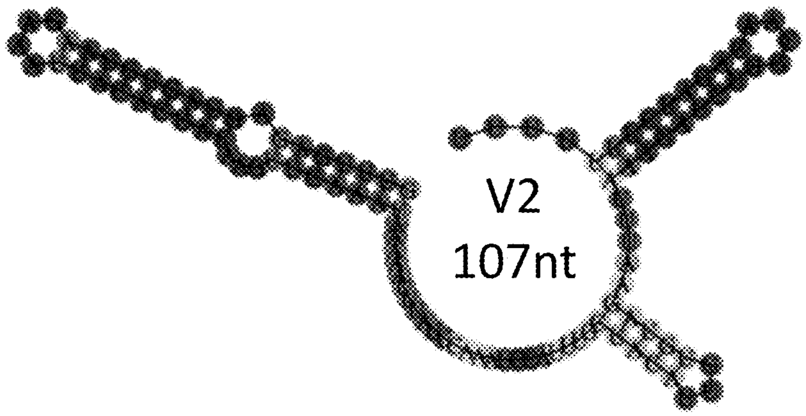
FIGS. 6A-6F. The predicted secondary structures of the sgRNA listed in Table 3.
Figure 6B:
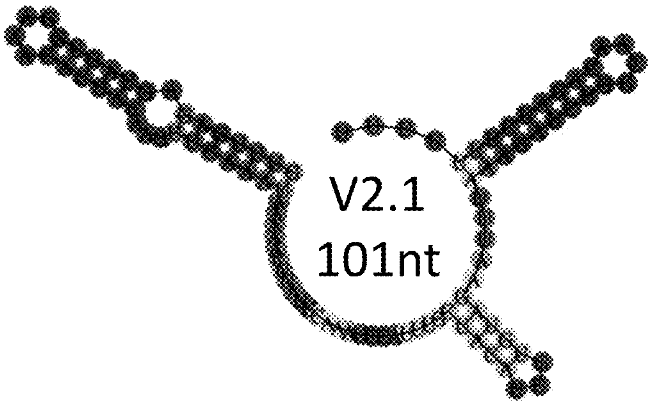
Figure 6C:
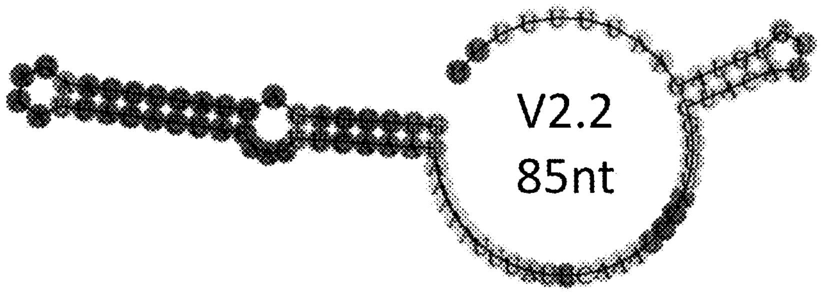
Figure 6D:
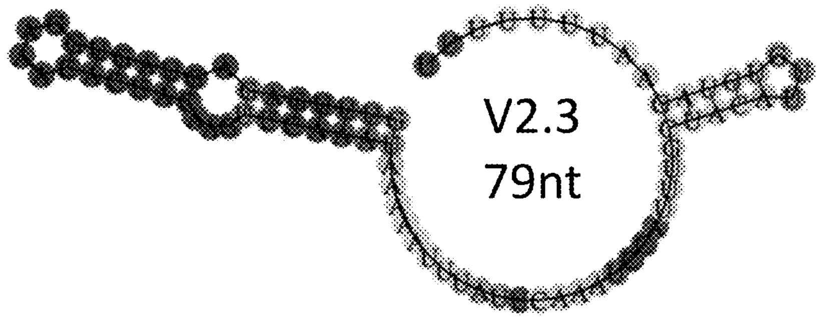
Figure 6E:
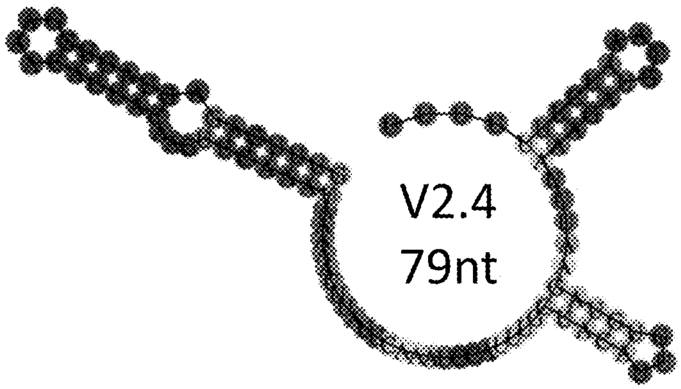
Figure 6F:
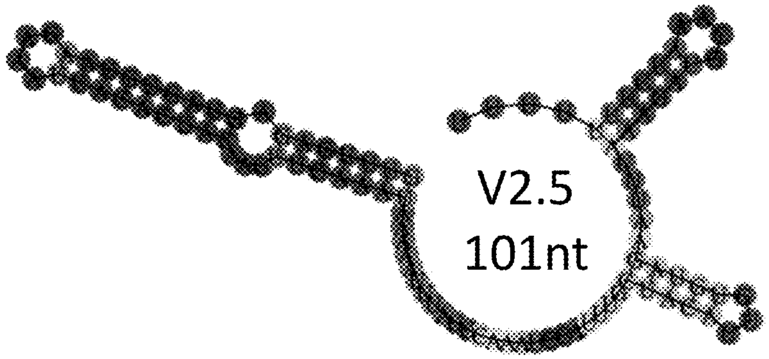

Depletion of PAM sequences in vitro was followed as described by Maxwell et al, Methods. 2018. Briefly, linear DNA expressing the OMNI nucleases and an sgRNA under T7 promoter were added to a cell-free transcription-translation in vitro system (TXTL mix, Arbor Bioscience) together with a linear construct expressing T7 polymerase. RNA expression and protein translation by the TXTL mix result in the formation of a ribonucleoprotein (RNP) complex. Since linear DNA was used, Chi6 DNA sequences were added to the TXTL reaction mix to inhibit the exonuclease activity of RecBCD, thereby protecting the linear DNA from degradation. The sgRNA spacer is designed to target a library of plasmids containing the target protospacer (pbPOS T2 library, Table 4) flanked by an 8N randomized set of potential PAM sequences. Depletion of PAM sequences from the library was measured by high-throughput sequencing using PCR to add the necessary adapters and indices to both the cleaved library and to a control library expressing a non-targeting gRNA. Following deep sequencing, the in vitro activity was confirmed by the fraction of the depleted sequences having the same PAM sequence relative to their occurrence in the control, indicating functional DNA cleavage by the OMNI nuclease (FIGS. 4A-4B and Table 3).

Activity in Human Cells on Endogenous Genomic Targets

OMNI-103 was assayed for its ability to promote editing on specific genomic locations in human cells. Editing activity on human genomic targets of OMNI-103 was assessed by NGS cleavage analysis on HeLa cells co-transfected with OMNI-103 nuclease and a panel of unique sgRNA molecules each designed to target a different genomic location. To this end, human optimized OMNI-103 nuclease was cloned into an in-frame-P2A-mCherry expression vector (pmOMNI, Table 4) and each of the OMNI-103 sgRNA molecule sequences were cloned into a shuttle-guide vector (pShuttle Guide, Table 4). The sgRNA molecules were designed to contain a 22-nucleotide guide sequence portion that targets a specific location in the human genome (Table 5) according to the corresponding OMNI-103 PAM preference, followed by the sgRNA scaffold sequence as discovered by TXTL (Table 3). At 72 hours post-transfection, cells were harvested. Half of the harvested cells were used for quantification of the OMNI-103 nuclease expression by FACS using mCherry fluorescence as a marker. The rest of the cells were lysed, and their genomic DNA content was extracted and used as a template for PCR amplification of the corresponding genomic targets. Amplicons were subjected to next generation sequencing (NGS) and the resulting reads were then used to calculate the percentage of editing events in their target sites. Short insertions or deletions (indels) around the cut site are the typical outcome of repair of DNA ends following nuclease-induced DNA cleavage. The calculation of % editing was deduced from the fraction of indel reads relative to the total aligned reads within each amplicon. As can be seen in Table 5 (column 5, "% editing"), OMNI-103 nuclease exhibited high and significant editing levels on most genomic sites.

Protein Purification of OMNI-103 Nuclease

The expression method for nuclease protein production and synthetic guide production for use in RNP assembly was described in U.S. Provisional Application No. 63/286,855. Briefly, OMNI-103 nuclease open reading frame was codon optimized for bacteria (Table 1) and cloned into modified pET9a plasmid with the following elements-SV40 NLS-OMNI-103 ORF bacterial optimized (from $2^{nd}$ amino acid)—HA tag—SV40 NLS-8 His-tag (Table 4). The OMNI-103 construct was expressed in KRX cells (PROMEGA). Cells were grown in TB+0.4% Glycerol with addition of 6.66 mM Rhamnose (26.4 ml from 0.5M stock), and 0.05% glucose (2 ml from 0.5M), and expressed in mid-log phase for 4 hr upon temperature reduction to 20° C. Cells were lysed using chemical lysis and cleared lysate was purified on Ni-NTA resin. The Ni-NTA elution fraction was purified on CEX (SO3 fractogel) resin followed by SEC purification on Superdex® 200 Increase 10/300 GL, AKTA Pure (GE Healthcare Life Sciences). Fractions containing OMNI-103 protein were pooled and concentrated to 30 mg/ml stocks and flash-frozen in liquid nitrogen and stored at −80° C.

OMNI-103 Cleavage Activity of RNP In Vitro

Synthetic sgRNAs of OMNI-103 were synthesized with three 2'-O-methyl 3'-phosphorothioate at the 3' and 5' ends (Agilent).

Figure 2A:
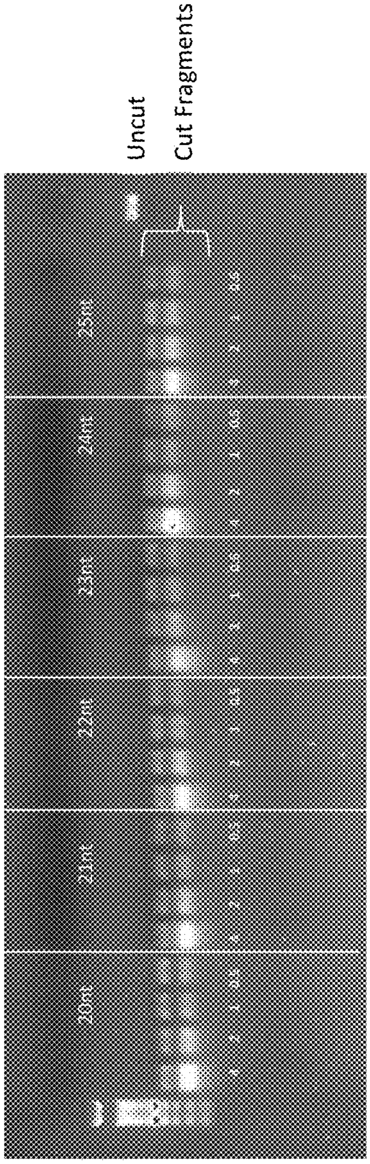
FIG. 2A-2C: OMNI-103 activity and spacer optimization as RNP in U2OS cells. OMNI-103 nuclease was overexpressed and purified. The purified protein was complexed with synthetic sgRNA to form RNPs.

Activity of OMNI-103 RNP was assayed in vitro with guide molecules having different spacer lengths (20-25 nucleotides) that target the same target site as guide PDCD1 S40 (Table 6, FIG. 2A). Briefly, 10 pmol of OMNI-103 nuclease were mixed with 20 pmol of synthetic guide. After a 10-minute incubation at room temperature, the RNP complexes were serial diluted to 4, 2, 1, 0.5 pmol and reacted with a 40 ng of linear DNA template prepared by amplification of the PDCD1 S40 target site from extracted genomic DNA. All spacer length (20-25 nucleotides) showed full cleavage of the PDCD1 template in all RNP concentrations indicating high cleavage activity (FIG. 2A).

Figure 2B:
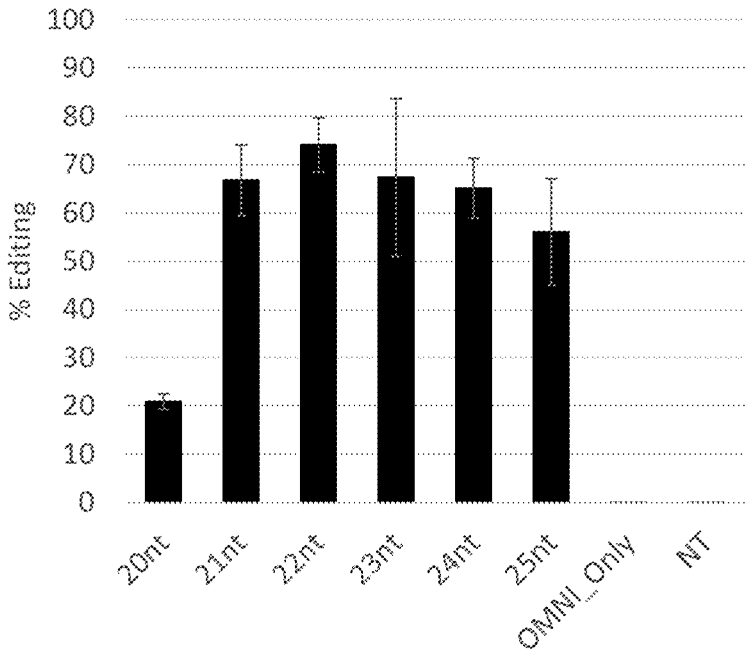

Guide Optimization for OMNI-103 Nuclease by Measuring Editing Activity of RNPs in U2OS Cells Spacer length optimization was also tested in a mammalian cell context. RNPs were assembled by mixing 100 uM OMNI-103 nuclease with 120 uM of synthetic guides of different spacer lengths (20-25 nucleotides, Table 6) and 100 uM Cas9 electroporation enhancer (IDT). After a 10-minute incubation at room temperature, the RNP complexes were mixed with 200,000 pre-washed U2OS cells and electroporated using Lonza SE Cell Line 4D-Nucleofector™ X Kit with DN100 according to the manufacture's protocol. 72 hours post-electroporation, cells were lysed, and their genomic DNA content was extracted. The corresponding genomic target sites were then amplified by PCR. Amplicons were subjected to NGS and the resulting sequences were used to calculate the percentage of editing events. As can be seen in FIG. 2B and Table 7, the spacer length of 22 nucleotides showed the highest editing level.

OMNI-103 RNP Editing Activity in Human Cells

Figure 2C:
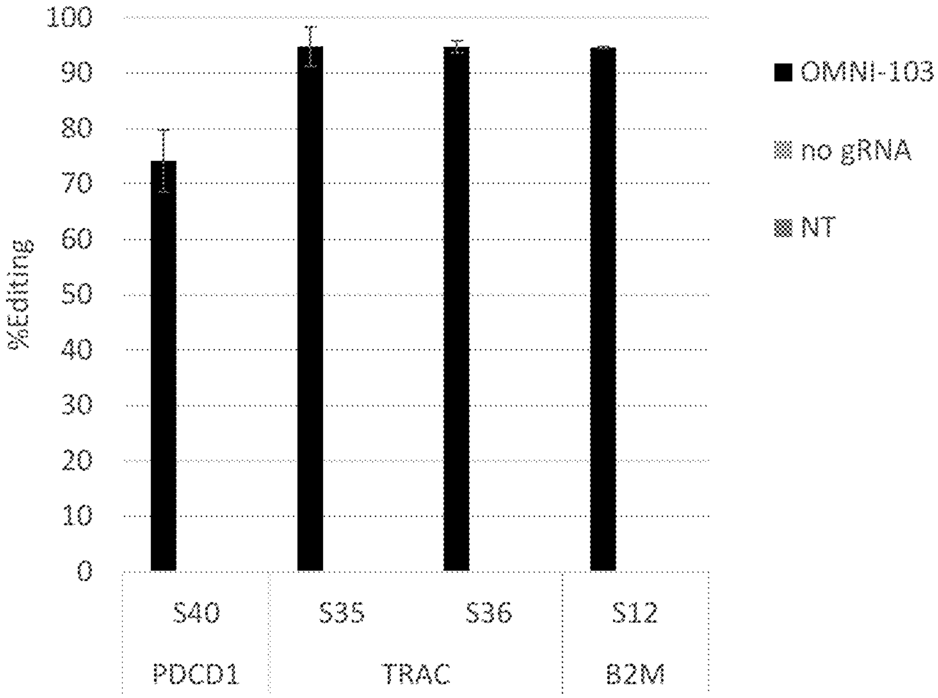

Activity of OMNI-103 protein as RNP in mammalian cells was observed in U2OS (Table 7, FIG. 2C) and comparable activity was also observed in T cells (Table 8). RNPs were assembled by mixing 100 uM nuclease with 120 uM of synthetic guide (Table 6) and 100 uM Cas9 electroporation enhancer (IDT). After a 10-minute incubation at room temperature, the RNP complexes were mixed with 200,000 U2OS cells and electroporated using Lonza SE Cell Line 4D-Nucleofector™ X Kit with DN100, according to the manufacture's protocol. 72 hours post-electroporation, cells were lysed, and their genomic DNA content was extracted. The corresponding genomic target sites were then amplified by PCR. Amplicons were subjected to NGS and the resulting sequences were used to calculate the percentage of editing events. OMNI-103 RNPs were tested with PDCD1 S40, TRAC S35, TRAC S36 and B2M S12 guides. All four (4) guides tested showed 70-90% editing levels (FIG. 2C).

Evaluating Off-Target Effects Using Guide-Seq Unbiased Analysis Method

Guide-seq allows for the unbiased in vitro detection of off-target genome editing events caused by CRISPR nucleases in living cells. Blunt-ended CRISPR RNA-guided nuclease (RGN) induced DSBs in the genomes of living human cells are tagged by integration of a blunt double-stranded oligodeoxynucleotide (dsODN) at these breaks via an end-joining process consistent with NHEJ. dsODN integration sites in genomic DNA are precisely mapped at the nucleotide level using unbiased amplification and deep NGS. After genomic DNA sonication and a series of adapter ligations, the oligonucleotide-containing libraries are subjected to high-throughput DNA sequencing and the output processed with the default Guide-seq software to identify the site of oligonucleotide capture.

To evaluate the specificity of OMNI-103 nuclease, Guide-seq was used to generate an unbiased survey of the off-target cleavage across the genome of human U2OS cells using the PDCD1 S40 and TRAC S35 sites (Table 6).

Figure 3A:
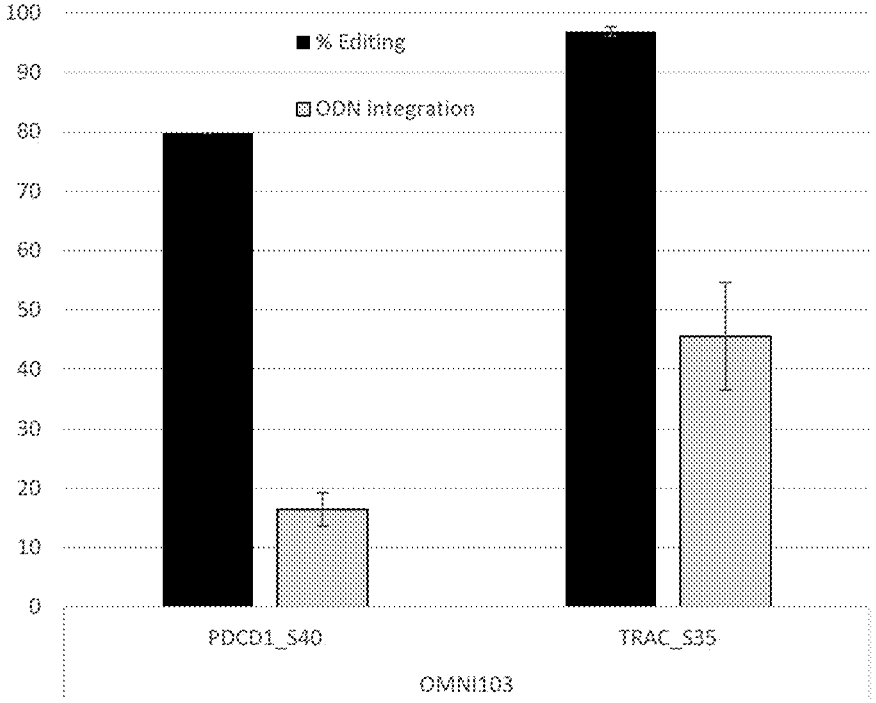
FIGS. 3A-3B. OMNI-103 off targets analysis by an unbiased biochemical assay (guide-seq). RNPs with PDCD1 S40 and TRAC S35 guide molecules (Table 6) were mixed with dsODN and electroporated into U2OS cell line.
Figure 3B:
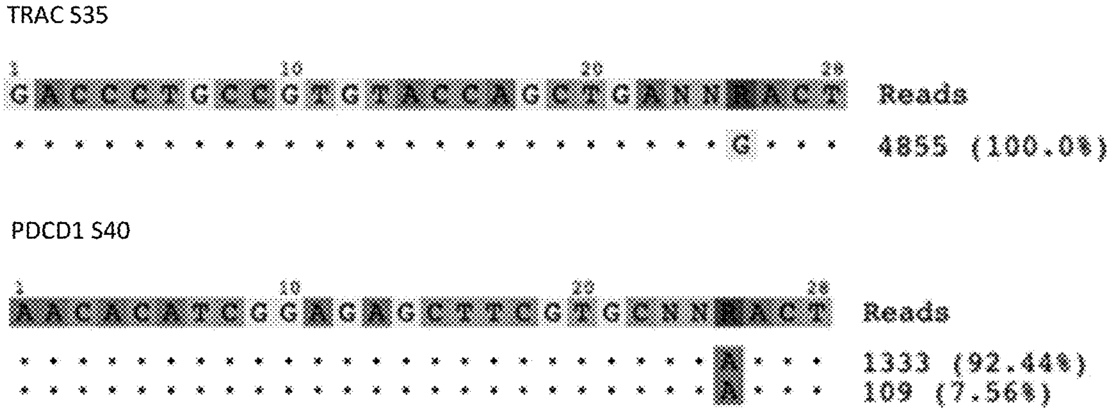

RNPs were assembled by mixing 100 uM nuclease with 120 uM of synthetic guide and 100 uM Cas9 electroporation enhancer (IDT). After a 10-minute incubation at room temperature, the RNP complexes were mixed with 100 uM dsODN and 200,000 pre-washed U2OS cells. The cells were electroporated using Lonza SE Cell Line 4D-Nucleofector™ X Kit with DN100 according to the manufacture's protocol. 72 hours post-electroporation, cells were lysed, and their genomic DNA content was extracted. The corresponding genomic target sites were then amplified by PCR. Amplicons were subjected to NGS and the resulting sequences were then used calculate the percentage of editing events and the dsODN integration (FIG. 3A). OMNI-103 did not show any off-target effects at the PDCD1 S40 and TRAC S35 sites (FIG. 3B).

TABLE 1

OMNI CRISPR nuclease sequences

| "OMNI" Name | SEQ ID NO of OMNI Amino Acid Sequence | SEQ ID NO of DNA sequence encoding OMNI | SEQ ID NO of DNA sequence codon optimized for expression in human cells | Nickase having inactivated RuvC domain | Nickase having inactivated HNH domain | Dead nuclease having inactivated RuvC and HNH domains |
|---|---|---|---|---|---|---|
| OMNI-103 | 1 | 2 | 3 | (D12, E776, H988, or D991) | (D856*, H857, or N880) | (D12, E776, H988, or D991) and (D856*, H857, or N880) |

Table 1. OMNI nuclease sequences: Table 1 lists the OMNI name, its corresponding nuclease protein sequence, its DNA sequence, its human optimized DNA sequence, alternative positions to be substituted to generate a nickase having an inactivated RuvC domain, alternative positions to be substituted to generate a nickase having an inactivated HNH domain, and alternative positions to be substituted to generate a catalytically dead nuclease having inactivated RuvC and HNH domains. Substitution to any other amino acid is permissible for each of the amino acid positions indicated in columns 5-7, except if followed by an asterisk, which indicates that any substitution other than aspartic acid (D) to glutamic acid (E) or glutamic acid (E) to aspartic acid (D) results in inactivation.

SUPPLEMENTAL TABLE 1

OMNI-103 Domains

| | OMNI-103 DOMAIN | | | | | | | | | |
|---|---|---|---|---|---|---|---|---|---|---|
| | A | B | C | D | E | F | G | H | I | J |
| Amino Acid Range | 1-45 | 46-83 | 84-158 | 159-302 | 303-515 | 516-727 | 728-778 | 779-923 | 924-1068 | 1069-1348 |

Supplemental Table 1. OMNI Domains: Supplemental Table 1 lists the amino acid range of each identified domain for OMNI CRISPR nuclease. For example, Domain G of OMNI-103 is identified by amino acids 728 to 778 of SEQ ID NO: 1. The listed amino acid ranges are based on a preferred analysis of a local alignment generated using the Smith-Waterman algorithm, however, the beginning or end of each domain range may increase or decrease by up to five amino acids.

TABLE 2

OMNI Guide RNA and Scaffold RNA Sequences

| | | OMNI-103 with sgRNA 12 |
|---|---|---|
| crRNA:tracrRNA duplex V1 | crRNA (Repeat) | GUUUGAGAGUAGUGUAA (SEQ ID NO: 4) |
| | Partial crRNA 1 | GUUUGAGAGUAGUGU (SEQ ID NO: 5) |
| | Partial crRNA 2 | GUUUGAGAGUAG (SEQ ID NO: 6) |
| | Partial crRNA 3 | GUUUGAGAGU (SEQ ID NO: 7) |
| | tracrRNA (Antirepeat) | UUACACUACAAGUUCAAAU (SEQ ID NO: 8) |
| | Partial tracrRNA 1 | ACACUACAAGUUCAAAU (SEQ ID NO: 9) |
| | Partial tracrRNA 2 | CUACAAGUUCAAAU (SEQ ID NO: 10) |
| | Partial tracrRNA 3 | ACAAGUUCAAAU (SEQ ID NO: 11) |
| tracrRNA sequences | tracrRNA Portion 1 | AAAAAUUUAUUCAAAUCCUUUUGCUACAUUG UGUAGAAUUU (SEQ ID NO: 12) |
| | tracrRNA Portion 2 | AAAGAUCUGGCAACAGAUCUUUUUUUU (SEQ ID NO: 13) |
| | tracrRNA Portion 2 -polyT | AAAGAUCUGGCAACAGAUC (SEQ ID NO: 14) |
| sgRNA Versions | sgRNA V1 | GUUUGAGAGUAGUGUAAgaaaUUACACUACAAG UUCAAAUAAAAAUUUAUUCAAAUCCUUUUGC UACAUUGUGUAGAAUUUAAAGAUCUGGCAAC AGAUCUUUUUUUU (SEQ ID NO: 15) |
| | sgRNA V2 | GUUUGAGAGUAGUGUAAgaaaUUACACUACAAG UUCAAAUAAAAAUUUAUUCAAAUCCAUUUGC UACAUUGUGUAGAAUUUAAAGAUCUGGCAAC AGAUCUUUUUUUU (SEQ ID NO: 16) |
| | sgRNA V2 Modified tracrRNA Portion 2 | AAAAAUUUAUUCAAAUCCAUUUGCUACAUUG UGUAGAAUUU (SEQ ID NO: 17) |
| | | OMNI-103 with sgRNA 32 |
| crRNA:tracrRNA duplex V1 | crRNA (Repeat) | GUUUGAGAGUAGUGUAA (SEQ ID NO: 18) |
| | Partial crRNA 1 | GUUUGAGAGUAGUGU (SEQ ID NO: 19) |
| | Partial crRNA 2 | GUUUGAGAGUAG (SEQ ID NO: 20) |
| | Partial crRNA 3 | GUUUGAGAGU (SEQ ID NO: 21) |
| | tracrRNA (Antirepeat) | UUACACUACAAGUUCAAAU (SEQ ID NO: 22) |
| | Partial tracrRNA 1 | ACACUACAAGUUCAAAU (SEQ ID NO: 23) |
| | Partial tracrRNA 2 | CUACAAGUUCAAAU (SEQ ID NO: 24) |
| | Partial tracrRNA 3 | ACAAGUUCAAAU (SEQ ID NO: 25) |
| tracrRNA sequences | tracrRNA Portion 1 | AAAAAUUUAUUCAAAUCCUUUUGCUACAUUG UGUAGAAUUU (SEQ ID NO: 26) |
| | tracrRNA Portion 2 | AAAGAUCUGGCAACAGAUCUUUUUUAUUUUU U (SEQ ID NO: 27) |
| | tracrRNA Portion 2 -polyT | AAAGAUCUGGCAACAGAUCUUUUUUA (SEQ ID NO: 28) |
| sgRNA Versions | sgRNA V1 | GUUUGAGAGUAGUGUAAgaaaUUACACUACAAG UUCAAAUAAAAAUUUAUUCAAAUCCUUUUGC UACAUUGUGUAGAAUUUAAAGAUCUGGCAAC AGAUCUUUUUUAUUUUUUU (SEQ ID NO: 29) |
| | sgRNA V2 | GUUUGAGAGUAGUGUAAgaaaUUACACUACAAG UUCAAAUAAAAAUUUAUUCAAAUCCUUUUGC UACAUUGUGUAGAAUUUAAAGAUCUGGCAAC AGAUCUUUUUUU (SEQ ID NO: 30) |
| | sgRNA V3 | GUUUGAGAGUAGUGUAAgaaaUUACACUACAAG UUCAAAUAAAAAUUUAUUCAAAUCCAUUUGC UACAUUGUGUAGAAUUUAAAGAUCUGGCAAC AGAUCUUUUUUU (SEQ ID NO: 31) |
| | sgRNA V3 Modified tracrRNA Portion 1 | AAAAAUUUAUUCAAAUCCAUUUGCUACAUUG UGUAGAAUUU (SEQ ID NO: 32) |

TABLE 3

| OMNI PAM Sequences showing activity for each tested sgRNA | | | | |
|---|---|---|---|---|
| | TXTL Depletion | | | |
| Name | PAM General | PAM Specific | Activity (1-Depletion score*), per respective sgRNA listed in right col. | sgRNA |
| OMNI-103 | NNRRHY or NNRVCT | NNRACT | 0.94, 0.97, 0.99, 0.98, 0.99 | sgRNA 12: V1, V2; sgRNA 32: V1, V2, V3 |

*Depletion score-Average of the ratios from two most depleted sites

TABLE 4

Plasmids and Constructs

| Plasmid | Purpose | Elements | Example |
|---|---|---|---|
| pET9a: OMNI-103 | Expressing OMNI polypeptide in the bacterial system | T7 promoter-SV40 NLS - OMNI ORF (Human optimized) - HA Tag-SV40 NLS - 8XHisTag - T7 terminator | SEQ ID NO: 37 |
| pShuttle Guide: OMNI-103 V2 | Expressing OMNI sgRNA in the bacterial and human cell system | U6 promoter - T7 promoter - T2 spacer - sgRNA scaffold - T7 terminator | SEQ ID NO: 38 |
| pbPOS T2 library | Bacterial/TXTL depletion assay | T2 protospacer - 8N PAM library - chloramphenicol acetyltransferase | SEQ ID NO: 39 |
| pmOMNI: OMNI-103 | Expressing OMNI polypeptide in the human cell system | CMV promoter - T7 promoter - SV40 NLS - OMNI ORF (Human optimized) - HA - SV40 NLS - P2A - mCherry - BGH poly(A) | SEQ ID NO: 40 |

TABLE 4

Appendix-Details of construct elements

| Element | Protein Sequence | DNA sequence |
|---|---|---|
| HA Tag | SEQ ID NO: 41 | SEQ ID NO: 45 |
| NLS | SEQ ID NO: 42 | SEQ ID NO: 46 |
| P2A | SEQ ID NO: 43 | SEQ ID NO: 47 |
| mCherry | SEQ ID NO: 44 | SEQ ID NO: 48 |

TABLE 5

OMNI-103 Nuclease activity in endogenous context in mammalian cells

| Gene Target | Corresponding Spacer Name | Spacer Sequence | PAM Sequence | % Indels |
|---|---|---|---|---|
| B2M | OMNI-103_B2M_s11-ref | SEQ ID NO: 49 | GAGACTCA | 83.0% |
| B2M | OMNI-103_B2M_s12-ref | SEQ ID NO: 50 | GTGACTTT | 90.6% |
| B2M | OMNI-103_B2M_S26-ref | SEQ ID NO: 51 | TCAACTTC | 90.5% |
| B2M | OMNI-103_B2M_S27-ref | SEQ ID NO: 52 | CAGACTTG | 58.2% |
| B2M | OMNI-103_B2M_S40-ref | SEQ ID NO: 53 | TTAACTAT | 85.7% |
| B2M | OMNI-103_B2M_S41-ref | SEQ ID NO: 54 | AAGACTTA | 56.2% |
| B2M | OMNI-103_B2M_S48-ref | SEQ ID NO: 55 | GAAGCTGA | 58.6% |
| B2M | OMNI-103_B2M_S49-ref | SEQ ID NO: 56 | TCAGCTTC | 62.7% |
| CXCR4 | OMNI-103_CXCR4_S35-ref | SEQ ID NO: 57 | CAGACTCA | 13.0% |
| CXCR4 | OMNI-103_CXCR4_s93-ref | SEQ ID NO: 58 | AAAGCTAG | 11.0% |
| ELANE | OMNI-103_ELANE_g114-ref | SEQ ID NO: 59 | TAGACTCC | 13.0% |
| ELANE | OMNI-103_ELANE_g115-alt | SEQ ID NO: 60 | GGGACTCC | 38.0% |
| ELANE | OMNI-103_ELANE_g128-ref | SEQ ID NO: 61 | CGGACTGC | 12.0% |
| PDCD1 | OMNI-103_PDCD1_S40-ref | SEQ ID NO: 62 | TAAACTGG | 53.0% |
| PDCD1 | OMNI-103_PDCD1_S92-ref | SEQ ID NO: 63 | AGGACTGC | 21.0% |
| SAMD9 | OMNI-103_SAMD9_g34-ref | SEQ ID NO: 64 | TCAACTCT | 54.4% |
| SAMD9 | OMNI-103_SAMD9_g36-ref | SEQ ID NO: 65 | TTGACTTA | 11.9% |
| SAMD9L | OMNI-103_SAMD9L_g133-alt | SEQ ID NO: 66 | CAAACTGA | 49.0% |
| SAMD9L | OMNI-103_SAMD9L_g79-alt | SEQ ID NO: 67 | TGAACTGA | 56.0% |
| SAMD9L | OMNI-103_SAMD9L_g80-alt | SEQ ID NO: 68 | AGAACTAC | 76.0% |
| SARM1 | OMNI-103_SARMI_g42-ref | SEQ ID NO: 69 | CCAACTCC | 33.2% |

TABLE 5-continued

OMNI-103 Nuclease activity in endogenous context in mammalian cells

| Gene Target | Corresponding Spacer Name | Spacer Sequence | PAM Sequence | % Indels |
|---|---|---|---|---|
| SARM1 | OMNI-103_SARM1_g43-ref | SEQ ID NO: 70 | GCAACTGC | 13.0% |
| SARM1 | OMNI-103_SARM1_g44-ref | SEQ ID NO: 71 | AAGACTGC | 27.0% |
| SARM1 | OMNI-103_SARM1_g45-ref | SEQ ID NO: 72 | GGAACTCA | 43.4% |
| TRAC | OMNI-103_TRAC S124-ref | SEQ ID NO: 73 | GGAACTTT | 69.8% |
| TRAC | OMNI-103_TRAC_S141-ref | SEQ ID NO: 74 | TAAACTTT | 86.9% |
| TRAC | OMNI-103_TRAC S142-ref | SEQ ID NO: 75 | GCCACTTT | 39.8% |
| TRAC | OMNI-103_TRAC_S24-ref | SEQ ID NO: 76 | TGGACTTC | 89.6% |
| TRAC | OMNI-103_TRAC_S35-ref | SEQ ID NO: 77 | GAGACTCT | 79.8% |
| TRAC | OMNI-103_TRAC_S36-ref | SEQ ID NO: 78 | CAGACTTG | 83.7% |
| TRAC | OMNI-103_TRAC_S58-ref | SEQ ID NO: 79 | CCAGCTGA | 50.8% |
| TRAC | OMNI-103_TRAC_s90-ref | SEQ ID NO: 80 | AAAACTGT | 59.1% |
| TRAC | OMNI-103_TRAC S91-ref | SEQ ID NO: 81 | CTGACTTT | 57.0% |

Table 5. Nuclease activity in endogenous context in mammalian cells: OMNI-103 nuclease was expressed in mammalian cell system (HeLa) by DNA transfection together with an sgRNA expressing plasmid. Cell lysates were used for site specific genomic DNA amplification and NGS. The percentage of indels was measured and analyzed to determine the editing level.

TABLE 6

Synthetic sgRNAs (spacer and scaffold) for OMNI-103

| Gene | Site | Spacer Length | Spacer Sequence | PAM | Scaffold | Full sgRNA |
|---|---|---|---|---|---|---|
| B2M | S12 | 22nt | SEQ ID NO: 82 | GTGACTTT | SEQ ID NO: 91 | SEQ ID NO: 100 |
| TRAC | S36 | 22nt | SEQ ID NO: 83 | CAGACTTG | SEQ ID NO: 92 | SEQ ID NO: 101 |
| | S35 | 22nt | SEQ ID NO: 84 | GAGACTCT | SEQ ID NO: 93 | SEQ ID NO: 102 |
| PDCD1 | S40 | 25nt | SEQ ID NO: 85 | TAAACTGG | SEQ ID NO: 94 | SEQ ID NO: 103 |
| | S40 | 24nt | SEQ ID NO: 86 | TAAACTGG | SEQ ID NO: 95 | SEQ ID NO: 104 |
| | S40 | 23nt | SEQ ID NO: 87 | TAAACTGG | SEQ ID NO: 96 | SEQ ID NO: 105 |
| | S40 | 22nt | SEQ ID NO: 88 | TAAACTGG | SEQ ID NO: 97 | SEQ ID NO: 106 |
| | S40 | 21nt | SEQ ID NO: 89 | TAAACTGG | SEQ ID NO: 98 | SEQ ID NO: 107 |
| | S40 | 20nt | SEQ ID NO: 90 | TAAACTGG | SEQ ID NO: 99 | SEQ ID NO: 108 |

TABLE 7

OMNI-103 activity and spacer optimization as RNPs in U2OS cells

| Gene | Site | Spacer Sequence | PAM | Spacer Length | % Indels | STD |
|---|---|---|---|---|---|---|
| PDCD1 | S40 | SEQ ID NO: 90 | TAAACTGG | 20nt | 20.935 | 1.60513239 |
| | S40 | SEQ ID NO: 89 | TAAACTGG | 21nt | 66.77 | 7.29734198 |
| | S40 | SEQ ID NO: 88 | TAAACTGG | 22nt | 74.145 | 5.59321464 |
| | S40 | SEQ ID NO: 87 | TAAACTGG | 23nt | 67.38 | 16.3341666 |
| | S40 | SEQ ID NO: 86 | TAAACTGG | 24nt | 65.105 | 6.20132647 |
| | S40 | SEQ ID NO: 85 | TAAACTGG | 25nt | 56.055 | 11.0379369 |
| TRAC | S35 | SEQ ID NO: 84 | GAGACTCT | 22nt | 94.76 | 3.54967604 |
| | S36 | SEQ ID NO: 83 | CAGACTTG | 22nt | 94.755 | 1.08187338 |
| B2M | S12 | SEQ ID NO: 82 | GTGACTTT | 22nt | 94.635 | 0.16263456 |

Table 7. OMNI-103 RNPs were assembled with synthetic sgRNA (Agilent) and electroporated into U2OS cells. Gene name, spacer sequences, and spacer length are indicated next to the editing level (% indels) measured by NGS.

TABLE 8

| FACS Results of OMNI-103 editing as RNP in primary T cells | | | | | | |
|---|---|---|---|---|---|---|
| Gene | Genomic site | Spacer sequence | PAM | Spacer Length | % Negative | STD |
| TRAC | S35 | SEQ ID NO: 84 | GAGACTCT | 22nt | 80% | 7.786643 |
| TRAC | S36 | SEQ ID NO: 83 | CAGACTTG | 22nt | 54% | 5.433231 |
| B2M | S12 | SEQ ID NO: 82 | GTGACTTT | 22nt | 80% | 9.563636 |

Table 8. Protein expression levels of TCR and B2M in primary T cells, 3 days after electroporation of OMNI-103 with specific synthetic sgRNA molecules (Agilent) targeting either TRAC or B2M.

Example 2: Alternate OMNI-103 CRISPR Nuclease-RNA Complexes

Methods

OMNI-103 Protein Expression

Briefly, and similar to the protein expression method described above, the nuclease open reading frame was codon optimized for human cells and cloned into modified pET9a plasmid with the following elements—SV40 NLS-OMNI-103 ORF (from 2$^{nd}$ amino acid human optimized)—HA tag—SV40 NLS—8 His-tag. This sequence can be found in Table 4. The OMNI-103 construct was expressed in KRX cells (Promega). Cells were grown in TB+0.4% Glycerol with the addition of 6.66 mM rhamnose (26.4 ml from 0.5M stock) and 0.05% glucose (2 ml from 0.5M). Protein was expressed in mid-log phase for 4 hr upon temperature reduction to 20° C. Cells were lysed using chemical lysis and cleared lysate was purified on Ni-NTA resin. Ni-NTA elution fraction was purified on CEX (SO3 fractogel) resin followed by SEC purification on Superdex 200 Increase 10/300 GL, AKTA Pure (GE Healthcare Life Sciences). Fractions containing OMNI-103 protein were pooled and concentrated to 30 mg/ml stocks and flash-frozen in liquid nitrogen and stored at −80° C.

Synthetic sgRNA Used

All synthetic sgRNAs of OMNI-103 were synthesized with three 2'-O-methyl 3'-phosphorothioate at the 3' and 5' ends (Agilent or Synthego).

Activity in Mammalian Cell Lines

The ability of OMNI-103 to promote editing with shorter sgRNA versions was tested on specific genomic locations in human cells (Table 10). For HeLa cells, the OMNI-103-P2A-mCherry expression vector (pmOMNI, Table 4) was transfected together with the sgRNA (pShuttle guide—Table 4, spacer sequence—Table 10).

For U2OS cells, RNPs were assembled by mixing 100 uM nuclease with 120 uM of synthetic guide and 100 uM Cas9 electroporation enhancer (IDT). After 10 minutes of incubation at room-temperature, the RNP complexes were mixed with 200,000 pre-washed U2OS cells and electroporated using Lonza SE Cell Line 4D-Nucleofector™ X Kit with the DN100 program, according to the manufacture's protocol. At 72 h cells were lysed, and their genomic DNA content was used in a PCR reaction that amplified the corresponding putative genomic targets. Amplicons were subjected to NGS and the resulting sequences were then used to calculate the percentage of editing events.

For T cells, RNPs were assembled by mixing 113 uM nuclease and 160 uM of synthetic guide and incubating for 10 minutes at room temperature, RNP complexes were mixed with 200,000 primary activated T cells, and electroporated using P3 Primary Cell 4D-Nucleofector™ X Kit, with EH-115 pulse code. After three (3) days and eight (8) days cells were collected, and CD3 and the edited protein expression was measured by flow cytometry.

Results

Activity of Short Guides Across Genomic Sites and Cell Types

Figure 7:
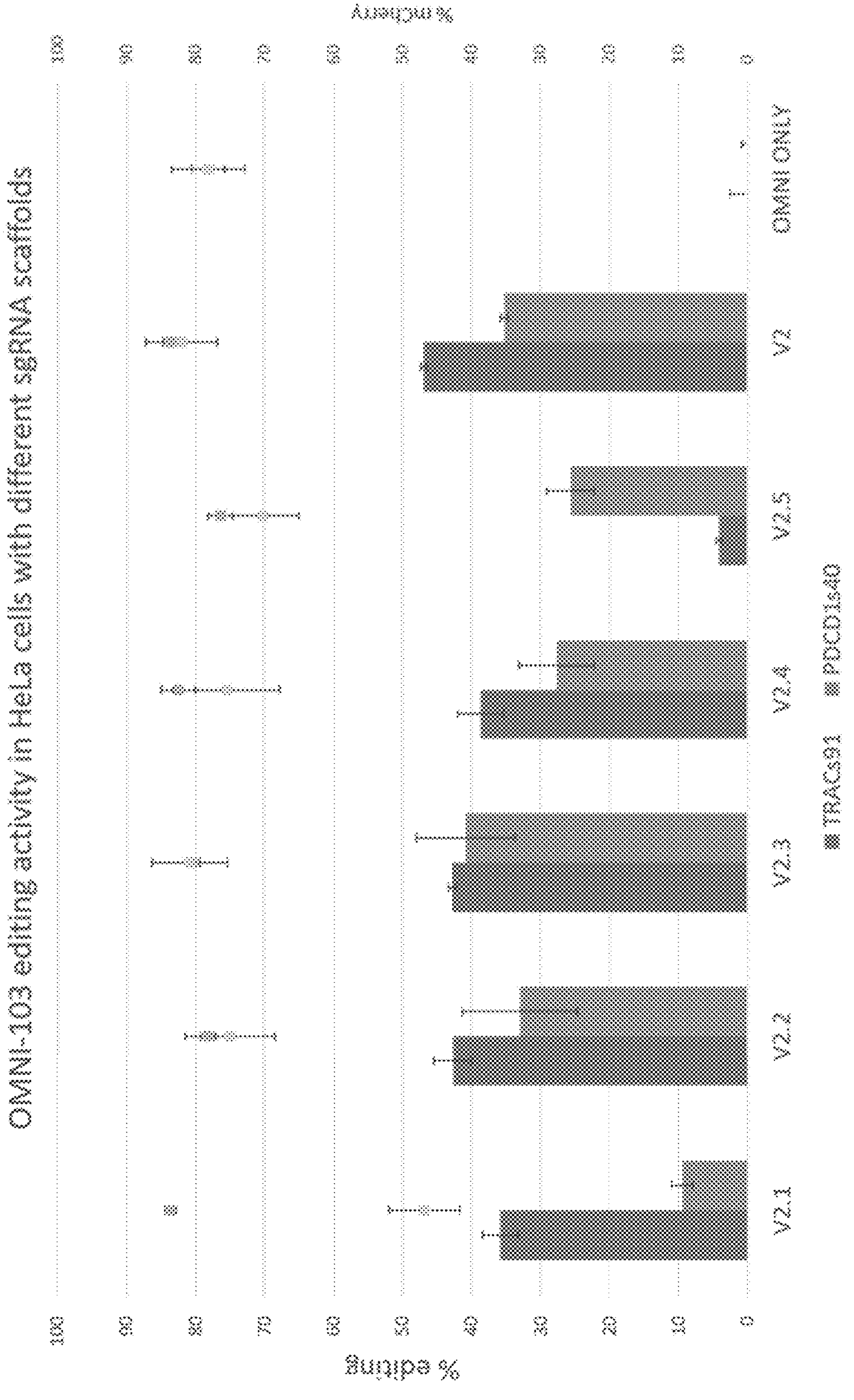
FIG. 7. OMNI-103 editing activity in Hela cells with different sgRNA scaffolds (Table 3). Hela cells were transfected with OMNI-103 and sgRNA plasmids targeting TRAC-S91 or PDCD-S40. Editing activity was calculated based on next generation sequencing results (bars), and transfection efficiency was based on FACS analysis of the mCherry expression. Presented are the average and standard deviation of three technical replicates.
Figure 8:
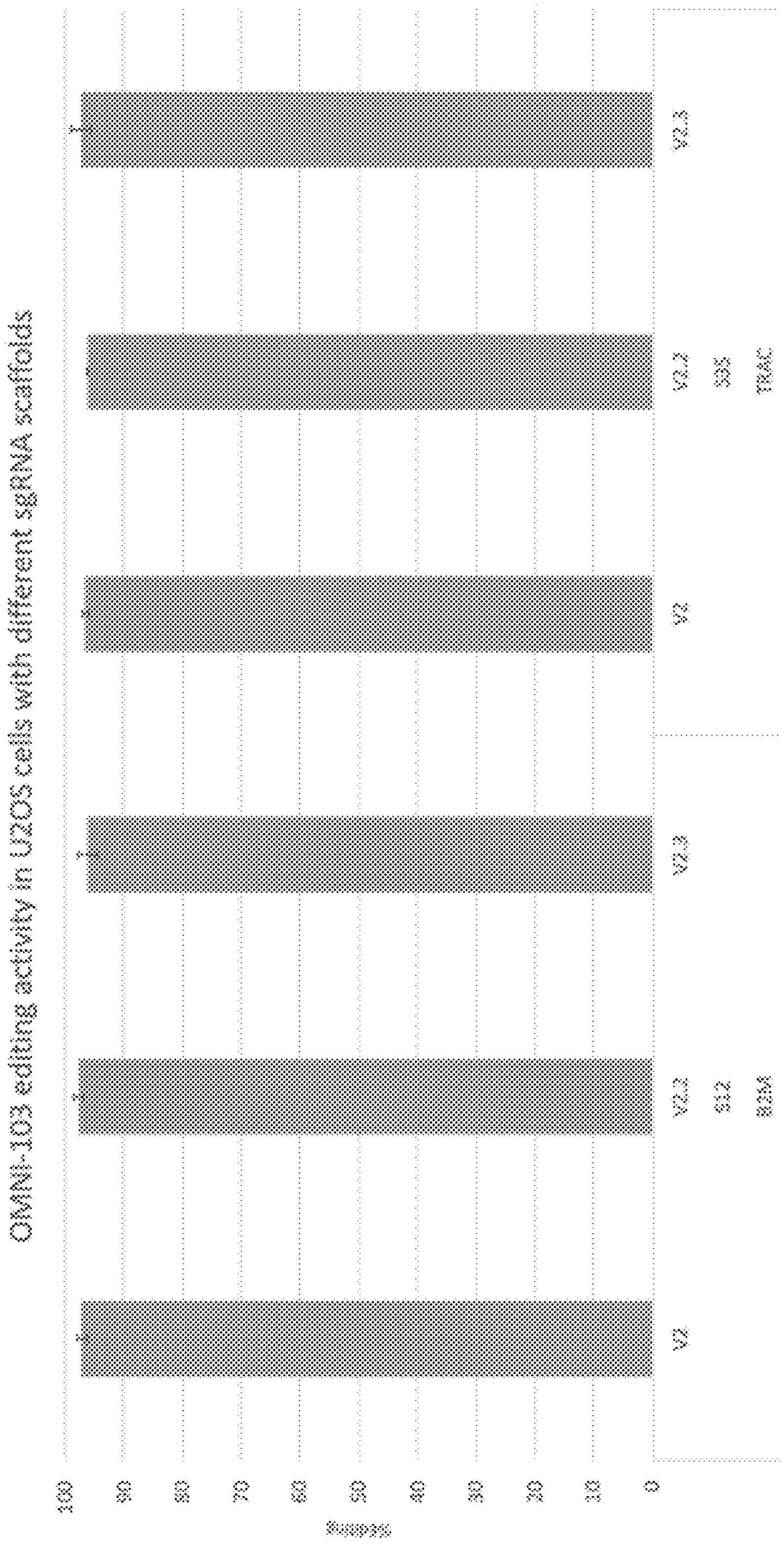
FIG. 8. Activity in U2OS. U2OS cells were electroporated with OMNI-103 and sgRNA (RNP) targeting TRAC S35 and B2M S12. Editing activity was calculated based on next generation sequencing (NGS) results. Presented are the average and standard deviation of three technical replicates.
Figure 9:
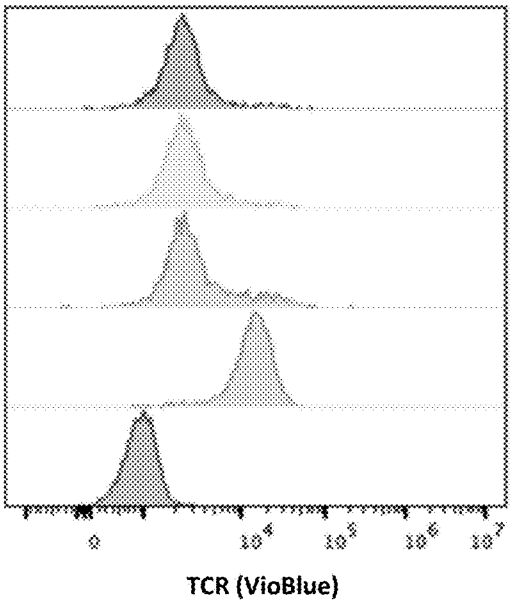
FIG. 9. Activity in primary T cells. Primary T cells were isolated from PBMCs and activated according to manufacturer's protocol (Miltenyi #130-096-535, #130-091-441). Activated T cells were electroporated with OMNI-103 and sgRNAs (RNPs) targeting TRAC-s35 and B2M-s12. After eight (8) days, cells were measured by flow cytometry for TCR and B2M expression level. For the analysis, only live and CD3-positive cells were counted. The results presented are representative and are one of three T cell donors which all showed similar results.
Figure 9:
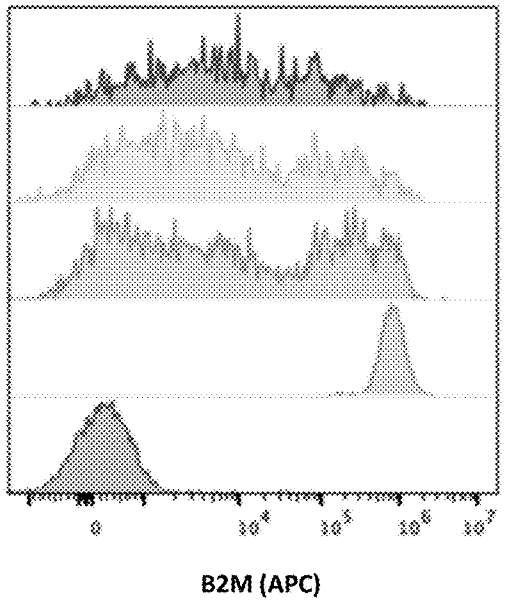
Figure 10:
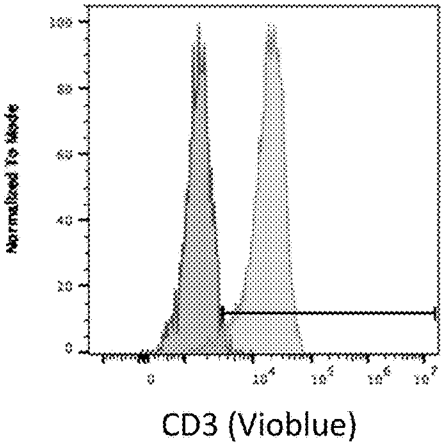
FIG. 10. T cell activation assay. Donor sample cells used in cleavage activity assay were activated with beads for 72 h and displayed an 85% primary T cell activation rate as measured by FACS ($CD3^+$ $CD25^+$ cells).
Figure 10:
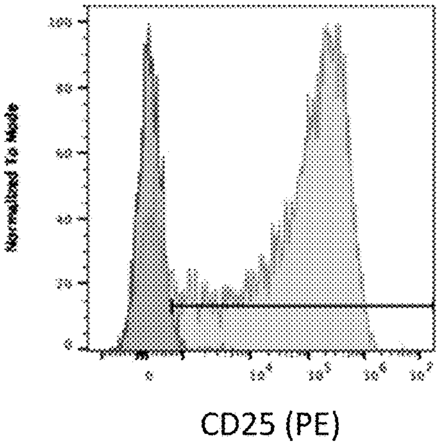
Figure 11:
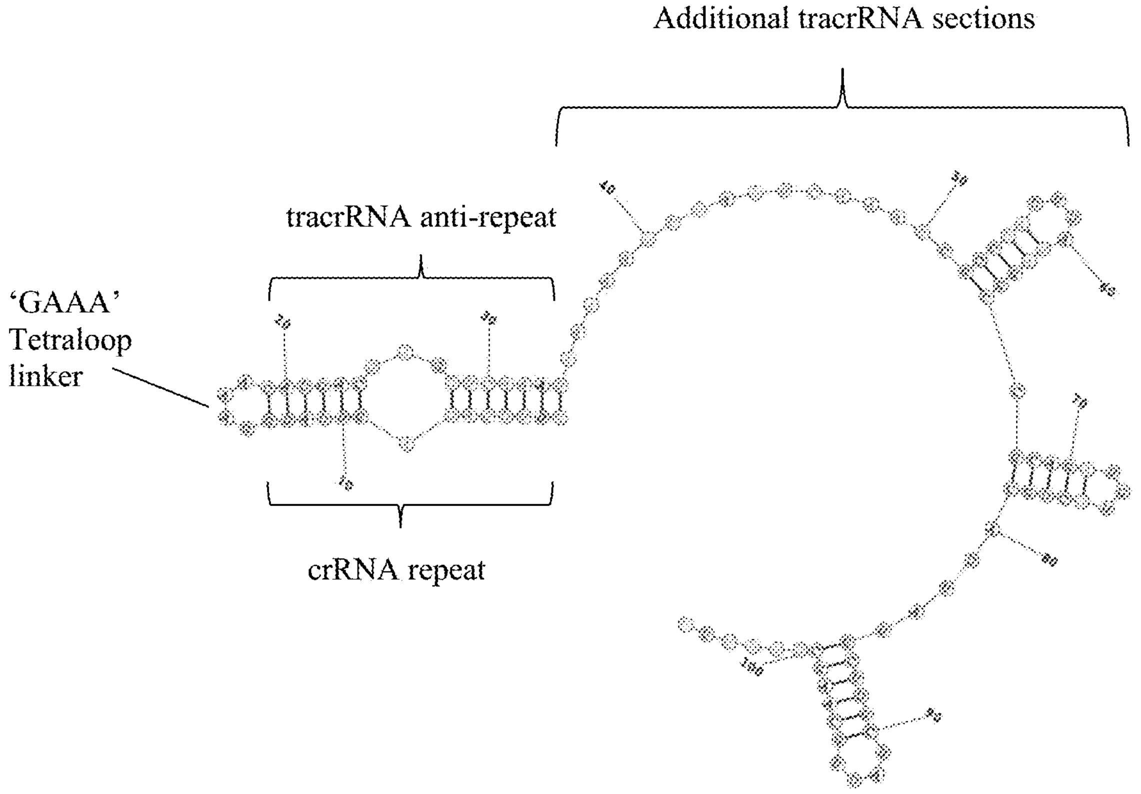
FIG. 11. Representative example of an RNA scaffold. An example RNA scaffold portion comprises a crRNA portion linked by a tetraloop to a tracrRNA portion. The crRNA portion comprises a crRNA repeat sequence. The tracrRNA portion comprises a tracrRNA anti-repeat sequence and additional tracrRNA sections. The RNA molecule may further comprise a guide sequence portion (i.e. an RNA spacer) linked to the crRNA repeat sequence, such that the RNA molecule functions as a single-guide RNA molecule.

OMNI-103 nuclease activity was optimized for use with shorter sgRNA scaffolds. Five (5) short sgRNA scaffolds were designed based on the 'V2' duplex version, which contained up to four deletions around the tetra loop "GAAA" and the terminator region (Table 9, FIGS. 6A-6F). To test the level of activity OMNI-103 displayed with the designed V2 scaffolds, sgRNAs having guide sequence portions of "TRAC-s91" or "PDCD-s40" were transfected into HeLa cells. Editing activity was calculated based on NGS results (FIG. 7). In all cases the designed sgRNA enabled editing activity. The next step was to test OMNI-103 activity as an RNP in U2OS and primary T cells. OMNI-103 was electroporated with sgRNAs having a V2, V2.2 or V2.3 scaffold and having guide sequence portions of "TRAC-s35" or "B2M-s12". Editing activity was calculated based on NGS results, and as demonstrated the level of OMNI-103 activity was not impaired when used with any of the scaffold variants (FIG. 8). In primary T cells, when the short scaffold variants were utilized, improved activity was demonstrated.

TABLE 9

| OMNI-103 Designed Scaffold Sequences | | |
|---|---|---|
| Experimental Name | Full sequence | Length |
| V2.1 | GUUUGAGAGUAGUGGAAACACUACAAGUUCAAAUAAAAAUUUAUU CAAAUCCAUUUGCUACAUUGUGUAGAAUUUAAAGAUCUGGCAACA GAUCUUUUUUU (SEQ ID NO: 123) | 101 |

TABLE 9-continued

| OMNI-103 Designed Scaffold Sequences | | |
|---|---|---|
| V2.2 | GUUUGAGAGUAGUGUAAGAAAUUACACUACAAGUUCAAAUAAAAA UUUAUUCAAAUCCAUUUGCUACAUUGUGUAGAAUUUUUUU (SEQ ID NO: 124) | 85 |
| V2.3 | GUUUGAGAGUAGUGGAAACACUACAAGUUCAAAUAAAAAUUUAUU CAAAUCCAUUUGCUACAUUGUGUAGAAUUUUUUU (SEQ ID NO: 125) | 79 |
| V2.4 | GUUUGAGAGUAGUGGAAACACUACAAGUUCAAAUAAAAAUUUAUU CAAAUCCAUUUGCUACAUUGUGUAGAAUUUAAAGAUGCAAAUCUU UUUUU (SEQ ID NO: 126) | 95 |
| V2.5 | GUUUGAGAGUAGUGUAAGAAAUUACACUACAAGUUCAAAUAAAAA UUUAUUCAAAUCCAUUUGCUACAUUGUGUAGAAUUUAAAGAUGCA AAUCUUUUUUU (SEQ ID NO: 127) | 101 |

| Experimental Name | crRNA Repeat | tracrRNA anti-repeat |
|---|---|---|
| V2.1 | GUUUGAGAGUAGUG (SEQ ID NO: 114) | CACUACAAGUUCAAAU (SEQ ID NO: 116) |
| V2.2 | GUUUGAGAGUAGUGUAA (SEQ ID NO: 115) | UUACACUACAAGUUCAAAU (SEQ ID NO: 117) |
| V2.3 | GUUUGAGAGUAGUG (SEQ ID NO: 114) | CACUACAAGUUCAAAU (SEQ ID NO: 116) |
| V2.4 | GUUUGAGAGUAGUG (SEQ ID NO: 114) | CACUACAAGUUCAAAU (SEQ ID NO: 116) |
| V2.5 | GUUUGAGAGUAGUGUAA (SEQ ID NO: 115) | UUACACUACAAGUUCAAAU (SEQ ID NO: 117) |

| Experimental Name | tracrRNA Portion 1 | tracrRNA Portion 1 - partial | tracrRNA Portion 2 | tracrRNA Portion 2 - partial |
|---|---|---|---|---|
| V2.1 | AAAAAUUUAUUCA AAUCCAUUUGCUA CAUUGUGUAGAAU UU (SEQ ID NO: 118) | Not listed | AAAGAUCUGG CAACAGAUCU UUUUUU (SEQ ID NO: 121) | AAAGAUCUGG CAACAGA (SEQ ID NO: 123) |
| V2.2 | AAAAAUUUAUUCA AAUCCAUUUGCUA CAUUGUGUAGAAU UUUUUU (SEQ ID NO: 119) | AAAAAUUUAU UCAAAUCCAU UUGCUACAUU GUGUAGAA (SEQ ID NO: 120) | Not listed | Not listed |
| V2.3 | AAAAAUUUAUUCA AAUCCAUUUGCUA CAUUGUGUAGAAU UUUUUU (SEQ ID NO: 119) | AAAAAUUUAU UCAAAUCCAU UUGCUACAUU GUGUAGAA (SEQ ID NO: 120) | Not listed | Not listed |
| V2.4 | AAAAAUUUAUUCA AAUCCAUUUGCUA CAUUGUGUAGAAU UU (SEQ ID NO: 118) | Not listed | AAAGAUGCAA AUCUUUUUUU (SEQ ID NO: 122) | AAAGAUGCAA AUC (SEQ ID NO: 124) |
| V2.5 | AAAAAUUUAUUCA AAUCCAUUUGCUA CAUUGUGUAGAAU UU (SEQ ID NO: 118) | Not listed | AAAGAUGCAA AUCUUUUUUU (SEQ ID NO: 122) | AAAGAUGCAA AUC (SEQ ID NO: 124) |

TABLE 10

| Endogenic targets for testing activity short-scaffold guide activity | | |
|---|---|---|
| Gene | Site | Spacer |
| TRAC | s91 | GCUGUGGCCUGGAGCAACAAAU (SEQ ID NO: 125) |
| PDCD1 | s40 | AACACAUCGGAGAGCUUCGUGC (SEQ ID NO: 126) |
| B2M | S12 | GUAUGCCUGCCGUGUGAACCAU (SEQ ID NO: 127) |
| TRAC | S35 | GACCCUGCCGUGUACCAGCUGA (SEQ ID NO: 128) |

TABLE 11

Summary of the activity panel of short guides across different endogenic targets in three cell types

| Cell Type | Gene | Site | V2 | V2.1 | V2.2 | V2.3 | V2.4 | V2.5 |
|---|---|---|---|---|---|---|---|---|
| HeLa | TRAC | s91 | 46.90 | 35.81 | 42.68 | 42.74 | 38.62 | 4.06 |
| HeLa | PDCD1 | s40 | 35.21 | 9.45 | 32.94 | 40.82 | 27.60 | 25.59 |
| U2OS | TRAC | S35 | 96.58 | N/A | 96.22 | 97.34 | N/A | N/A |
| U2OS | B2M | S12 | 97.19 | N/A | 97.76 | 96.16 | N/A | N/A |
| Primary T cells | TRAC | S35 | 77.40 | N/A | 87.60 | 90.80 | N/A | N/A |
| Primary T cells | B2M | S12 | 79.90 | N/A | 88.00 | 91.60 | N/A | N/A |

TABLE 12

Summary of the sgRNAs used in the U2OS and primary T cell assays

| sgRNA Name | Gene | Site | Spacer | Scaffold | sgRNA |
|---|---|---|---|---|---|
| OMNI-103 v2.2 TRAC S35 | TRAC | S35 | SEQ ID NO: 128 | SEQ ID NO: 110 | SEQ ID NO: 129 |
| OMNI-103 v2.3 TRAC S35 | TRAC | S35 | SEQ ID NO: 128 | SEQ ID NO: 111 | SEQ ID NO: 130 |
| OMNI-103 v2.2 B2M S12 | B2M | S12 | SEQ ID NO: 127 | SEQ ID NO: 110 | SEQ ID NO: 131 |
| OMNI-103 v2.3 B2M S12 | B2M | S12 | SEQ ID NO: 127 | SEQ ID NO: 111 | SEQ ID NO: 132 |

REFERENCES

1. Ahmad and Allen (1992) "Antibody-mediated Specific Binging and Cytotoxicity of Lipsome-entrapped Doxorubicin to Lung Cancer Cells *in Vitro*", Cancer Research 52:4817-20.
2. Anderson (1992) "Human gene therapy", Science 256: 808-13.
3. Basha et al. (2011) "Influence of Cationic Lipid Composition on Gene Silencing Properties of Lipid Nanoparticle Formulations of siRNA in Antigen-Presenting Cells", Mol. Ther. 19(12):2186-200.
4. Behr (1994) "Gene transfer with synthetic cationic amphiphiles: Prospects for gene therapy", Bioconjuage Chem 5:382-89.
5. Blaese et al. (1995) "Vectors in cancer therapy: how will they deliver", Cancer Gene Ther. 2:291-97.
6. Blaese et al. (1995) "T lympocyte-directed gene therapy for ADA-SCID: initial trial results after 4 years", Science 270(5235):475-80.
7. Briner et al. (2014) "Guide RNA functional modules direct Cas9 activity and orthognality", Molecular Cell 56:333-39.
8. Buchschacher and Panganiban (1992) "Human immunodeficiency virus vectors for inducible expression of foreign genes", J. Virol. 66:2731-39.
9. Burstein et al. (2017) "New CRISPR-Cas systems from uncultivated microbes", Nature 542:237-41.
10. Canver et al., (2015) "BCL11A enhancer dissection by Cas9-mediated in situ saturating mutagenesis", Nature Vol. 527, Pgs. 192-214.
11. Chang and Wilson (1987) "Modification of DNA ends can decrease end-joining relative to homologous recombination in mammalian cells", Proc. Natl. Acad. Sci. USA 84:4959-4963.
12. Charlesworth et al. (2019) "Identification of preexisting adaptive immunity to Cas9 proteins in humans", Nature Medicine, 25(2), 249.
13. Chung et al. (2006) "*Agrobacterium* is not alone: gene transfer to plants by viruses and other bacteria", Trends Plant Sci. 11(1):1-4.
14. Coelho et al. (2013) "Safety and efficacy of RNAi therapy for transthyretin amyloidosis" N. Engl. J. Med. 369, 819-829.
15. Crystal (1995) "Transfer of genes to humans: early lessons and obstacles to success", Science 270(5235): 404-10.
16. Dillon (1993) "Regulation gene expression in gene therapy" Trends in Biotechnology 11(5):167-173.
17. Dranoff et al. (1997) "A phase I study of vaccination with autologous, irradiated melanoma cells engineered to secrete human granulocyte macrophage colony stimulating factor", Hum. Gene Ther. 8(1):111-23.
18. Dunbar et al. (1995) "Retrovirally marked CD34-enriched peripheral blood and bone marrow cells contribute to long-term engraftment after autologous transplantation", Blood 85:3048-57.
19. Ellem et al. (1997) "A case report: immune responses and clinical course of the first human use of ganulocyte/macrophage-colony-stimulating-factor-tranduced autologous melanoma cells for immunotherapy", Cancer Immunol Immunother 44:10-20.
20. Gao and Huang (1995) "Cationic liposome-mediated gene transfer" Gene Ther. 2(10):710-22.
21. Haddada et al. (1995) "Gene Therapy Using Adenovirus Vectors", in: The Molecular Repertoire of Adenoviruses III: Biology and Pathogenesis, ed. Doerfler and Böhm, pp. 297-306.

22. Han et al. (1995) "Ligand-directed retro-viral targeting of human breast cancer cells", Proc. Natl. Acad. Sci. USA 92(21):9747-51.

23. Humbert et al., (2019) "Therapeutically relevant engraftment of a CRISPR-Cas9—edited HSC-enriched population with HbF reactivation in nonhuman primates", Sci. Trans. Med., Vol. 11, Pgs. 1-13.

24. Inaba et al. (1992) "Generation of large numbers of dendritic cells from mouse bone marrow cultures supplemented with granulocyte/macrophage colony-stimulating factor", J Exp Med. 176(6):1693-702.

25. Jiang and Doudna (2017) "CRISPR-Cas9 Structures and Mechanisms", Annual Review of Biophysics 46:505-29.

26. Jinek et al. (2012) "A programmable dual-RNA-guided DNA endonuclease in adaptive bacterial immunity", Science 337(6096):816-21.

27. Johan et al. (1992) "GLVR1, a receptor for gibbon ape leukemia virus, is homologous to a phosphate permease of *Neurospora crassa* and is expressed at high levels in the brain and thymus", J Virol 66(3):1635-40.

28. Judge et al. (2006) "Design of noninflammatory synthetic siRNA mediating potent gene silencing in vivo", Mol Ther. 13(3):494-505.

29. Kohn et al. (1995) "Engraftment of gene-modified umbilical cord blood cells in neonates with adnosine deaminase deficiency", Nature Medicine 1:1017-23.

30. Kremer and Perricaudet (1995) "Adenovirus and adeno-associated virus mediated gene transfer", Br. Med. Bull. 51(1):31-44.

31. Macdiarmid et al. (2009) "Sequential treatment of drug-resistant tumors with targeted minicells containing siRNA or a cytotoxic drug", Nat Biotehcnol. 27(7):643-51.

32. Malech et al. (1997) "Prolonged production of NADPH oxidase-corrected granulocyes after gene therapy of chronic granulomatous disease", PNAS 94(22):12133-38.

33. Maxwell et al. (2018) "A detailed cell-free transcription-translation-based assay to decipher CRISPR protospacer adjacent motifs", Methods 14348-57

34. Miller et al. (1991) "Construction and properties of retrovirus packaging cells based on gibbon ape leukemia virus", J Virol. 65(5):2220-24.

35. Miller (1992) "Human gene therapy comes of age", Nature 357:455-60.

36. Mir et al. (2019) "Type II-C CRISPR-Cas9 Biology, Mechanism and Application", ACS Chem. Biol. 13(2): 357-365.

37. Mitani and Caskey (1993) "Delivering therapeutic genes—matching approach and application", Trends in Biotechnology 11(5):162-66.

38. Nabel and Felgner (1993) "Direct gene transfer for immunotherapy and immunization", Trends in Biotechnology 11(5):211-15.

39. Nehls et al. (1996) "Two genetically separable steps in the differentiation of thymic epithelium" Science 272: 886-889.

40. Nishimasu et al. "Crystal structure of Cas9 in complex with guide RNA and target DNA" (2014) Cell 156(5): 935-49.

41. Nishimasu et al. (2015) "Crystal Structure of *Staphylococcus aureus* Cas9" Cell 162(5):1113-26.

42. Palermo et al. (2018) "Key role of the REC lobe during CRISPR-Cas9 activation by 'sensing', 'regulating', and 'locking' the catalytic HNH domain" Quarterly Reviews of Biophysics 51, e9, 1-11.

43. Remy et al. (1994) "Gene Transfer with a Series of Lipphilic DNA-Binding Molecules", Bioconjugate Chem. 5(6):647-54.

44. Sentmanat et al. (2018) "A Survey of Validation Strategies for CRISPR-Cas9 Editing", Scientific Reports 8:888, doi: 10.1038/s41598-018-19441-8.

45. Sommerfelt et al. (1990) "Localization of the receptor gene for type D simian retroviruses on human chromosome 19", J. Virol. 64(12):6214-20.

46. Van Brunt (1988) "Molecular framing: transgenic animals as bioactors" Biotechnology 6:1149-54.

47. Vigne et al. (1995) "Third-generation adenovectors for gene therapy", Restorative Neurology and Neuroscience 8(1,2): 35-36.

48. Wagner et al. (2019) "High prevalence of *Streptococcus pyogenes* Cas9-reactive T cells within the adult human population" Nature Medicine, 25(2), 242

49. Wilson et al. (1989) "Formation of infectious hybrid virion with gibbon ape leukemia virus and human T-cell leukemia virus retroviral envelope glycoproteins and the gag and pol proteins of Moloney murine leukemia virus", J. Virol. 63:2374-78.

50. Yu et al. (1994) "Progress towards gene therapy for HIV infection", Gene Ther. 1(1):13-26.

51. Zetsche et al. (2015) "Cpf1 is a single RNA-guided endonuclease of a class 2 CRISPR-Cas system" Cell 163(3):759-71.

52. Zuris et al. (2015) "Cationic lipid-mediated delivery of proteins enables efficient protein based genome editing in vitro and in vivo" Nat Biotechnol. 33(1):73-80.

What is claimed is:

1. A non-naturally occurring composition comprising a CRISPR nuclease comprising a sequence having at least 90% identity to the amino acid sequence of SEQ ID NO: 1, or a nucleic acid molecule comprising a sequence encoding the CRISPR nuclease, further comprising one or more RNA molecules, or a DNA polynucleotide encoding any one of the one or more RNA molecules, wherein the one or more RNA molecules and the CRISPR nuclease do not naturally occur together and the one or more RNA molecules are configured to form a complex with the CRISPR nuclease and/or target the complex to a target site, and wherein the at least one RNA molecule comprises a sequence selected from the group consisting of SEQ ID NOs: 4-36.

2. The composition of claim 1, wherein the CRISPR nuclease comprises a sequence having at least 90% identity to the amino acid sequence set forth in SEQ ID NO: 1 and at least one RNA molecule is a CRISPR RNA (crRNA) molecule comprising a guide sequence portion and a sequence selected from the group consisting of SEQ ID NOs: 4-7 and 18-21.

3. The composition of claim 2, further comprising a transactivating CRISPR RNA (tracrRNA) molecule comprising a sequence set forth in the group consisting of SEQ ID NOs: 8-14, 17, 22-28, and 32.

4. The composition of claim 1, wherein the CRISPR nuclease comprises a sequence having at least 90% identity to the amino acid sequence set forth in SEQ ID NO: 1 and at least one RNA molecule is a single-guide RNA (sgRNA) molecule comprising a guide sequence portion and a sequence selected from the group consisting of SEQ ID NOs: 4-36.

5. A non-naturally occurring composition comprising a CRISPR nuclease comprising a sequence having at least 90% identity to the amino acid sequence of SEQ ID NO: 1, or a nucleic acid molecule comprising a sequence encoding the CRISPR nuclease, further comprising one or more RNA molecules, or a DNA polynucleotide encoding any one of the one or more RNA molecules, wherein the one or more RNA molecules and the CRISPR nuclease do not naturally occur together and the one or more RNA molecules are configured to form a complex with the CRISPR nuclease and/or target the complex to a target site, and wherein the at least one RNA molecule is a single-guide RNA (sgRNA) molecule comprising a guide sequence portion and a scaffold portion that is at least 79 nucleotides in length.

6. A non-naturally occurring composition comprising a CRISPR nuclease comprising a sequence having at least 90% identity to the amino acid sequence of SEQ ID NO: 1, or a nucleic acid molecule comprising a sequence encoding the CRISPR nuclease, further comprising one or more RNA molecules, or a DNA polynucleotide encoding any one of the one or more RNA molecules, wherein the one or more RNA molecules and the CRISPR nuclease do not naturally occur together and the one or more RNA molecules are configured to form a complex with the CRISPR nuclease and/or target the complex to a target site, and wherein the CRISPR nuclease is a nickase created by an amino acid substitution at position D12, E776, H988 or D991;

wherein the CRISPR nuclease is a nickase created by an amino acid substitution at position D856, H857 or N880, wherein an amino acid substitution at position D856 is a substitution other than aspartic acid (D) to glutamic acid (E); or wherein the CRISPR nuclease is a catalytically dead nuclease created by an amino acid substitution at any one of positions D12, E776, H988 or D991 and an amino acid substitution at any one of positions D856, H857 or N880, wherein an amino acid substitution at position D856 is a substitution other than aspartic acid (D) to glutamic acid (E).

7. A method of modifying a nucleotide sequence at a DNA target site in a cell-free system or the genome of a cell comprising introducing into the cell a non-naturally occurring composition comprising a CRISPR nuclease comprising a sequence having at least 90% identity to the amino acid sequence of SEQ ID NO: 1, or a nucleic acid molecule comprising a sequence encoding the CRISPR nuclease, further comprising one or more RNA molecules, or a DNA polynucleotide encoding any one of the one or more RNA molecules, wherein the one or more RNA molecules and the CRISPR nuclease do not naturally occur together and the one or more RNA molecules are configured to form a complex with the CRISPR nuclease and/or target the complex to a target site, and wherein the CRISPR nuclease effects a DNA strand break adjacent to a NNRRHY, NNRACT, or NNRVCT protospacer adjacent motif (PAM) sequence, and/or effects a DNA strand break adjacent to a sequence that is complementary to the PAM sequence;

wherein the CRISPR nuclease is a nickase created by an amino acid substitution at position D12, E776, H988 or D991, and effects a DNA strand break adjacent to the PAM sequence; or wherein the CRISPR nuclease is a nickase created by an amino acid substitution at position D856, H857 or N880, and effects a DNA strand break adjacent to a sequence that is complementary to the PAM sequence, and wherein an amino acid substitution at position D856 is a substitution other than aspartic acid (D) to glutamic acid (E).

8. The composition of claim 2, wherein the guide sequence portion of the crRNA molecule is 17-24 nucleotides in length.

9. The composition of claim 2, wherein the guide sequence portion of the crRNA molecule is 22 nucleotides in length.

10. The composition of claim 4, wherein the guide sequence portion of the sgRNA molecule wherein the crRNA molecule is 17-24 nucleotides in length.

11. The composition of claim 4, wherein the guide sequence portion of the sgRNA molecule is 22 nucleotides in length.

* * * * *